United States Patent
Wang et al.

(10) Patent No.: US 12,037,586 B2
(45) Date of Patent: *Jul. 16, 2024

(54) 4'-PHOSPHATE ANALOGS AND OLIGONUCLEOTIDES COMPRISING THE SAME

(71) Applicant: Dicerna Pharmaceuticals, Inc., Lexington, MA (US)

(72) Inventors: Weimin Wang, Newton, MA (US); Qingyi Li, Somerville, MA (US); Naim Nazef, Cambridge, MA (US)

(73) Assignee: DICERNA PHARMACEUTICALS, INC., Lexington, MA (US)

( * ) Notice: Subject to any disclaimer, the term of this patent is extended or adjusted under 35 U.S.C. 154(b) by 60 days.

This patent is subject to a terminal disclaimer.

(21) Appl. No.: 17/859,781

(22) Filed: Jul. 7, 2022

(65) Prior Publication Data

US 2023/0064031 A1 Mar. 2, 2023

Related U.S. Application Data

(63) Continuation of application No. 16/328,546, filed as application No. PCT/US2017/049909 on Sep. 1, 2017, now Pat. No. 11,414,659.

(60) Provisional application No. 62/383,207, filed on Sep. 2, 2016, provisional application No. 62/393,401, filed on Sep. 12, 2016.

(51) Int. Cl.

| | |
|---|---|
| *C12N 15/113* | (2010.01) |
| *A61K 31/7115* | (2006.01) |
| *A61K 31/712* | (2006.01) |
| *A61K 31/7125* | (2006.01) |
| *A61K 45/06* | (2006.01) |
| *A61K 47/54* | (2017.01) |
| *A61K 47/60* | (2017.01) |
| *C07H 19/10* | (2006.01) |
| *C07H 21/02* | (2006.01) |
| *C07H 21/04* | (2006.01) |

(52) U.S. Cl.
CPC ........ *C12N 15/113* (2013.01); *A61K 31/7115* (2013.01); *A61K 31/712* (2013.01); *A61K 31/7125* (2013.01); *A61K 45/06* (2013.01); *A61K 47/549* (2017.08); *A61K 47/60* (2017.08); *C07H 19/10* (2013.01); *C07H 21/02* (2013.01); *C07H 21/04* (2013.01); *C12N 2310/14* (2013.01); *C12N 2310/31* (2013.01); *C12N 2310/322* (2013.01); *C12N 2310/344* (2013.01); *C12N 2310/3515* (2013.01)

(58) Field of Classification Search
None
See application file for complete search history.

(56) References Cited

U.S. PATENT DOCUMENTS

| | | |
|---|---|---|
| 5,798,340 A | 8/1998 | Bischofberger et al. |
| 5,977,061 A | 11/1999 | Holy et al. |
| 5,998,603 A | 12/1999 | Cook et al. |
| 7,247,621 B2 | 7/2007 | Hong et al. |
| 8,927,513 B2 | 1/2015 | Manoharan et al. |
| 8,987,435 B2 | 3/2015 | Swayze et al. |
| 9,364,554 B2 | 6/2016 | Hutchinson et al. |
| 2006/0003952 A1 | 1/2006 | Ravikumar et al. |
| 2009/0275535 A1 | 11/2009 | Boojamra et al. |
| 2011/0250138 A1 | 10/2011 | Fan et al. |
| 2013/0336994 A1 | 12/2013 | Hutchinson et al. |
| 2015/0315226 A1 | 11/2015 | Butora |
| 2019/0177355 A1 | 6/2019 | Wang et al. |

FOREIGN PATENT DOCUMENTS

| | | |
|---|---|---|
| EP | 0398231 A2 | 11/1990 |
| JP | 2007-211025 A | 8/2007 |
| JP | 2019-526555 A | 9/2019 |
| WO | 2008/100447 A2 | 8/2008 |
| WO | 2011/005860 A2 | 1/2011 |
| WO | 2011/123621 A2 | 10/2011 |
| WO | 2011/133871 A2 | 10/2011 |
| WO | 2011/139702 A2 | 11/2011 |
| WO | 2015/106128 A2 | 7/2015 |
| WO | 2016/099982 A2 | 6/2016 |
| WO | 2016/106050 A1 | 6/2016 |
| WO | 2016/142486 A1 | 9/2016 |
| WO | 2016/174081 A1 | 11/2016 |

OTHER PUBLICATIONS

International Search Report and Written Opinion dated Dec. 4, 2017 from International Application No. PCT/US2017/049909 (Authorized Officer, Lee W. Young), 11 Pages.
Drake et al., "Preparation of carbocyclic analogues of 2'-deoxyribonucleotides possessing a phosphonate substituent at the 5'-position", J. Chem. Soc., Perkin Trans. 1, 1996, pp. 2739-2745.
Kenski et al., "In Vivo Activity and Duration of Short Interfering RNAs Containing a Synthetic 5'-Phosphate", Nucleic Acid Therapeutics, 2012, 6 pages.
Prakash et al., "Identification of metabolically stable 5'-phosphate analogs that support single-stranded siRNA activity", Nucleic Acids Research, 2015, vol. 43, No. 6, pp. 2993-3011.
Pradere et al. "Synthesis of Nucleoside Phosphate and Phosphonate Prodrugs", Chem. Rev., 2014, vol. 114, pp. 9154-9218.

(Continued)

*Primary Examiner* — Patrick T Lewis

(74) *Attorney, Agent, or Firm* — MH2 TECHNOLOGY LAW GROUP, LLP

(57) ABSTRACT

Disclosed herein are oligonucleotides, such as nucleic acid inhibitor molecules, having a 4'-phosphate analog and methods of using the same, for example, to modulate the expression of a target gene in a cell. The phosphate analogs are bound to the 4'-carbon of the sugar moiety (e.g., a ribose or deoxyribose or analog thereof) of the 5'-terminal nucleotide of an oligonucleotide. Typically, the phosphate analog is an oxymethylphosphonate, where the oxygen atom of the oxymethyl group is bound to the 4'-carbon of the sugar moiety or analog thereof.

26 Claims, 16 Drawing Sheets

(56) References Cited

OTHER PUBLICATIONS

Extended European Search Report for European Patent Application No. 17847638.8 dated Jan. 29, 2020, 8 pages.
Office Action dated Mar. 16, 2021 for corresponding Japanese Patent Application No. 2019-511707, 8 pages (with English translation).
Office Action and Search Report dated Aug. 4, 2021 for corresponding Chinese Patent Application No. 201780068124.5, 17 pages (with English translation).
Točik et al., "Novel Isosteric, Isopolar Phosphonate Analogs of Oligonucleotides: Preparation and Properties", Biopolymers, 2006, vol. 83, pp. 400-413.
Office Action dated Apr. 12, 2022 for corresponding Chinese Patent Application No. 201780068124.5, 16 pages with English translation.

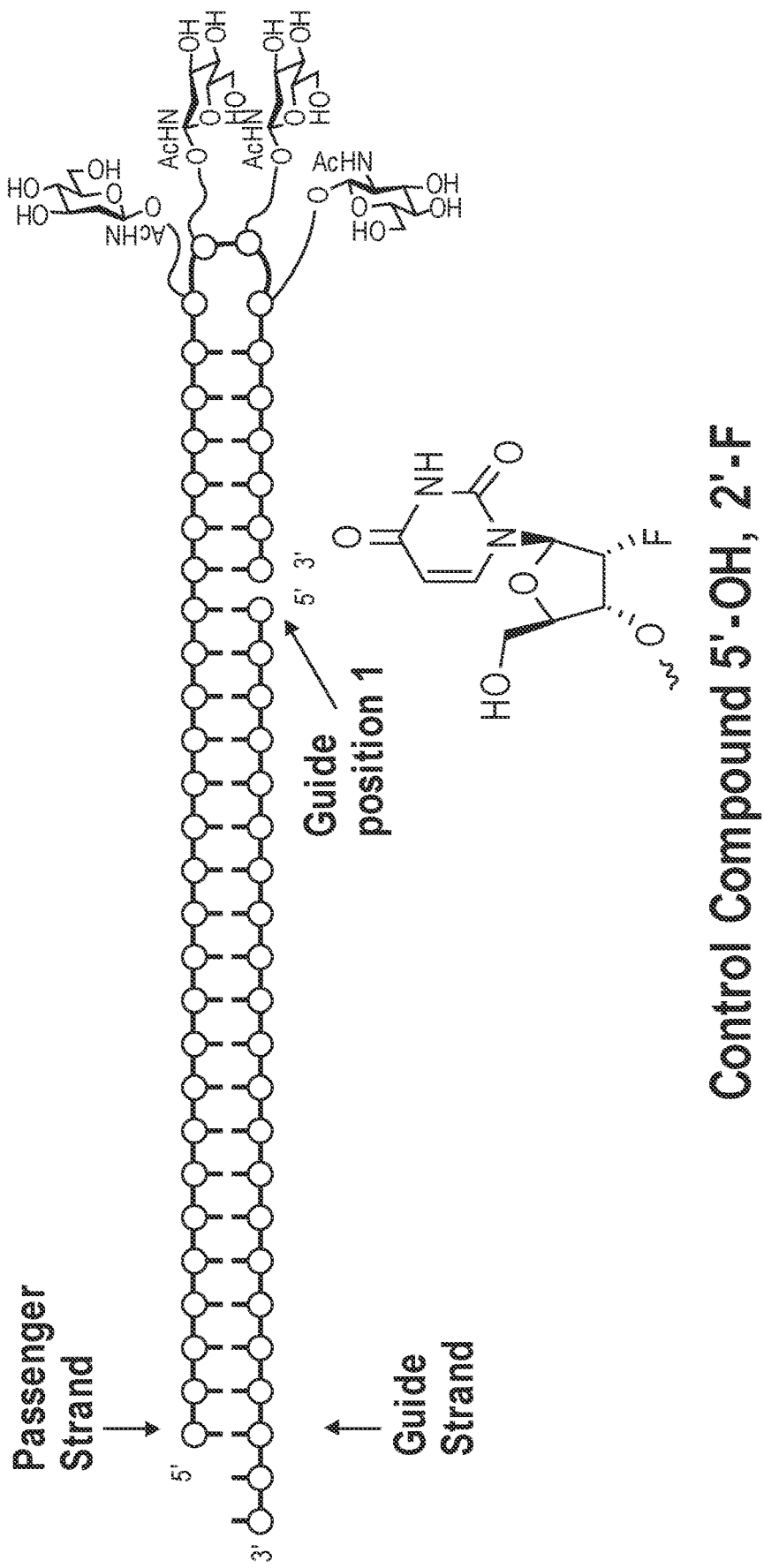
FIG. 1A Control Compound 5'-OH, 2'-F

Test Compound Fully Deprotected, 2'-F

Test Compound Monomethyl Protected, 2'-F

Control Compound 5'-OH, 2'-OMe

Test Compound Fully Deprotected, 2'-OMe

Test Compound Monomethyl Protected, 2'-OMe

Test Compound Fully Deprotected, 2'-F

Test Compound Monomethyl Protected, 2'-F

Test Compound Fully Deprotected, 2'-F

Test Compound Monomethyl Protected, 2'-F

4'-PHOSPHATE ANALOGS AND OLIGONUCLEOTIDES COMPRISING THE SAME

CROSS REFERENCE TO RELATED APPLICATIONS

This application is a continuation of U.S. patent application Ser. No. 16/328,546 filed 26 Feb. 2019, which is a U.S. National Stage application of PCT/US2017/049909 filed 1 Sep. 2017, which claims the benefit of, and relies on the filing date of, U.S. provisional patent application No. 62/383,207, filed 2 Sep. 2016 and U.S. provisional patent application No. 62/393,401, filed 12 Sep. 2016, and the entire disclosures of which are incorporated herein by reference.

BACKGROUND

Oligonucleotides are polymeric sequences of nucleotides (RNA, DNA and their analogs). Nucleic acid inhibitor molecules are oligonucleotides that modulate intracellular RNA levels and have demonstrated early promise in the treatment of cancers, viral infections and genetic disorders. Nucleic acid inhibitor molecules can modulate RNA expression through a diverse set of mechanisms, including RNA interference (RNAi).

RNAi is a conserved pathway found in most eukaryotes where double-stranded RNA molecules (dsRNA) inhibit the expression of target genes having sequences complementary to the dsRNA. In the typical RNAi pathway, longer dsRNA are cleaved by the Dicer enzyme into shorter RNA duplexes called small interfering RNA ("siRNA"). The siRNA has been shown to associate with Dicer, trans-activating response RNA-binding protein (TRBP), and Argonaute 2 ("Ago2") to form a complex, sometimes referred to as the RNA-induced silencing complex ("RISC"). Ago2 is an endonuclease that cleaves target mRNA using the antisense strand (also called the guide strand) of the siRNA to direct the sequence specificity of the target mRNA cleavage.

A variety of double stranded RNAi inhibitor molecule structures have been developed over the years. For example, early work on RNAi inhibitor molecules focused on double-stranded nucleic acid molecules that mimic natural siRNAs, with each strand having sizes of 19-25 nucleotides with at least one 3'-overhang of 1 to 5 nucleotides (see, e.g., U.S. Pat. No. 8,372,968). Subsequently, longer double-stranded RNAi inhibitor molecules that get processed in vivo by the Dicer enzyme to active RNAi inhibitor molecules were developed (see, e.g., U.S. Pat. No. 8,883,996). Later work developed extended double-stranded nucleic acid inhibitor molecules where at least one end of at least one strand is extended beyond the double-stranded targeting region of the molecule, including structures where one of the strands includes a thermodynamically-stabilizing tetraloop structure (see, e.g., U.S. Pat. Nos. 8,513,207, 8,927,705, WO 2010/033225, and WO 2016/100401). Those structures include single-stranded extensions (on one or both sides of the molecule) and double-stranded extensions.

Single stranded nucleic acid inhibitor molecules are also known in the art. For example, recent efforts have demonstrated activity of ssRNAi inhibitor molecules (see, e.g., Matsui et al. 2016, 24(5):946-55. And, antisense molecules have been used for decades to reduce expression of specific target genes. Pelechano and Steinmetz, *Nature Review Genetics,* 2013, 14:880-93. A number of variations on the common themes of these structures have been developed for a range of targets. Other single stranded nucleic acid inhibitor molecules include, for example, microRNA, ribozymes, antagomirs, and aptamers, all of which are known in the art.

In certain instances, chemical modifications have been introduced into nucleic acid inhibitor molecules to introduce properties that may be desired under specific conditions, such as conditions experienced following in vivo administration. Such modifications include those designed, for example, to stabilize against nucleases or other enzymes that degrade or interfere with the structure or activity of the oligonucleotide, to increase cellular uptake of the oligonucleotide, or to improve the pharmacokinetic properties of the oligonucleotide.

For example, synthetic oligonucleotides generally terminate with a 5'- or 3'-hydroxyl group. It is possible to replace the terminal hydroxyl group with a phosphate group, which can be used, for example, to attach linkers, adapters or labels or for the direct ligation of an oligonucleotide to another nucleic acid. In addition, it has been reported that a 5'-terminal phosphate group enhances the interaction between certain nucleic acid inhibitor molecules and Ago2. However, oligonucleotides having a 5'-phosphate group are generally susceptible to degradation via phosphatases or other enzymes, which can limit their bioavailability in vivo.

Therefore, it is desirable to develop modifications to the 5'-terminal nucleotide of oligonucleotides, such as nucleic acid inhibitor molecules, that provide the functional effect of a phosphate group, but are more stable to the environmental conditions that the oligonucleotide will be exposed to when administered to a subject. Such phosphate analogs would be more resistant to phosphatases and other enzymes while minimizing negative impact on the oligonucleotide's function (e.g., minimizing any reduction in gene target knockdown when used in an RNAi inhibitor molecule).

SUMMARY

This application discloses oligonucleotides comprising 4'-phosphate analogs. Suitable oligonucleotides include nucleic acid inhibitor molecules, such as dsRNAi inhibitor molecules, antisense oligonucleotides, miRNA, ribozymes, antagomirs, aptamers, and ssRNAi inhibitor molecules.

The phosphate analogs of the present disclosure are bound to the 4'-carbon of the sugar moiety (e.g., a ribose or deoxyribose or analog thereof) of the 5'-terminal nucleotide ("N1 nucleotide") of an oligonucleotide as described herein. Typically, the phosphate analog is an oxymethylphosphonate, where the oxygen atom of the oxymethyl group is bound to the 4'-carbon of the sugar moiety or analog thereof. In other embodiments, the phosphate analog is a thiomethylphosphonate or an aminomethylphosphonate, where the sulfur atom of the thiomethyl group or the nitrogen atom of the aminomethyl group is bound to the 4'-carbon of the sugar moiety or analog thereof.

In certain embodiments, the 4'-oxymethylphosphonate is represented by —O—CH$_2$—PO(OH)$_2$ or —O—CH$_2$—PO(OR)$_2$, where R is independently selected from H, CH$_3$, an alkyl group, or a protecting group. In certain embodiments, the alkyl group is CH$_2$CH$_3$.

In one aspect, the phosphate analog-modified nucleic acid inhibitor molecules described herein can be used to modulate expression of a target gene in a cell. The phosphate analog-modified nucleic acid inhibitor molecules can be formulated with a pharmaceutically acceptable excipient as a pharmaceutical composition and used to modulate the expression of target genes and to treat patients in need thereof.

In certain aspects, the present disclosure is directed to an oligonucleotide comprising a 5'-terminal nucleotide comprising an 4'-oxymethylphosphonate, wherein the 4'-oxymethylphosphonate is —O—$CH_2$—PO(OH)$_2$ or —O—$CH_2$—PO(OR)$_2$, and wherein R is independently selected from H, $CH_3$, an alkyl group, or a protecting group. In certain embodiments, the alkyl group is $CH_2CH_3$.

In certain aspects, the present disclosure is directed to an oligonucleotide comprising a 5'-terminal nucleotide represented by Formula I or II, as described herein. In certain embodiments, the 5'-terminal nucleotide is represented by Formula I, as described herein. In certain embodiments, the oligonucleotide is represented by Formula I and $X_2$ is OH, F, $OCH_2CH_2OCH_3$, or $OCH_3$ and $R_8$ is absent or wherein $X_2$ is O and $R_8$ is a glutathione-sensitive moiety.

In certain aspects, the present disclosure is directed to an oligonucleotide comprising a 5'-terminal nucleotide represented by Formula III, as described herein. In certain embodiments of the oligonucleotide, $X_2$ is OH, F, or $OCH_3$ and $R_8$ is absent.

In certain embodiments of the oligonucleotides described herein, $R^a$ and $R^b$ are hydrogen; $R^a$ is $CH_3$ or $CH_2CH_3$ and $R^b$ is hydrogen; or $R^a$ and $R^b$ are each $CH_3$ or $CH_2CH_3$.

In certain aspects, the present disclosure is directed to an oligonucleotide comprising a 5'-terminal nucleotide represented by Formula IV, as described herein.

In certain aspects, the present disclosure is directed to an oligonucleotide comprising a 5'-terminal nucleotide represented by Formula V, as described herein.

In certain aspects, the present disclosure is directed to an oligonucleotide comprising a 5'-terminal nucleotide represented by Formula VI, as described herein. In certain embodiments, the sugar moiety is a furanose.

In certain embodiments, the oligonucleotide is a double-stranded RNAi inhibitor molecule comprising a first strand and a second strand, wherein the first strand is a sense strand and the second strand is an antisense strand. In certain embodiments, the double stranded RNAi inhibitor molecule comprises a region of complementarity between the sense strand and the antisense strand of 15 to 45 nucleotides. In certain embodiments, the region of complementarity between the sense strand and the antisense strand is 20 to 30 nucleotides. In certain embodiments, the region of complementarity between the sense strand and the antisense strand is 21 to 26 nucleotides. In certain embodiments, the region of complementarity between the sense strand and the antisense strand is 19 to 24 nucleotides. In certain embodiments, the region of complementarity between the sense strand and the antisense strand is 19 to 21 nucleotides.

In certain embodiments, the 5'-terminal nucleotide is located on the antisense strand. In certain embodiments, the 5'-terminal nucleotide is located on the sense strand.

In certain embodiments, the double-stranded RNAi inhibitor molecule contains a tetraloop.

In certain embodiments, the oligonucleotide is a single stranded oligonucleotide. In certain embodiments, the single-stranded oligonucleotide is a conventional antisense oligonucleotide, a ribozyme or an aptamer.

In certain embodiments, the single stranded oligonucleotide is a single stranded RNAi inhibitor molecule. In certain embodiments, the single stranded RNAi inhibitor molecule is 14-50 nucleotides in length. In certain embodiments, the single stranded RNAi inhibitor molecule is about 16-30, 18-22, or 20-22 nucleotides in length.

In certain embodiments, the oligonucleotide further comprises at least one delivery agent, wherein the at least one delivery agent is conjugated to the oligonucleotide to facilitate transport of the oligonucleotide across an outer membrane of a cell. In certain embodiments, the delivery agent is selected from the group consisting of carbohydrates, peptides, lipids, vitamins and antibodies. In certain embodiments, the delivery agent is selected from N-Acetylgalactosamine (GalNAc), mannose-6-phosphate, galactose, oligosaccharide, polysaccharide, cholesterol, polyethylene glycol, folate, vitamin A, vitamin E, lithocholic acid and a cationic lipid.

In certain embodiment, the oligonucleotide is contained in a lipid nanoparticle. In certain embodiments, the oligonucleotide is a naked oligonucleotide.

In certain aspects, the present disclosure is directed to a pharmaceutical composition comprising an oligonucleotide (e.g., nucleic acid inhibitor molecule) comprising a 4'-phosphate analog, as described herein, and a pharmaceutically acceptable excipient and methods of using the same to reduce expression of a target gene in a subject comprising administering the pharmaceutical composition to a subject in need thereof in an amount sufficient to reduce expression of the target gene. In certain embodiments, the administering comprises systemic administration.

In certain aspects, the present disclosure is directed to a nucleoside phosphoramidite, wherein the nucleoside phosphoramidite is represented by Formula X or Formula XI, as described herein. In certain embodiments of the nucleoside phosphoramidite, $M_1$ is O and $X_{10}$ is O. In certain embodiments of the nucleoside phosphoramidite, $X_2$ is O and $R_8$ is a glutathione-sensitive moiety. In certain embodiments of the nucleoside phosphoramidite, $X_2$ is F, $OCH_2CH_2OCH_3$ or $OCH_3$ and $R_8$ is absent. In certain embodiments of the nucleoside phosphoramidite, $R^c$ and $R^d$ are each $CH_3$ or $CH_2CH_3$.

In certain aspects, the present disclosure is directed to a nucleoside phosphoramidite, wherein the nucleoside phosphoramidite is represented by Formula XII, as described herein. In certain embodiments of the nucleoside phosphoramidite, $R^c$ and $R^d$ is each independently selected from $CH_3$, $CH_2CH_3$, or a protecting group. In certain embodiments of the nucleoside phosphoramidite, $X_2$ is F or $OCH_3$ and $R_8$ is absent. In certain embodiments of the nucleoside phosphoramidite, $X_2$ is O and $R_8$ is a glutathione sensitive moiety.

In certain aspects, the present disclosure is directed to a nucleoside phosphoramidite, wherein the nucleoside phosphoramidite is represented by Formula XIII, as described herein.

In certain aspects, the present disclosure is directed to a nucleoside phosphoramidite, wherein the nucleoside phosphoramidite is represented by Formula XIV, as described herein.

In certain aspects, the present disclosure is directed to a nucleoside phosphoramidite, wherein the nucleoside phosphoramidite is represented by Formula XV, as described herein. In certain embodiments, the sugar moiety is a furanose. In certain embodiments, $R^c$ and $R^d$ are each $CH_3$ or $CH_2CH_3$.

DETAILED DESCRIPTION

Definitions

Figure 1A:
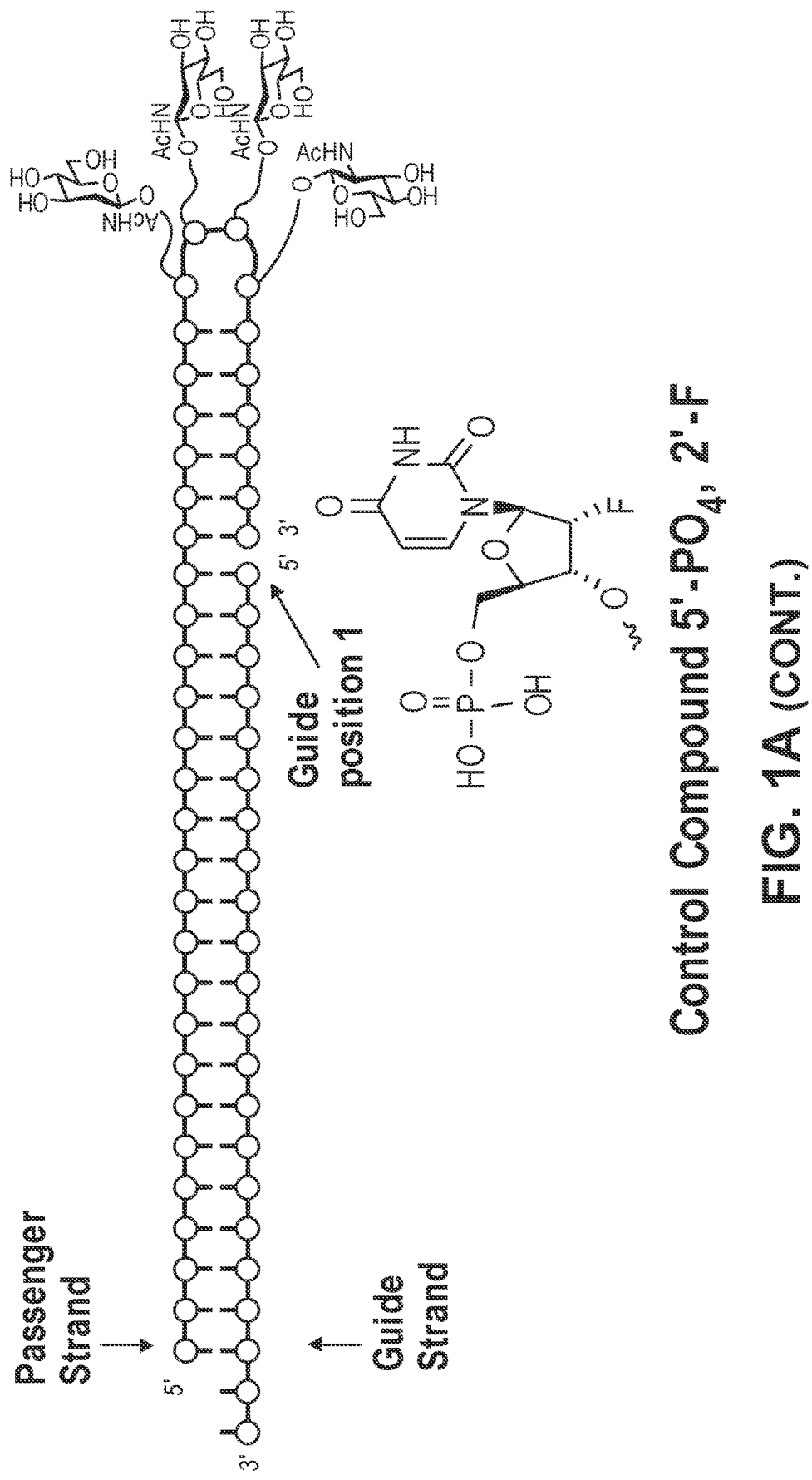
FIG. 1A depicts two representative control double stranded RNAi inhibitor molecules as described in the Examples: Control Compound 5'-OH, 2'-F and Control Compound 5'-$PO_4$, 2'-F. Control Compound 5'-OH, 2'-F and Control Compound 5'-$PO_4$, 2'-F are identical except for the 5'-OH or 5'-$PO_4$ of the N1 nucleotide of the guide strand.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

5'-terminal nucleotide: As used herein, the term "5'-terminal nucleotide" refers to the nucleotide located at the 5'-end of an oligonucleotide. The 5'-terminal nucleotide may also be referred to as the "N1 nucleotide" in this application.

Acyl: As used herein, the term "acyl" refers to an alkylcarbonyl, cycloalkylcarbonyl and arylcarbonyl moiety.

Aliphatic group: As used herein, the term "aliphatic group" refers to both saturated and unsaturated, straight chain (i.e., unbranched), or branched, hydrocarbons, which are optionally substituted with one or more functional groups. The term "substituted aliphatic" refers to aliphatic moieties bearing substituents.

Alkoxy: As used herein, the term "alkoxy" refers to an alkyl group attached to a molecular moiety through an oxygen atom.

Alkenyl: As used herein, the term "alkenyl" refers to straight or branched chain hydrocarbyl groups having at least one carbon-carbon double bond, and having in the range of about 2 to about 20 carbon atoms. "Substituted alkenyl" refers to alkenyl groups further bearing one or more substituents. As used herein, "lower alkenyl" refers to alkenyl moieties having from 2 to about 6 carbon atoms.

Alkyl: As used herein, the term "alkyl" refers to straight or branched chain hydrocarbyl groups having from 1 up to about 20 carbon atoms. Whenever it appears herein, a numerical range, such as "$C_1$-$C_6$ alkyl" means that an alkyl group may comprise only 1 carbon atom, 2 carbon atoms, 3 carbon atoms, etc., up to and including 6 carbon atoms, although the term "alkyl" also includes instances where no numerical range of carbon atoms is designated. For example, the term "alkyl" can refer to a sub-range between $C_1$-$C_{10}$ (e.g. $C_1$-$C_6$). "Substituted alkyl" refers to alkyl moieties bearing substituents. As used herein, "lower alkyl" refers to alkyl moieties having from 1 to about 6 carbon atoms.

Alkylamino: As used herein, the term "alkylamino" refers to an alkyl radical bearing an amine functionality. Alkylaminos may be substituted or unsubstituted.

Alkynyl: As used herein, "alkynyl" refers to straight or branched chain hydrocarbyl groups having at least one carbon-carbon triple bond, and having in the range of about 2 to about 20 carbon atoms. "Substituted alkynyl" refers to alkynyl groups further bearing one or more substituents. As used herein, "lower alkynyl" refers to alkynyl moieties having from about 2 to about 6 carbon atoms.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Aptamer: As used herein, the term "aptamer" refers to an oligonucleotide that has binding affinity for a specific target including a nucleic acid, a protein, a specific whole cell or a particular tissue. Aptamers may be obtained using methods known in the art, for example, by in vitro selection from a large random sequence pool of nucleic acids. Lee et al., *Nucleic Acid Res.*, 2004, 32:D95-D100.

Antagomir: As used herein, the term "antagomir" refers to an oligonucleotide that has binding affinity for a specific target including the guide strand of an exogenous RNAi inhibitor molecule or natural miRNA (Krutzfeldt et al. *Nature* 2005, 438(7068):685-689).

Antisense strand: A double stranded RNAi inhibitor molecule comprises two oligonucleotide strands: an antisense strand and a sense strand. The antisense strand or a region thereof is partially, substantially or fully complementary to a corresponding region of a target nucleic acid. In addition, the antisense strand of the double stranded RNAi inhibitor molecule or a region thereof is partially, substantially or fully complementary to the sense strand of the double stranded RNAi inhibitor molecule or a region thereof. In certain embodiments, the antisense strand may also contain nucleotides that are non-complementary to the target nucleic acid sequence. The non-complementary nucleotides may be on either side of the complementary sequence or may be on both sides of the complementary sequence. In certain embodiments, where the antisense strand or a region thereof is partially or substantially complementary to the sense strand or a region thereof, the non-complementary nucleotides may be located between one or more regions of complementarity (e.g., one or more mismatches). The antisense strand of a double stranded RNAi inhibitor molecule is also referred to as the guide strand.

Aromatic Group: The term "aromatic group" as used herein refers to a planar ring having a delocalized π-electron system containing 4n+2π electrons, where n is an integer. Aromatic rings can be formed from five, six, seven, eight, nine, or more than nine atoms. The term "aromatic" is intended to encompass both carbocyclic aryl (e.g., phenyl) and heterocyclic aryl (or "heteroaryl" or "heteroaromatic") groups (e.g., pyridine). The term includes monocyclic or fused-ring polycyclic rings, i.e., rings which share adjacent pairs of carbon atoms. "Substituted aromatic" refers to an aromatic group further bearing one or more substituents.

Aryl: As used herein, the term "aryl" refers to an aromatic monocyclic or multicyclic groups having in the range of 5 up to 19 carbon atoms. "Substituted aryl" refers to aryl groups further bearing one or more substituents.

Canonical RNA inhibitor molecule: As used herein, the term "canonical RNA inhibitor molecule" refers to two strands of nucleic acids, each 21 nucleotides long with a central region of complementarity that is 19 base-pairs long for the formation of a double stranded nucleic acid and two nucleotide overhands at each of the 3'-ends.

Complementary: As used herein, the term "complementary" refers to a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. "Fully complementarity" or 100% complementarity refers to the situation in which each nucleotide monomer of a first oligonucleotide strand or of a segment of a first oligonucleotide strand can form a base pair with each nucleotide monomer of a second oligonucleotide strand or of a segment of a second oligonucleotide strand. Less than 100% complementarity refers to the situation in which some, but not all, nucleotide monomers of two oligonucleotide strands (or two segments of two oligonucleotide strands) can form base pairs with each other. "Substantial complementarity" refers to two oligonucleotide strands (or segments of two oligonucleotide strands) exhibiting 90% or greater complementarity to each other. "Sufficiently complementary" refers to complementarity between a target mRNA and a nucleic acid inhibitor molecule, such that there is a reduction in the amount of protein encoded by a target mRNA.

Complementary strand: As used herein, the term "complementary strand" refers to a strand of a double stranded nucleic acid inhibitor molecule that is partially, substantially or fully complementary to the other strand.

Conventional antisense oligonucleotide: As used herein, the term "conventional antisense oligonucleotide" refers to single stranded oligonucleotides that inhibit the expression of a targeted gene by one of the following mechanisms: (1) Steric hindrance, e.g., the antisense oligonucleotide interferes with some step in the sequence of events involved in gene expression and/or production of the encoded protein by directly interfering with, for example, transcription of the gene, splicing of the pre-mRNA and translation of the mRNA; (2) Induction of enzymatic digestion of the RNA transcripts of the targeted gene by RNase H; (3) Induction of enzymatic digestion of the RNA transcripts of the targeted gene by RNase L; (4) Induction of enzymatic digestion of the RNA transcripts of the targeted gene by RNase P: (5) Induction of enzymatic digestion of the RNA transcripts of the targeted gene by double stranded RNase; and (6) Combined steric hindrance and induction of enzymatic digestion activity in the same antisense oligo. Conventional antisense oligonucleotides do not have an RNAi mechanism of action like RNAi inhibitor molecules. RNAi inhibitor molecules can be distinguished from conventional antisense oligonucleotides in several ways including the requirement for Ago2 that combines with an RNAi antisense strand such that the antisense strand directs the Ago2 protein to the intended target(s) and where Ago2 is required for silencing of the target.

CRISPR RNA: Clustered Regularly Interspaced Short Palindromic Repeats ("CRISPR") is a microbial nuclease system involved in defense against invading phages and plasmids. Wright et al., Cell, 2016,164:29-44. This prokaryotic system has been adapted for use in editing target nucleic acid sequences of interest in the genome of eukaryotic cells. Cong et al., Science, 2013,339:819-23; Mali et al., Science, 2013,339:823-26; Woo Cho et al., Nat. Biotechnology, 2013, 31(3):230-232. As used herein, the term "CRISPR RNA" refers to a nucleic acid comprising a "CRISPR" RNA (crRNA) portion and/or a trans activating crRNA (tracrRNA) portion, wherein the CRISPR portion has a first sequence that is partially, substantially or fully complementary to a target nucleic acid and a second sequence (also called the tracer mate sequence) that is sufficiently complementary to the tracrRNA portion, such that the tracer mate sequence and tracrRNA portion hybridize to form a guide RNA. The guide RNA forms a complex with an endonuclease, such as a Cas endonuclease (e.g., Cas9) and directs the nuclease to mediate cleavage of the target nucleic acid. In certain embodiments, the crRNA portion is fused to the tracrRNA portion to form a chimeric guide RNA. Jinek et al., Science, 2012,337:816-21. In certain embodiments, the first sequence of the crRNA portion includes between about 16 to about 24 nucleotides, preferably about 20 nucleotides, which hybridize to the target nucleic acid. In certain embodiments, the guide RNA is about 10-500 nucleotides. In other embodiments, the guide RNA is about 20-100 nucleotides.

Cycloalkyl: As used herein, the term "cycloalkyl" refers to cyclic (i.e., ring-containing) hydrocarbon groups containing 3 to 12 carbons, for example, 3 to 8 carbons and, for example, 3 to 6 carbons. "Substituted cycloalkyl" refers to cycloalkyl groups further bearing one or more substituents.

Delivery agent: As used herein, the term "delivery agent" refers to a transfection agent or a ligand that is complexed with or bound to an oligonucleotide and which mediates its entry into cells. The term encompasses cationic liposomes, for example, which have a net positive charge that binds to the oligonucleotide's negative charge. This term also encompasses the conjugates as described herein, such as GalNAc and cholesterol, which can be covalently attached to an oligonucleotide to direct delivery to certain tissues. Further specific suitable delivery agents are also described herein.

Deoxyribonucleotide: As used herein, the term "deoxyribonucleotide" refers to a nucleotide which has a hydrogen group at the 2'-position of the sugar moiety.

Disulfide: As used herein, the term "disulfide" refers to a chemical compound containing the group

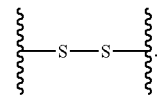

Typically, each sulfur atom is covalently bound to a hydrocarbon group. In certain embodiments, at least one sulfur atom is covalently bound to a group other than a hydrocarbon. The linkage is also called an SS-bond or a disulfide bridge.

Duplex: As used herein, the term "duplex" in reference to nucleic acids (e.g., oligonucleotides), refers to a double helical structure formed through complementary base pairing of two antiparallel sequences of nucleotides.

Excipient: As used herein, the term "excipient" refers to a non-therapeutic agent that may be included in a composition, for example to provide or contribute to a desired consistency or stabilizing effect.

Furanose: As used herein, the term "furanose" refers to a carbohydrate having a five-membered ring structure, where the ring structure has 4 carbon atoms and one oxygen atom and is represented by Formula XVII:

(XVII)

In Formula XVII, the numbers represent the positions of the 4 carbon atoms in the five-membered ring structure.

Glutathione: As used herein, the term "glutathione" (GSH) refers to a tripeptide having the structure of Formula XVIII, below. GSH is present in cells at a concentration of approximately 1-10 mM. GSH reduces glutathione-sensitive bonds, including disulfide bonds. In the process, glutathione is converted to its oxidized form, glutathione disulfide (GSSG). Once oxidized, glutathione can be reduced back by glutathione reductase, using NADPH as an electron donor.

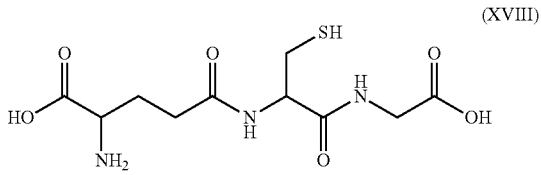 [SMILES: NC(CCC(=O)NC(CS)C(=O)NCC(=O)O)C(=O)O]

(XVIII)

Glutathione-sensitive compound or glutathione-sensitive moiety: As used herein, the terms "glutathione-sensitive compound", or "glutathione-sensitive moiety", are used interchangeably and refers to any chemical compound (e.g., oligonucleotide, nucleotide, or nucleoside) or moiety containing at least one glutathione-sensitive bond, such as a disulfide bridge or a sulfonyl group. As used herein, a "glutathione-sensitive oligonucleotide" is an oligonucleotide containing at least one nucleotide containing a glutathione-sensitive bond.

Halo: As used herein, the terms "halo" and "halogen" are interchangeable and refer to an atom selected from fluorine, chlorine, bromine and iodine.

Haloalkyl: As used herein, the term "haloalkyl" refers to an alkyl group having one or more halogen atoms attached thereto and is exemplified by such groups as chloromethyl, bromoethyl, trifluoromethyl, and the like.

Heteroaryl: As used herein, the term "heteroaryl" refers to an aromatic ring system containing at least one heteroatom selected from nitrogen, oxygen and sulfur. The heteroaryl ring can be fused or otherwise attached to one or more heteroaryl rings, aromatic or nonaromatic hydrocarbon rings or heterocycloalkyl rings.

Heterocycle: As used herein, the terms "heterocycle" or "heterocyclic" refer to nonaromatic cyclic (i.e., ring-containing) groups containing one or more heteroatoms (e.g., N, O, S, or the like) as part of the ring structure, and having in the range of 3 up to 14 carbon atoms. "Substituted heterocyclic" or "substituted heterocycle" refer to heterocyclic groups further bearing one or more substituents.

Internucleotide linking group: As used herein, the term "internucleotide linking group" or "internucleotide linkage" refers to a chemical group capable of covalently linking two nucleoside moieties. Typically, the chemical group is a phosphorus-containing linkage group containing a phospho or phosphite group. Phospho linking groups are meant to include a phosphodiester linkage, a phosphorodithioate linkage, a phosphorothioate linkage, a phosphotriester linkage, a thionoalkylphosphonate linkage, a thionalkylphosphotriester linkage, a phosphoramidite linkage, a phosphonate linkage and/or a boranophosphate linkage. Many phosphorus-containing linkages are well known in the art, as disclosed, for example, in U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050. In other embodiments, the oligonucleotide contains one or more internucleotide linking groups that do not contain a phosphorous atom, such short chain alkyl or cycloalkyl internucleotide linkages, mixed heteroatom and alkyl or cycloalkyl internucleotide linkages, or one or more short chain heteroatomic or heterocyclic internucleotide linkages, including, but not limited to, those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; and amide backbones. Non-phosphorous containing linkages are well known in the art, as disclosed, for example, in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Loop: As used herein, the term "loop" refers to a structure formed by a single strand of a nucleic acid, in which complementary regions that flank a particular single stranded nucleotide region hybridize in a way that the single stranded nucleotide region between the complementary regions is excluded from duplex formation or Watson-Crick base pairing. A loop is a single stranded nucleotide region of any length. Examples of loops include the unpaired nucleotides present in such structures as hairpins and tetraloops.

MicroRNA: As used herein, the terms "microRNA" "mature microRNA" "miRNA" and "miR" are interchangeable and refer to non-coding RNA molecules encoded in the genomes of plants and animals. Typically, mature microRNA are about 18-25 nucleotides in length. In certain instances, highly conserved, endogenously expressed microRNAs regulate the expression of genes by binding to the 3'-untranslated regions (3'-UTR) of specific mRNAs. Certain mature microRNAs appear to originate from long endogenous primary microRNA transcripts (also known as pre-microRNAs, pri-microRNAs, pri-mirs, pri-miRs or pri-pre-microRNAs) that are often hundreds of nucleotides in length (Lee, et al., EMBO J, 2002, 21(17), 4663-4670).

Modified nucleoside: As used herein, the term "modified nucleoside" refers to a nucleoside containing one or more of a modified or universal nucleobase or a modified sugar. The modified or universal nucleobases (also referred to herein as base analogs) are generally located at the 1'-position of a nucleoside sugar moiety and refer to nucleobases other than adenine, guanine, cytosine, thymine and uracil at the 1'-position. In certain embodiments, the modified or universal nucleobase is a nitrogenous base. In certain embodiments, the modified nucleobase does not contain nitrogen atom. See e.g., U.S. Published Patent Application No. 20080274462. In certain embodiments, the modified nucleotide does not contain a nucleobase (abasic). A modified sugar (also referred herein to a sugar analog) includes modified deoxyribose or ribose moieties, e.g., where the modification occurs at the 2', 3'-, 4', or 5'-carbon position of the sugar. The modified sugar may also include non-natural alternative carbon structures such as those present in locked nucleic acids ("LNA") (see, e.g., Koshkin et al. (1998), Tetrahedron, 54,3607-3630); bridged nucleic acids ("BNA") (see, e.g., U.S. Pat. No. 7,427,672 and Mitsuoka et al. (2009), Nucleic Acids Res., 37(4):1225-38); and unlocked nucleic acids ("UNA") (see, e.g., Snead et al. (2013), Molecular Therapy-Nucleic Acids, 2,e103(doi: 10.1038/mtna.2013.36)). Suitable modified or universal nucleobases or modified sugars in the context of the present disclosure are described herein.

Modified nucleotide: As used herein, the term "modified nucleotide" refers to a nucleotide containing one or more of a modified or universal nucleobase, a modified sugar, or a modified phosphate. The modified or universal nucleobases (also referred to herein as base analogs) are generally located at the 1'-position of a nucleoside sugar moiety and refer to nucleobases other than adenine, guanine, cytosine, thymine and uracil at the 1'-position. In certain embodiments, the modified or universal nucleobase is a nitrogenous base. In certain embodiments, the modified nucleobase does not contain nitrogen atom. See e.g., U.S. Published Patent Application No. 20080274462. In certain embodiments, the modified nucleotide does not contain a nucleobase (abasic). A modified sugar (also referred herein to a sugar analog) includes modified deoxyribose or ribose moieties, e.g., where the modification occurs at the 2'-, 3'-, 4'-, or 5'-carbon position of the sugar. The modified sugar may also include non-natural alternative carbon structures such as those present in locked nucleic acids ("LNA") (see, e.g., Koshkin et al. (1998), *Tetrahedron,* 54,3607-3630), bridged nucleic acids ("BNA") (see, e.g., U.S. Pat. No. 7,427,672 and Mitsuoka et al. (2009), *Nucleic Acids Res.,* 37(4):1225-38); and unlocked nucleic acids ("UNA") (see, e.g., Snead et al. (2013), *Molecular Therapy- Nucleic Acids,* 2,e103(doi: 10.1038/mtna.2013.36)). Modified phosphate groups refer to a modification of the phosphate group that does not occur in natural nucleotides and includes non-naturally occurring phosphate mimics as described herein. Modified phosphate groups also include non-naturally occurring internucleotide linking groups, including both phosphorous-containing internucleotide linking groups and non-phosphorous containing linking groups, as described herein. Suitable modified or universal nucleobases, modified sugars, or modified phosphates in the context of the present disclosure are described herein.

Naked oligonucleotide: As used herein, the term "naked oligonucleotide" refers to an oligonucleotide that is not formulated in a protective lipid nanoparticle or other protective formulation and is thus exposed to the blood and endosomal/lysosomal compartments when administered in vivo.

Natural nucleoside: As used herein, the term "natural nucleoside" refers to a heterocyclic nitrogenous base in N-glycosidic linkage with a sugar (e.g., deoxyribose or ribose or analog thereof). The natural heterocyclic nitrogenous bases include adenine, guanine, cytosine, uracil and thymine.

Natural nucleotide: As used herein, the term "natural nucleotide" refers to a heterocyclic nitrogenous base in N-glycosidic linkage with a sugar (e.g., ribose or deoxyribose or analog thereof) that is linked to a phosphate group. The natural heterocyclic nitrogenous bases include adenine, guanine, cytosine, uracil and thymine.

Nucleic acid inhibitor molecule: As used herein, the term "nucleic acid inhibitor molecule" refers to an oligonucleotide molecule that reduces or eliminates the expression of a target gene wherein the oligonucleotide molecule contains a region that specifically targets a sequence in the target gene mRNA. Typically, the targeting region of the nucleic acid inhibitor molecule comprises a sequence that is sufficiently complementary to a sequence on the target gene mRNA to direct the effect of the nucleic acid inhibitor molecule to the specified target gene. The nucleic acid inhibitor molecule may include ribonucleotides, deoxyribonucleotides, and/or modified nucleotides.

Nucleoside: As used herein, the term "nucleoside" refers to a natural nucleotide or a modified nucleoside.

Nucleotide: As used herein, the term "nucleotide" refers to a natural nucleotide or a modified nucleotide.

Nucleotide position: As used herein, the term "nucleotide position" refers to a position of a nucleotide in an oligonucleotide as counted from the nucleotide at the 5'-terminus. For example, nucleotide position 1 refers to the 5'-terminal nucleotide of an oligonucleotide.

Oligonucleotide: As used herein, the term "oligonucleotide" as used herein refers to a polymeric form of nucleotides ranging from 2 to 2500 nucleotides. Oligonucleotides may be single-stranded or double-stranded. In certain embodiments, the oligonucleotide has 500-1500 nucleotides, typically, for example, where the oligonucleotide is used in gene therapy. In certain embodiments, the oligonucleotide is single or double stranded and has 7-100 nucleotides. In certain embodiments, the oligonucleotide is single or double stranded and has 15-100 nucleotides. In another embodiment, the oligonucleotide is single or double stranded has 15-50 nucleotides, typically, for example, where the oligonucleotide is a nucleic acid inhibitor molecule. In another embodiment, the oligonucleotide is single or double stranded has 25-40 nucleotides, typically, for example, where the oligonucleotide is a nucleic acid inhibitor molecule. In yet another embodiment, the oligonucleotide is single or double stranded and has 19-40 or 19-25 nucleotides, typically, for example, where the oligonucleotide is a double-stranded nucleic acid inhibitor molecule and forms a duplex of at least 18-25 base pairs. In other embodiments, the oligonucleotide is single stranded and has 15-25 nucleotides, typically, for example, where the oligonucleotide nucleotide is a single stranded RNAi inhibitor molecule. Typically, the oligonucleotide contains one or more phosphorous-containing internucleotide linking groups, as described herein. In other embodiments, the internucleotide linking group is a non-phosphorus containing linkage, as described herein.

Overhang: As used herein, the term "overhang" refers to terminal non-base pairing nucleotide(s) at either end of either strand of a double-stranded nucleic acid inhibitor molecule. In certain embodiments, the overhang results from one strand or region extending beyond the terminus of the complementary strand to which the first strand or region forms a duplex. One or both of two oligonucleotide regions that are capable of forming a duplex through hydrogen bonding of base pairs may have a 5'- and/or 3'-end that extends beyond the 3'- and/or 5'-end of complementarity shared by the two polynucleotides or regions. The single-stranded region extending beyond the 3'- and/or 5'-end of the duplex is referred to as an overhang.

Pharmaceutical composition: As used herein, the term "pharmaceutical composition" comprises a pharmacologically effective amount of a phosphate analog-modified oligonucleotide and a pharmaceutically acceptable excipient. As used herein, "pharmacologically effective amount" "therapeutically effective amount" or "effective amount" refers to that amount of a phosphate analog-modified oligonucleotide of the present disclosure effective to produce the intended pharmacological, therapeutic or preventive result.

Pharmaceutically acceptable excipient: As used herein, the term "pharmaceutically acceptable excipient", means that the excipient is suitable for use with humans and/or animals without undue adverse side effects (such as toxicity, irritation, and allergic response) commensurate with a reasonable benefit/risk ratio.

Phosphoramidite: As used herein, the term "phosphoramidite" refers to a nitrogen containing trivalent phosphorus derivative. Examples of suitable phosphoramidites are described herein.

Potency: As used herein, "potency" refers to the amount of an oligonucleotide or other drug that must be administered in vivo or in vitro to obtain a particular level of activity against an intended target in cells. For example, an oligonucleotide that suppresses the expression of its target by 90% in a subject at a dosage of 1 mg/kg has a greater potency than an oligonucleotide that suppresses the expression of its target by 90% in a subject at a dosage of 100 mg/kg.

Protecting group: As used herein, the term "protecting group" is used in the conventional chemical sense as a group which reversibly renders unreactive a functional group under certain conditions of a desired reaction. After the desired reaction, protecting groups may be removed to deprotect the protected functional group. All protecting groups should be removable under conditions which do not degrade a substantial proportion of the molecules being synthesized.

Ribonucleotide: As used herein, the term "ribonucleotide" refers to a natural or modified nucleotide which has a hydroxyl group at the 2'-position of the sugar moiety.

Ribozyme: As used herein, the term "ribozyme" refers to a catalytic nucleic acid molecule that specifically recognizes and cleaves a distinct target nucleic acid sequence, which can be either DNA or RNA. Each ribozyme has a catalytic component (also referred to as a "catalytic domain") and a target sequence-binding component consisting of two binding domains, one on either side of the catalytic domain.

RNAi inhibitor molecule: As used herein, the term "RNAi inhibitor molecule" refers to either (a) a double stranded nucleic acid inhibitor molecule ("dsRNAi inhibitor molecule") having a sense strand (passenger) and antisense strand (guide), where the antisense strand or part of the antisense strand is used by the Argonaute 2 (Ago2) endonuclease in the cleavage of a target mRNA or (b) a single stranded nucleic acid inhibitor molecule ("ssRNAi inhibitor molecule") having a single antisense strand, where that antisense strand (or part of that antisense strand) is used by the Ago2 endonuclease in the cleavage of a target mRNA.

Sense strand: A double stranded RNAi inhibitor molecule comprises two oligonucleotide strands: an antisense strand and a sense strand. The sense strand or a region thereof is partially, substantially or fully complementary to the antisense strand of the double stranded RNAi inhibitor molecule or a region thereof. In certain embodiments, the sense strand may also contain nucleotides that are non-complementary to the antisense strand. The non-complementary nucleotides may be on either side of the complementary sequence or may be on both sides of the complementary sequence. In certain embodiments, where the sense strand or a region thereof is partially or substantially complementary to the antisense strand or a region thereof, the non-complementary nucleotides may be located between one or more regions of complementarity (e.g., one or more mismatches). The sense strand is also called the passenger strand.

Substituent or substituted: The terms "substituent" or "substituted" as used herein refer to the replacement of hydrogen radicals in a given structure with the radical of a substituent. When more than one position in any given structure may be substituted with more than one substituent, the substituent may be either the same or different at every position unless otherwise indicated. As used herein, the term "substituted" is contemplated to include all permissible substituents that are compatible with organic compounds. The permissible substituents include acyclic and cyclic, branched and unbranched, carbocyclic and heterocyclic, aromatic and nonaromatic substituents of organic compounds. This disclosure is not intended to be limited in any manner by the permissible substituents of organic compounds.

Sulfonyl group: As used herein, the term "sulfonyl group" refers to a chemical compound containing the bivalent group, —$SO_2$—. In certain embodiments, the sulfur atom is covalently bound to two carbon atoms and two oxygen atoms. In other embodiments, the sulfur atom is covalently bound to a carbon atom, a nitrogen atom, and two oxygen atoms.

Systemic administration: As used herein, the term "systemic administration" refers to in vivo systemic absorption or accumulation of drugs in the blood stream followed by distribution throughout the entire body.

Target site: As used herein, the term "target site" "target sequence," "target nucleic acid", "target region," "target gene" are used interchangeably and refer to a RNA or DNA sequence that is "targeted," e.g., for cleavage mediated by an RNAi inhibitor molecule that contains a sequence within its guide/antisense region that is partially, substantially, or perfectly or sufficiently complementary to that target sequence.

Tetraloop: As used herein, the term "tetraloop" refers to a loop (a single stranded region) that forms a stable secondary structure that contributes to the stability of an adjacent Watson-Crick hybridized nucleotides. Without being limited to theory, a tetraloop may stabilize an adjacent Watson-Crick base pair by stacking interactions. In addition, interactions among the nucleotides in a tetraloop include but are not limited to non-Watson-Crick base pairing, stacking interactions, hydrogen bonding, and contact interactions (Cheong et al., Nature 1990; 346(6285):680-2; Heus and Pardi, Science 1991; 253(5016):191-4). A tetraloop confers an increase in the melting temperature (Tm) of an adjacent duplex that is higher than expected from a simple model loop sequence consisting of random bases. For example, a tetraloop can confer a melting temperature of at least 50° C., at least 55° C., at least 56° C., at least 58° C., at least 60° C., at least 65° C. or at least 75° C. in 10 mM NaHPO4 to a hairpin comprising a duplex of at least 2 base pairs in length. A tetraloop may contain ribonucleotides, deoxyribonucleotides, modified nucleotides, and combinations thereof. In certain embodiments, a tetraloop consists of four nucleotides. In certain embodiments, a tetraloop consists of five nucleotides.

Examples of RNA tetraloops include the UNCG family of tetraloops (e.g., UUCG), the GNRA family of tetraloops (e.g., GAAA), and the CUUG tetraloop. (Woese et al., *PNAS*, 1990, 87(21):8467-71; Antao et al., *Nucleic Acids Res.*, 1991, 19(21):5901-5).

Examples of DNA tetraloops include the d(GNNA) family of tetraloops (e.g., d(GTTA), the d(GNRA)) family of tetraloops, the d(GNAB) family of tetraloops, the d(CNNG) family of tetraloops, and the d(TNCG) family of tetraloops (e.g., d(TTCG)). (Nakano et al. *Biochemistry*, 2002, 41(48): 14281-14292. Shinji et al., *Nippon Kagakkai Koen Yokoshu*, 2000, 78(2):731).

I. Introduction

This application provides phosphate analog-modified oligonucleotides, such as nucleic acid inhibitor molecules. The 5'-terminal nucleotide of an oligonucleotide of interest is modified with a phosphate-containing moiety as described herein. The present modifications are particularly suitable for in vivo use since they can help protect the oligonucleotides against phosphatases and/or nucleases, e.g., exonucleases, which are present in the blood and/or within cells, e.g., the endosomal/lysosomal compartments of cells. Typically, the phosphate analog-modified oligonucleotide is a nucleic acid inhibitor molecule, such as a dsRNAi inhibitor molecule, an antisense oligonucleotide, ribozymes, aptamers, miRNA, and ssRNAi inhibitor molecules.

Also provided are phosphate analog-modified nucleosides comprising a phosphoramidite moiety that may be used to synthesize an oligonucleotide with a 5'-terminal nucleotide that contains a phosphate analog according to the present disclosure.

II. Phosphate Analog-Modified Oligonucleotides

One aspect is directed to an oligonucleotide, such as a nucleic acid inhibitor molecule, wherein the oligonucleotide comprises a 4'-phosphate analog, typically at the 5'-terminal nucleotide. Typically, the 4'-phosphate analog is an oxymethylphosphonate, where the oxygen atom of the oxymethyl group is bound to the 4'-carbon of the sugar moiety or analog thereof. In other embodiments, the phosphate analog is a thiomethylphosphonate or an aminomethylphosphonate, where the sulfur atom of the thiomethyl group or the nitrogen atom of the aminomethyl group is bound to the 4'-carbon of the sugar moiety or analog thereof.

In certain embodiments, the 4'-phosphate analog is an oxymethylphosphonate. Typically, the oxymethylphosphonate is represented by —O—CH$_2$—PO(OH)$_2$ or —O—CH$_2$—PO(OR)$_2$, where R is independently selected from H, CH$_3$, an alkyl group, CH$_2$CH$_2$CN, CH$_2$OCOC(CH$_3$)$_3$, CH$_2$OCH$_2$CH$_2$Si(CH$_3$)$_3$, or a protecting group. In certain embodiments, the alkyl group is CH$_2$CH$_3$. More typically, R is independently selected from H, CH$_3$, or CH$_2$CH$_3$.

1. Formulas I and II

In some embodiments, the oligonucleotide comprises a 5'-terminal nucleotide represented by Formula I or Formula II:

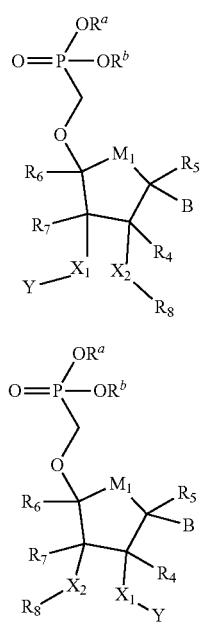

wherein $R^a$ and $R^b$ is each independently selected from hydrogen, CH$_3$, CH$_2$CH$_3$, CH$_2$CH$_2$CN, CH$_2$OCOC(CH$_3$)$_3$, CH$_2$OCH$_2$CH$_2$Si(CH$_3$)$_3$, or a protecting group;

wherein B is a natural nucleobase, a modified nucleobase, a universal base or absent;

wherein $M_1$ is O, S, NR', CR'R";

wherein $R_4$, $R_5$, $R_6$, or $R_7$ is each independently selected from hydrogen, halogen, OH, C$_1$-C$_6$ alkyl, C$_1$-C$_6$ haloalkyl or wherein two of $R_4$, $R_5$, $R_6$ and $R_7$ are taken together to form a 5-8 membered ring, wherein the ring optionally contains a heteroatom;

wherein $X_1$ is absent or selected from O, S, NR', or CR'R";

wherein Y is an internucleotide linking group attaching the 5'-terminal nucleotide to an oligonucleotide;

wherein $R_8$ is a glutathione-sensitive moiety or absent;

wherein if $R_8$ is a glutathione-sensitive moiety, $X_2$ is O, S, Se, or NR', or if $R_8$ is absent, $X_2$ is H, OH, SH, NH$_2$, halogen, optionally substituted alkoxy, optionally substituted alkyl, optionally substituted alkenyl, optionally substituted alkynyl, optionally substituted alkylthio, optionally substituted alkylamino or dialkylamino wherein one or more methylenes in the alkyl, alkenyl, and alkynyl may be interrupted with one or more of O, S, S(O), SO$_2$, N(R'), C(O), N(R')C(O)O, OC(O)N(R') optionally substituted aryl, optionally substituted heteroaryl, optionally substituted heterocyclic or optionally substituted cycloalkyl, O, S, Se or NHR'; and wherein R' and R" are each independently hydrogen, a halogen, a substituted or unsubstituted aliphatic, a substituted or unsubstituted aryl, a substituted or unsubstituted heteroaryl, a substituted or unsubstituted heterocycle or a substituted or unsubstituted cycloalkyl.

In certain embodiments, the 5'-terminal nucleotide is represented by Formula I.

In certain embodiments, the 5'-terminal nucleotide is represented by Formula II.

In certain embodiments, B is a natural nucleobase.

In certain embodiments, $M_1$ is O.

In certain embodiments, the halogen is a fluorine.

In certain embodiments, $R_4$, $R_5$, $R_6$ and $R_7$ are independently selected from hydrogen, a fluorine, CH$_3$, or C$_1$-C$_6$ alkyl. Typically, $R_4$, $R_5$, $R_6$ and $R_7$ are hydrogen.

In certain embodiments, $X_1$ is O.

In certain embodiments, $R^a$ and $R^b$ are hydrogen. In certain embodiments, $R^a$ is CH$_3$ and $R^b$ is hydrogen. In certain embodiments, $R^a$ and $R^b$ are CH$_3$. In certain embodiments, $R^a$ is CH$_2$CH$_3$ and $R^b$ is hydrogen. In certain embodiments, $R^a$ and $R^b$ are CH$_2$CH$_3$.

In certain embodiments, $M_1$ is O, $X_2$ is O and $R_4$, $R_5$, $R_6$ and $R_7$ are hydrogen.

In certain embodiments, $X_2$ is O, S, Se or NHR', wherein R' is selected from hydrogen, halogen, a substituted or unsubstituted aliphatic, a substituted or unsubstituted aryl, a substituted or unsubstituted heteroaryl, a substituted or unsubstituted heterocycle or a substituted or unsubstituted cycloalkyl and $R_8$ is a glutathione sensitive moiety. Typically, $X_2$ is O and $R_8$ is a glutathione sensitive moiety and the 5'-terminal nucleotide is represented by Formula I.

In certain embodiments, $X_2$ is halogen or an optionally substituted alkoxy and $R_8$ is absent. Typically, $X_2$ is F, OCH$_2$CH$_2$OCH$_3$ or OCH$_3$ and $R_8$ is absent and the 5'-terminal nucleotide is represented by Formula I.

In certain embodiments, $M_1$ is O, $X_2$ is O, $R_4$, $R_5$, $R_6$ and $R_7$ are hydrogen, B is a natural nucleobase; $X_1$ is absent or O, and the 5'-terminal nucleotide is represented by Formula I.

2. Formula III

In certain embodiments, the oligonucleotide comprises a 5'-terminal nucleotide represented by Formula III:

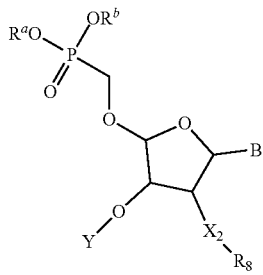

III wherein $R^a$ and $R^b$ is each independently selected from hydrogen, $CH_3$, $CH_2CH_3$, $CH_2CH_2CN$, $CH_2OCOC(CH_3)_3$, $CH_2OCH_2CH_2Si(CH_3)_3$, or a protecting group;

wherein B is a natural nucleobase, a modified nucleobase, a universal base or absent;

wherein Y is an internucleotide linking group attaching the 5'-terminal nucleotide to an oligonucleotide; and wherein $X_2$ is OH, F, $OCH_3$, or $OCH_2CH_2OCH_3$ and $R_8$ is absent or wherein $X_2$ is O and $R_8$ is a glutathione sensitive moiety.

In certain embodiments, B is a natural nucleobase.

In certain embodiments, $R^a$ and $R^b$ is each independently selected from hydrogen, $CH_3$, and $CH_2CH_3$.

In certain embodiments, $X_2$ is F or $OCH_3$ and $R_8$ is absent.

In certain embodiments, $X_2$ is O and $R_8$ is a glutathione sensitive moiety.

In certain embodiments, $R^a$ and $R^b$ are hydrogen, $R_8$ is absent, and $X_2$ is F or $OCH_3$.

In certain embodiments, $R^a$ is $CH_3$, $R^b$ is hydrogen, $R_8$ is absent, and $X_2$ is F or $OCH_3$.

In certain embodiments, $R^a$ and $R^b$ are $CH_3$, $R_8$ is absent, and $X_2$ is F or $OCH_3$.

In certain embodiments, $R^a$ is $CH_2CH_3$, $R^b$ is hydrogen, $R_8$ is absent, and $X_2$ is F or $OCH_3$.

In certain embodiments, $R^a$ and $R^b$ are $CH_2CH_3$, $R_8$ is absent, and $X_2$ is F or $OCH_3$.

3. Formula IV

In certain embodiments, the oligonucleotide comprises a 5'-terminal nucleotide represented by Formula IV:

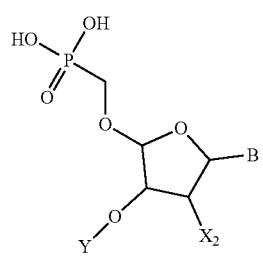

IV wherein B is a natural nucleobase, a modified nucleobase, a universal base or absent;

wherein Y is an internucleotide linking group attaching the 5'-terminal nucleotide to an oligonucleotide; and wherein $X_2$ is OH, F, $OCH_3$, or $OCH_2CH_2OCH_3$.

In certain embodiments, B is a natural nucleobase.

In certain embodiments, $X_2$ is F or $OCH_3$.

4. Formula V

In certain embodiments, the oligonucleotide comprises a 5'-terminal nucleotide represented by Formula V:

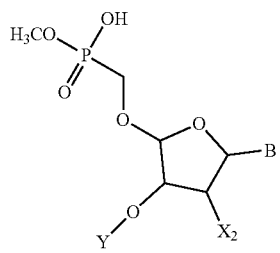

V wherein B is a natural nucleobase, a modified nucleobase, a universal base or absent;

wherein Y is an internucleotide linking group attaching the 5'-terminal nucleotide to an oligonucleotide; and wherein $X_2$ is OH, F, $OCH_3$, or $OCH_2CH_2OCH_3$.

In certain embodiments, B is a natural nucleobase.

In certain embodiments, $X_2$ is F or $OCH_3$.

5. Formula VI

In one embodiment, the oligonucleotide comprises a 5'-terminal nucleotide, wherein the 5'-terminal nucleotide is represented by Formula VI:

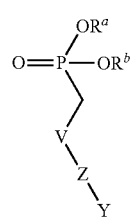

VI wherein $R^a$ and $R^b$ is each independently selected from hydrogen, $CH_3$, $CH_2CH_3$, $CH_2CH_2CN$, $CH_2OCOC(CH_3)_3$, $CH_2OCH_2CH_2Si(CH_3)_3$, or a protecting group;

wherein V is O;

wherein Z is a nucleoside comprising a sugar moiety;

wherein Y is an internucleotide linking group attaching the 5'-terminal nucleotide to an oligonucleotide; and wherein V is bound to the 4'-carbon of the sugar moiety.

Typically, the sugar moiety is a furanose and V is bound to the 4'-carbon of the furanose.

In certain embodiments, $R^a$ and $R^b$ are hydrogen. In certain embodiments, $R^a$ is $CH_3$ and $R^b$ is hydrogen. In certain embodiments, $R^a$ and $R^b$ are $CH_3$. In certain embodiments, $R^a$ is $CH_2CH_3$ and $R^b$ is hydrogen. In certain embodiments, $R^a$ and $R^b$ are $CH_2CH_3$.

6. Formula VII

In one embodiment, the oligonucleotide comprises a 5'-terminal nucleotide, wherein the 5'-terminal nucleotide is represented by Formula VII:

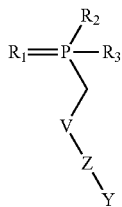

VII wherein $R_1$ is O or S;

wherein $R_2$ and $R_3$ is each independently selected from OH, SH, $NH_2$, $OCH_3$, $OR_9$, $OCH_2CH_2CN$, $OCH_2OCOC(CH_3)_3$, and $OCH_2OCH_2CH_2Si(CH_3)_3$, wherein $R_9$ is alkyl, and wherein OH, SH, and $NH_2$ are optionally protected with a protecting group;

wherein V is O, S, NR', CR'R", wherein R' and R" are each independently hydrogen, halogen, a substituted or unsubstituted aliphatic, a substituted or unsubstituted aryl, a substituted or unsubstituted heteroaryl, a substituted or unsubstituted heterocycle or a substituted or unsubstituted cycloalkyl;

wherein Z is a nucleoside comprising a sugar moiety;

wherein Y is an internucleotide linking group attaching the 5'-terminal nucleotide to an oligonucleotide; and wherein V is bound to the 4'-carbon of the sugar moiety.

Typically, the sugar moiety is a furanose and V is bound to the 4'-carbon of the furanose.

In certain embodiments $R_2$ or $R_3$ is each independently selected from OH, $OCH_3$, or $OR_9$, wherein $R_9$ is $C_1$-$C_6$ alkyl. In certain embodiments, $R_9$ is $CH_2CH_3$.

Typically, $R_1$ is O.

In certain embodiments, $R_1$ is O; $R_2$ is OH, $OCH_3$, or $OCH_2CH_3$; and $R_3$ is OH, $OCH_3$, or $OCH_2CH_3$. In certain embodiments, $R_1$ is O; $R_2$ is OH; and $R_3$ is OH. In certain embodiments, $R_1$ is O; $R_2$ is $OCH_3$ or $OCH_2CH_3$; and $R_3$ is OH. In certain embodiments, $R_1$ is O; $R_2$ is $OCH_3$; and $R_3$ is OH. In certain embodiments, $R_1$ is O and $R_2$ and $R_3$ are $OCH_3$. In certain embodiments, $R_1$ is O; $R_2$ is $OCH_2CH_3$; and $R_3$ is OH. In certain embodiments, $R_1$ is O and $R_2$ and $R_3$ are O $CH_2CH_3$.

7. Formulas VIII or IX

In some embodiments, the disclosure provides an oligonucleotide comprising a 5'-terminal nucleotide represented by Formula VIII or Formula IX:

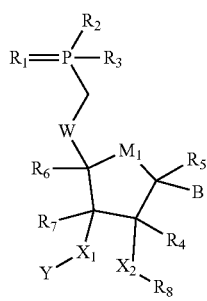

VIII

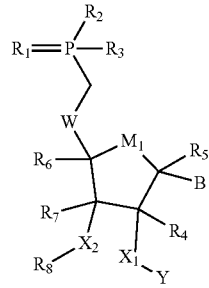

IX wherein $R_1$ is O or S;

wherein $R_2$ and $R_3$ is each independently selected from OH, SH, $NH_2$, $OCH_3$, $OR_9$, $OCH_2CH_2CN$, $OCH_2OCOC(CH_3)_3$, and $OCH_2OCH_2CH_2Si(CH_3)_3$, wherein $R_9$ is alkyl, and wherein OH, SH, and $NH_2$ are optionally protected;

wherein W is N or S; and wherein B, $M_1$, $R_4$, $R_5$, $R_6$, $R_7$, $R_8$, $X_1$, $X_2$, and Y are as described in Formula I or II.

In certain embodiments, W is N.
In certain embodiments, W is S.
In certain embodiments, $R_1$ is O.
In certain embodiments $R_2$ or $R_3$ is each independently selected from OH, $OCH_3$, or $OR_9$, wherein $R_9$ is $C_1$-$C_6$ alkyl. In certain embodiments, $R_9$ is $CH_2CH_3$.

Typically, $R_1$ is O.

The oligonucleotides comprising the 4'-phosphate analog as described herein can comprise any nucleotide sequence of interest. In certain embodiments, the oligonucleotide of Formula I-IX has 7-100 nucleotides. In another embodiment, the oligonucleotide of Formula I-IX has 15-50 nucleotides. In another embodiment, the oligonucleotide of Formula I-IX has 25-40 nucleotides. In yet another embodiment, the oligonucleotide of Formula I-IX has 19-25 nucleotides.

A. Nucleic Acid Inhibitor Molecules

In certain embodiments, the oligonucleotides comprising the 4'-phosphate analog are nucleic acid inhibitor molecules. Various oligonucleotide structures have been used as nucleic acid inhibitor molecules, including single stranded and double stranded oligonucleotides, and any of these various oligonucleotides can be modified to include a 4'-phosphate analog-modified nucleotide as described herein, including the 5'-terminal nucleotide of any one of Formulas I-IX.

Double-Stranded Nucleic Acid Inhibitor Molecules

In some embodiments, the nucleic acid inhibitor molecules described herein are double-stranded RNAi inhibitor molecules having a sense (or passenger) strand and an antisense (or guide) strand and comprising at least one nucleotide having a 4'-phosphate analog, as described herein. As discussed above, a variety of double stranded RNAi inhibitor molecule structures are known in the art, including for example: (a) double-stranded nucleic acid molecules with each strand having sizes of 19-25 nucleotides with at least one 3'-overhang of 1 to 5 nucleotides (see, e.g., U.S. Pat. No. 8,372,968); (b) longer double-stranded RNAi inhibitor molecules that get processed in vivo by the Dicer enzyme to active RNAi inhibitor molecules (see, e.g., U.S. Pat. No. 8,883,996); and (c) double-stranded nucleic acid inhibitor molecules where at least one end of at least one strand is extended beyond the double-stranded targeting region of the molecule, including structures where one of the strands includes a thermodynamically-stabilizing tetraloop structure (see, e.g., U.S. Pat. Nos. 8,513,207, 8,927,705, WO 2010/033225, and WO 2016/100401, which are incorporated by reference for their disclosure of these double-stranded nucleic acid inhibitor molecules).

In some embodiments of the dsRNAi inhibitor molecule, the sense and antisense strands range from 15-66, 25-40, or 19-25 nucleotides. In some embodiments, the sense strand is between 18 and 66 nucleotides in length. In certain embodiments, the sense strand is between 18 and 25 nucleotides in length. In certain embodiments, the sense strand is 18, 19, 20, 21, 22, 23, or 24 nucleotides in length. In certain of those embodiments, the sense strand is between 25 and 45 nucleotides in length. In certain embodiments, the sense strand is between 30 and 40 nucleotides in length. In certain embodiments, the sense strand is 36, 37, 38, 39, or 40 nucleotides in length. In certain embodiments, the sense strand is between 25 and 30 nucleotides in length. In certain of those embodiments, the sense strand is 25, 26, or 27 nucleotides in length.

In some embodiments of the dsRNAi inhibitor molecule, the antisense strand is between 18 and 66 nucleotides in length. Typically, the antisense strand comprises a sequence that is sufficiently complementary to a sequence in the target gene mRNA to direct the effect of the nucleic acid inhibitor molecule to the target gene. In certain embodiments, the antisense strand comprises a sequence that is fully complementary with a sequence contained in the target gene mRNA where the fully complementary sequence is between 18 and 40 nucleotides long. In certain of those embodiments, the antisense strand is between 20 and 50 nucleotides in length. In certain embodiments, the antisense strand is between 20 and 30 nucleotides in length. In certain embodiments, the antisense strand is 21, 22, 23, 24, 25, 26, 27, or 28 nucleotides in length. In certain embodiments, the antisense strand is between 35 and 40 nucleotides in length. In certain of those embodiments, the antisense strand is 36, 37, 38, or 39 nucleotides in length.

In some embodiments of the dsRNAi inhibitor molecule, the sense and antisense strands form a duplex structure having between 15 and 50 base pairs. In certain embodiments, the duplex region is between 15 and 45 base pairs in length, more typically between 15 and 30 base pairs in length, such as between 18 and 30, more typically between 18 and 26 or 21 and 26, such as between 19 and 23, and in certain instances, between 19 and 21 base pairs in length. In certain embodiments, the double-stranded region is 19, 20, 21, 22, 23, 24, 25, or 26 base pairs in length.

In some embodiments, the dsRNAi inhibitor molecule may further comprise one or more single-stranded nucleotide overhang(s). Typically, the dsRNAi inhibitor molecule has a single-stranded overhang of 1-10, 1-4, or 1-2 nucleotides. The single stranded overhang is typically located at the 3'-end of the sense strand and/or the 3'-end of the antisense strand. In certain embodiments, a single-stranded overhang of 1-10, 1-4, or 1-2 nucleotides is located at the 5'-end of the antisense strand. In certain embodiments, a single-stranded overhang of 1-10, 1-4, or 1-2 nucleotides is located at the 5'-end of the sense strand. In certain embodiments, the single-stranded overhang of 1-2 nucleotides is located at the 3'-end of the antisense strand. In certain embodiments, the single-stranded overhang of 10 nucleotides is located at the 5'-end of the antisense strand. In certain embodiments, the dsRNAi inhibitor molecule has a blunt end, typically at the 5'-end of the antisense strand.

In some embodiments, the dsRNAi inhibitor molecule comprises a sense and an antisense strand and a duplex region of between 19-21 nucleotides, wherein the sense strand is 19-21 nucleotides in length and the antisense strand is 21-23 nucleotides in length and comprises a single-stranded overhang of 1-2 nucleotides at its 3'-terminus.

In certain embodiments, the dsRNAi inhibitor molecule has an antisense strand of 21 nucleotides in length and a sense strand of 21 nucleotides in length, where there is a two nucleotide 3'-sense strand overhang on the right side of the molecule (3'-end of sense strand/5'-end of antisense strand) and a single-stranded overhang of two nucleotides oat the 3'-end of the antisense strand. In such molecules, there is a 19 base pair duplex region.

In certain embodiments, the dsRNAi inhibitor molecule has an antisense strand of 23 nucleotides in length and a sense strand of 21 nucleotides in length, where there is a blunt end on the right side of the molecule (3'-end of sense strand/5'-end of antisense strand) and a two nucleotide 3'-sense strand overhang on the left side of the molecule (5'-end of the sense strand/3'-end of the antisense strand). In such molecules, there is a 21 base pair duplex region.

In certain embodiments, the dsRNAi inhibitor molecule comprises a sense and an antisense strand and a duplex region of between 18-34 nucleotides, where the sense strand is 25-34 nucleotides in length and the antisense strand is 26-38 nucleotides in length and comprises 1-5 single-stranded nucleotides at its 3' terminus. In certain embodiments, the sense strand is 26 nucleotides, the antisense strand is 38 nucleotides and has a single-stranded overhang of 2 nucleotides at its 3' terminus and a single-stranded overhang of 10 nucleotides at its 5' terminus, and the sense strand and antisense strand form a duplex region of 26 nucleotides. In certain embodiments, the sense strand is 25 nucleotides, the antisense strand is 27 nucleotides and has a single-stranded overhang of 2 nucleotides at its 3' terminus, and the sense strand and antisense strand form a duplex region of 25 nucleotides.

In some embodiments, the dsRNAi inhibitor molecules include a stem and loop. Typically, a 3'-terminal region or 5'-terminal region of a passenger strand of a dsRNAi inhibitor molecule form a stem and loop structure.

In some embodiments, the dsRNAi inhibitor molecule contains a stem and tetraloop. In embodiments where the dsRNAi inhibitor molecule contains a stem and tetraloop, the passenger strand contains the stem and tetraloop and ranges from 20-66 nucleotides in length. Typically, the guide and passenger strands are separate strands, each having a 5' and 3' end that do not form a contiguous oligonucleotide (sometimes referred to as a "nicked" structure).

In certain of those embodiments, the guide strand is between 15 and 40 nucleotides in length. In certain embodiments, the extended part of the passenger strand that contains the stem and tetraloop is on the 3'-end of the strand. In certain other embodiments, the extended part of the passenger strand that contains the stem and tetraloop is on the 5'-end of the strand.

In certain embodiments, the passenger strand of a dsRNAi inhibitor molecule containing a stem and tetraloop is between 34 and 40 nucleotides in length and the guide strand of the dsRNAi inhibitor molecule contains between 20 and 24 nucleotides, where the passenger strand and guide strand form a duplex region of 18-24 nucleotides.

In certain embodiments, the dsRNAi inhibitor molecule comprises (a) a passenger strand that contains a stem and tetraloop and is 36 nucleotides in length, wherein the first 20 nucleotides from the 5'-end are complementary to the guide strand and the following 16 nucleotides form the stem and tetraloop and (b) a guide strand that is 22 nucleotides in length and has a single-stranded overhang of two nucleotides at its 3' end, wherein the guide and passenger strands are separate strands that do not form a contiguous oligonucleotide (see e.g., FIGS. 1A-1D).

In certain embodiments, the dsRNAi inhibitor molecule includes one or more deoxyribonucleotides. Typically, the dsRNAi inhibitor molecule contains fewer than 5 deoxyribonucleotides. In certain embodiments, the dsRNAi inhibitor molecule includes one or more ribonucleotides. In certain embodiments, all of the nucleotides of the dsRNAi inhibitor molecule are ribonucleotides.

In some embodiments, the 5'-terminal nucleotide of any one of Formulas I-IX is located on the passenger strand of a double-stranded nucleic acid inhibitor molecule, e.g., a dsRNAi inhibitor molecule. In another embodiment, the 5'-terminal nucleotide of any one of Formulas I-IX is located on the guide strand. In another embodiment, the 5'-terminal nucleotide of any one of Formulas I-IX is located on both the guide strand and the passenger strand. In one embodiment, the 5'-terminal nucleotide of any one of Formulas I-IX is located in a duplex region. In some embodiments, the 5'-terminal nucleotide of any one of Formulas I-IX is located in an overhang region.

Single-Stranded Nucleic Acid Inhibitor Molecules

In certain embodiments, the nucleic acid inhibitor molecule is a single-stranded nucleic acid inhibitor molecule comprising a 5'-terminal nucleotide according to of any one of Formulas I-IX. Single stranded nucleic acid inhibitor molecules are known in the art. For example, recent efforts have demonstrated activity of ssRNAi inhibitor molecules (see, e.g., Matsui et al., *Molecular Therapy*, 2016,24(5):946-55. And, antisense molecules have been used for decades to reduce expression of specific target genes. Pelechano and Steinmetz, *Nature Review Genetics*, 2013,14:880-93. A number of variations on the common themes of these structures have been developed for a range of targets. Single-stranded nucleic acid inhibitor molecules include, for example, conventional antisense oligonucleotides, microRNA, ribozymes, aptamers, antagomirs, and ssRNAi inhibitor molecules, all of which are known in the art.

In certain embodiments, the nucleic acid inhibitor molecule is a ssRNAi inhibitor molecule having 14-50, 16-30, or 15-25 nucleotides. In other embodiments, the ssRNAi inhibitor molecule has 18-22 or 20-22 nucleotides. In certain embodiments, the ssRNAi inhibitor molecule has 20 nucleotides. In other embodiments, the ssRNAi inhibitor molecule has 22 nucleotides.

In certain embodiments, the nucleic acid inhibitor molecule is a single-stranded oligonucleotide that inhibits exogenous RNAi inhibitor molecules or natural miRNAs. In certain embodiments, the nucleic acid inhibitor molecule is a single-stranded antisense oligonucleotide having 8-80, 14-50, 16-30, 12-25, 12-22, 14-20, 18-22, or 20-22 nucleotides. In certain embodiments, the single-stranded antisense oligonucleotide has 18-22, such as 18-20 nucleotides.

In certain embodiments, the antisense oligonucleotide or a portion thereof is fully complementary to a target nucleic acid or a specific portion thereof. In certain embodiments, the antisense oligonucleotide or a portion thereof is complementary to at least 12, 13, 14, 15, 16, 17, 18, 19, 20, or more contiguous nucleotides of the target nucleic acid. In certain embodiments, the antisense oligonucleotide contains no more than 5, 4, 3, 2, or 1 non-complementary nucleotides relative to the target nucleic acid or portion thereof. It is possible to decrease the length of the antisense oligonucleotide and/or introduce mismatch bases without eliminating activity B. Nucleotide Modifications The modified oligonucleotides of the present disclosure may include modifications in addition to the 4'-phosphate analogs described herein. Typically, multiple nucleotide subunits of the nucleic acid inhibitor molecule are modified to improve various characteristics of the molecule such as resistance to nucleases or lowered immunogenicity. See, e.g., Bramsen et al. (2009), Nucleic Acids Res., 37, 2867-2881. Many nucleotide modifications have been used in the oligonucleotide field, particularly for nucleic acid inhibitor molecules. Such modifications can be made on any part of the nucleotide, including the sugar moiety, the phosphoester linkage, and the nucleobase. In certain embodiments of the nucleic acid inhibitor molecule, from one to every nucleotide is modified at the 2'-carbon of the sugar moiety, using, for example, 2'-carbon modifications known in the art and described herein. Typical examples of 2'-carbon modifications include, but are not limited to, 2'-F, 2'-O-methyl ("2'-OMe" or "2'-OCH$_3$"), 2'-O-methoxyethyl ("2'-MOE" or "2'-OCH$_2$CH$_2$OCH$_3$"). Modifications can also occur at other parts of the sugar moiety of the nucleotide, such as the 5'-carbon, as described herein.

In certain embodiments, the ring structure of the sugar moiety is modified, including, but not limited to, Locked Nucleic Acid ("LNA") structures, Bridged Nucleic Acid ("BNA") structures, and Unlocked Nucleic Acid ("UNA") structures, as discussed previously.

Modified nucleobases include nucleobases other than adenine, guanine, cytosine, thymine and uracil at the 1'-position, as known in the art and as described herein. A typical example of a modified nucleobase is 5'-methylcytosine.

The natural occurring internucleotide linkage of RNA and DNA is a 3' to 5' phosphodiester linkage. Modified phosphodiester linkages include non-naturally occurring internucleotide linking groups, including internucleotide linkages that contain a phosphorous atom and internucleotide linkages that do not contain a phosphorous atom, as known in the art and as described herein. Typically, the nucleic acid inhibitor molecule contains one or more phosphorous-containing internucleotide linking groups, as described herein. In other embodiments, one or more of the internucleotide linking groups of the nucleic acid inhibitor molecule is a non-phosphorus containing linkage, as described herein. In certain embodiments, the nucleic acid inhibitor molecule contains one or more phosphorous-containing internucleotide linking groups and one or more non-phosphorous containing internucleotide linking groups.

In certain embodiments one or two nucleotides of a nucleic acid inhibitor molecule are reversibly modified with a glutathione-sensitive moiety. Typically, the glutathione-sensitive moiety is located at the 2'-carbon of the sugar moiety and comprises a sulfonyl group or a disulfide bridge. In certain embodiment, the glutathione-sensitive moiety is compatible with phosphoramidite oligonucleotide synthesis methods, as described, for example, in International Patent Application No. PCT/US2017/048239, which is hereby incorporated by reference in its entirety. In certain embodiments, more than two nucleotides of a nucleic acid inhibitor molecule are reversibly modified with a glutathione-sensitive moiety. In certain embodiments, most of the nucleotides are reversibly modified with a glutathione-sensitive moiety. In certain embodiments, all or substantially all the nucleotides of a nucleic acid inhibitor molecule are reversibly modified with a glutathione-sensitive moiety.

The at least one glutathione-sensitive moiety is typically located at the 5'- or 3'-terminal nucleotide of a single-stranded nucleic acid inhibitor molecule or the 5'- or 3'-terminal nucleotide of the passenger strand or the guide strand of a double-stranded nucleic acid inhibitor molecule. However, the at least one glutathione-sensitive moiety may be located at any nucleotide of interest in the nucleic acid inhibitor molecule.

In certain embodiments, a nucleic acid inhibitor molecule is fully modified, wherein every nucleotide of the fully modified nucleic acid inhibitor molecule is modified. In certain embodiments, the fully modified nucleic acid inhibitor molecule does not contain a reversible modification. In some embodiments, at least one, such as at least two, three, four, five, six, seven, eight, nine, 10, 11, 12, 13, 14, 15, 16, 17, 18, 19, or 20 nucleotides of a single stranded nucleic acid inhibitor molecule or the guide strand or passenger strand of a double stranded nucleic acid inhibitor molecule are modified.

In certain embodiments, the fully modified nucleic acid inhibitor molecule is modified with one or more reversible, glutathione-sensitive moieties. In certain embodiments, substantially all of the nucleotides of a nucleic acid inhibitor molecule are modified. In certain embodiments, more than half of the nucleotides of a nucleic acid inhibitor molecule are modified with a chemical modification other than a reversible modification. In certain embodiments, less than half of the nucleotides of a nucleic acid inhibitor molecule are modified with a chemical modification other than a reversible modification. Modifications can occur in groups on the nucleic acid inhibitor molecule or different modified nucleotides can be interspersed.

In certain embodiments of the nucleic acid inhibitor molecule, from one to every nucleotide is modified at the 2'-carbon. In certain embodiments, the nucleic acid inhibitor molecule (or the sense strand and/or antisense strand thereof) is partially or fully modified at the 2'-carbon, using, for example, 2'-carbon modifications known in the art and described herein. In certain embodiments of the nucleic acid inhibitor molecule, from one to every phosphorous atom is modified and from one to every nucleotide is modified at the 2'-carbon. In certain embodiments, the modification at the 2' carbon is one or more of 2'-F, 2'-OMe and/or 2'-MOE. In certain embodiments, the modification at the 2'-carbon is 2'-F and/or 2'-OMe (i.e., the single-stranded oligonucleotide or the sense and/or antisense strand of a double-stranded oligonucleotide) is partially or fully modified with 2'-F and/or 2'-OMe. In certain embodiments, the single stranded oligonucleotide contains one or more nucleotides that are reversibly modified with a glutathione-sensitive moiety.

C. Other 4'-Phosphate Analog-Modified Oligonucleotides

Although the 4'-phosphate analogs disclosed herein are typically incorporated into a nucleic acid inhibitor molecule, other nucleic acids can be modified to include a 4'-phosphate analog-modified nucleotide as described herein (e.g., the 5'-terminal nucleotide of any one of Formulas I-IX). The modified oligonucleotides of the disclosure may include any oligonucleotide of interest where the presence of a phosphate analog at the 5'-terminal nucleotide is desired. By way of example, other nucleic acids that can be modified in accordance with the teachings of this application include other therapeutic nucleic acids, such as, oligonucleotides for gene therapy or for gene editing, such as, CRISPR nucleic acid molecules. See e.g., Cong et al., *Science,* 2013, 339: 819-23; Mali et al., *Science,* 2013, 339:823-26; Woo Cho et al., *Nat. Biotechnology,* 2013, 31(3):230-232. In addition, oligonucleotides comprising the phosphate analog of the present disclosure can also be used in vitro. Such oligonucleotides include for example, a probe, a primer, a linker, an adapter or a gene fragment.

III. Nucleoside Phosphoramidites Comprising a Phosphate Analog

Another aspect of the present disclosure relates to nucleoside phosphoramidites comprising a 4'-phosphate analog, as described herein that can be used in standard oligonucleotide synthesis methods. Typically, the phosphate analog is an oxymethylphosphonate, where the oxygen atom of the oxymethyl group is bound to the 4'-carbon of the sugar moiety or analog thereof. In other embodiments, the phosphate analog is a thiomethylphosphonate or an aminomethylphosphonate, where the sulfur atom of the thiomethyl group or the nitrogen atom of the aminomethyl group is bound to the 4'-carbon of the sugar moiety or analog thereof.

In certain embodiments, the oxymethylphosphonate is represented by —O—$CH_2$—$PO(OR)_2$, where R is independently selected from $CH_3$, an alkyl group, $CH_2CH_2CN$, $CH_2OCOC(CH_3)_3$, $CH_2OCH_2CH_2Si(CH_3)_3$, or a protecting group. In certain embodiments, the alkyl group is $CH_2CH_3$. More typically, R independently selected from $CH_3$, $CH_2CH_3$, or a protecting group.

1. Formulas X and XI

In some embodiments, the nucleoside phosphoramidites of the disclosure are represented by Formula X or Formula XI:

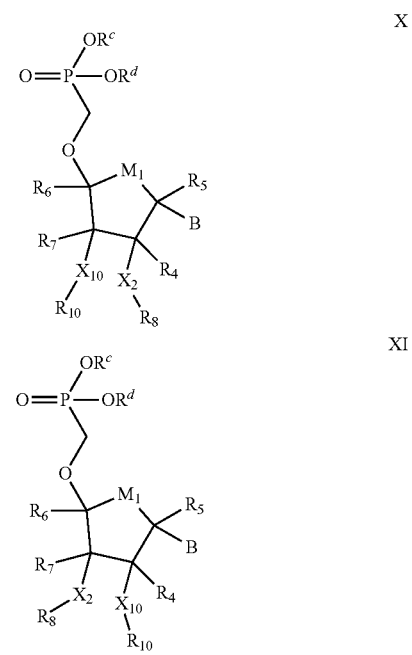

wherein B, $M_1$, $R_4$, $R_5$, $R_6$, $R_7$, $R_8$, and $X_2$, are as described in Formula I or II;

wherein $R^c$ and $R^d$ is each independently selected from $CH_3$, $CH_2CH_3$, $CH_2CH_2CN$, $CH_2OCOC(CH_3)_3$, $CH_2OCH_2CH_2Si(CH_3)_3$, or a protecting group;

wherein $X_{10}$ is absent or selected from O, S, NR', or CR'R''; and wherein $R_{10}$ is a phosphoramidite.

In certain embodiments, the phosphate analog-modified nucleoside phosphoramidite is represented by Formula X.

In certain embodiments, the phosphate analog-modified nucleoside phosphoramidite is represented by Formula XI.

In certain embodiments, B is a natural nucleobase.

In certain embodiments, $M_1$ is O.

In certain embodiments, $R_4$, $R_5$, $R_6$ and $R_7$ are independently selected from hydrogen, a fluorine, $CH_3$, or $C_1$-$C_6$ alkyl. Typically, $R_4$, $R_5$, $R_6$ and $R_7$ are hydrogen.

In certain embodiments, $X_2$ is O, a halogen, or an optionally substituted alkoxy.

In certain embodiments, $R^c$ and $R^d$ are $CH_3$. In certain embodiments, $R^c$ and $R^d$ are $CH_2CH_3$.

In certain embodiments, $M_1$ is O, $X_2$ is O and $R_4$, $R_5$, $R_6$ and $R_7$ are hydrogen.

In certain embodiments, $X_2$ is O, S, Se or NHR', wherein R' is selected from hydrogen, halogen, a substituted or unsubstituted aliphatic, a substituted or unsubstituted aryl, a substituted or unsubstituted heteroaryl, a substituted or unsubstituted heterocycle or a substituted or unsubstituted cycloalkyl and $R_8$ is a glutathione sensitive moiety. Typically, $X_2$ is O and $R_8$ is a glutathione sensitive moiety.

In certain embodiments, $X_2$ is halogen or an optionally substituted alkoxy and $R_8$ is absent. Typically, $X_2$ is F, $OCH_2CH_2OCH_3$ or $OCH_3$ and $R_8$ is absent.

In certain embodiments, $R^c$ and $R^d$ are $CH_3$, $R_8$ is absent, and $X_2$ is F or $OCH_3$.

In certain embodiments, $R^c$ and $R^d$ are $CH_2CH_3$, $R_8$ is absent, and $X_2$ is F or $OCH_3$.

In certain embodiments, the phosphoramidite has the formula —P(OR$^x$)—N(R$^y$)$_2$, wherein R$^x$ is selected from the group consisting of an optionally substituted methyl, 2-cyanoethyl and benzyl, wherein each of R$^y$ is selected from the group consisting of an optionally substituted ethyl and isopropyl.

In certain embodiments, the phosphate analog-modified nucleoside phosphoramidite is identical to Formula X or XI except that the oxygen atom that is bound to the sugar moiety of the nucleoside is replaced by a sulfur or nitrogen atom.

2. Formula XII

In some embodiments, the nucleoside phosphoramidites of the disclosure are represented by Formula XII:

XII wherein $R^c$ and $R^d$ is each independently selected from $CH_3$, $CH_2CH_3$, $CH_2CH_2CN$, $CH_2OCOC(CH_3)_3$, $CH_2OCH_2CH_2Si(CH_3)_3$, or a protecting group;

wherein B is a natural nucleobase, a modified nucleobase, a universal base or absent;

wherein $R_{10}$ is a phosphoramidite; and wherein $X_2$ is OH, F, $OCH_3$, or $OCH_2CH_2OCH_3$ and $R_8$ is absent or wherein $X_2$ is O and $R_8$ is a glutathione sensitive moiety.

In certain embodiments, B is a natural nucleobase.

In certain embodiments, $R^c$ and $R^d$ is each independently selected from $CH_3$ and $CH_2CH_3$.

In certain embodiments, $X_2$ is F or $OCH_3$ and $R_8$ is absent.

In certain embodiments, $X_2$ is O and $R_8$ is a glutathione sensitive moiety.

In certain embodiments, $R^c$ and $R^d$ are $CH_3$, $R_8$ is absent, and $X_2$ is F or $OCH_3$.

In certain embodiments, $R^c$ and $R^d$ are $CH_2CH_3$, $R_8$ is absent, and $X_2$ is F or $OCH_3$.

3. Formula XIII

In certain embodiments, the nucleoside phosphoramidite is represented by Formula XIII:

XIII wherein B is a natural nucleobase, a modified nucleobase, a universal base or absent;

wherein $R_{10}$ is a phosphoramidite; and wherein $X_2$ is OH, F, $OCH_3$, or $OCH_2CH_2OCH_3$.

In certain embodiments, B is a natural nucleobase.

In certain embodiments, $X_2$ is F or $OCH_3$.

4. Formula XIV

In certain embodiments, the nucleoside phosphoramidite is represented by Formula XIV:

XIV wherein B is a natural nucleobase, a modified nucleobase, a universal base or absent;

wherein $R_{10}$ is a phosphoramidite; and wherein $X_2$ is OH, F, $OCH_3$, or $OCH_2CH_2OCH_3$.

In certain embodiments, B is a natural nucleobase.

In certain embodiments, $X_2$ is F or $OCH_3$.

5. Formula XV

In some embodiments, the phosphate analog-modified nucleoside phosphoramidites of the disclosure are represented by Formula XV:

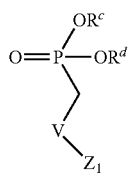

(XV)

wherein $R^c$ and $R^d$ is each independently selected from $CH_3$, $CH_2CH_3$, $CH_2CH_2CN$, $CH_2OCOC(CH_3)_3$, $CH_2OCH_2CH_2Si(CH_3)_3$, or a protecting group;

wherein V is O;

wherein $Z_1$ is a nucleoside comprising a phosphoramidite and a sugar moiety; and wherein V is bound to the 4'-carbon of the sugar moiety.

Typically, the sugar moiety is a furanose and V is bound to the 4'-carbon of the furanose.

In certain embodiments, $R^c$ and $R^d$ are $CH_3$. In certain embodiments, $R^c$ and $R^d$ are $CH_2CH_3$.

6. Formula XVI

In some embodiments, the phosphate analog-modified nucleoside phosphoramidites of the disclosure are represented by Formula XVI:

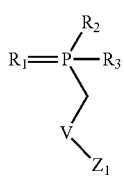

(XVI)

wherein $R_1$ is O or S;

wherein $R_2$ and $R_3$ is each independently selected from a protected OH, a protected SH, or a protected $NH_2$, $OCH_3$, $OR_9$, $OCH_2CH_2CN$, $OCH_2OCOC(CH_3)_3$, and $OCH_2OCH_2CH_2Si(CH_3)_3$, wherein $R_9$ is alkyl;

wherein V is O, S, NR', CR'R", wherein R' and R" are each independently hydrogen, halogen, a substituted or unsubstituted aliphatic, a substituted or unsubstituted aryl, a substituted or unsubstituted heteroaryl, a substituted or unsubstituted heterocycle or a substituted or unsubstituted cycloalkyl;

wherein $Z_1$ is a nucleoside comprising a phosphoramidite and a sugar moiety; and wherein V is bound to the 4'-carbon of the sugar moiety.

Typically, the sugar moiety is a furanose and V is bound to the 4'-carbon of the furanose.

Typically, V is O.

In certain embodiments $R_2$ or $R_3$ is each independently selected from a protected OH, $OCH_3$, or $OR_9$, wherein $R_9$ is $C_1$-$C_6$ alkyl. In certain embodiments, $R_9$ is $CH_2CH_3$.

Typically, $R_1$ is O.

In certain embodiments, $R_1$ is O; $R_2$ is a protected OH, $OCH_3$, or $OCH_2CH_3$; and $R_3$ is $OCH_3$ or $OCH_2CH_3$. In certain embodiments, $R_1$ is O; $R_2$ is a protected OH; and $R_3$ is a protected OH. In certain embodiments, $R_1$ is O; $R_2$ is $OCH_3$ or $OCH_2CH_3$; and $R_3$ is a protected OH. In certain embodiments, $R_1$ is O; $R_2$ is $OCH_3$; and $R_3$ is a protected OH. In certain embodiments, $R_1$ is O and $R_2$ and $R_3$ are $OCH_3$. In certain embodiments, $R_1$ is O; $R_2$ is $OCH_2CH_3$; and $R_3$ is a protected OH. In certain embodiments, $R_1$ is O and $R_2$ and $R_3$ are $OCH_2CH_3$.

Protecting Groups

In some embodiments of the 4'-phosphate analog-modified nucleoside phosphoramidites, a protecting group is attached to B, i.e., the natural, modified or universal nucleobase. Suitable protecting groups for B include acetyl, difluoroacetyl, trifluoroacetyl, isobutyryl, benzoyl, 9-fluorenylmethoxycarbonyl, phenoxyacetyl, dimethylformamidine, dibutylforamidine and N, N diphenyl carbamate.

In some embodiments, a protecting group is attached to a hydroxyl group in the nucleoside phosphoramidites described above. Suitable protecting groups for the hydroxyl groups of the above-described nucleoside phosphoramidites include any protecting group that is compatible with solid phase oligonucleotide synthesis, including, but not limited to, dimethoxytrityl, monomethoxytrityl, and/or trityl groups. A typical example is 4,4'-dimethoxytriphenylmethyl (DMTr) group, which may be readily cleaved under acidic conditions (e.g. in the presence of dichlroacetic acid (DCA), trichloroacetic acid (TCA), trifluoroacetic acid (TFA) or acetic acid).

Other typical hydroxyl protecting groups include trialkyl silyl groups, such as tertbutyldimethylsilyl (TBDMS). The TBDMS group is stable under the acidic conditions used to remove the DMT group during the synthesis cycle, but can be removed by a variety of methods after cleavage and deprotection of the RNA oligomer, e.g., with a solution of tetrabutylammonium fluoride (TBAF) in tetrahydrofurane (THF) or with triethylamine hydrofluoride. Other typical hydroxyl protecting groups include tert-butyldiphenylsilyl ether (TBDPS), which may be removed with ammonium fluoride, for example.

IV. Nucleobases

In the 4'-phosphate analog-containing oligonucleotides and nucleosides described above, B represents a natural nucleobase, a modified nucleobase or a universal nucleobase. Suitable natural nucleobases include purine and pyrimidine bases, e.g. adenine (A), thymine (T), cytosine (C), guanine (G), or uracil (U). Suitable modified nucleobases include diaminopurine and its derivatives, alkylated purines or pyrimidines, acylated purines or pyrimidines thiolated purines or pyrimidines, and the like.

Other suitable modified nucleobases include analogs of purines and pyrimidines. Suitable analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, hypoxanthine, xanthine, 2-aminopurine, 6-hydroxyaminopurine, nitropyrrolyl, nitroindolyl and difluorotolyl, 6-thiopurine and 2,6-diaminopurine nitropyrrolyl, nitroindolyl and difluorotolyl.

Typically, a nucleobase contains a nitrogenous base. In certain embodiments, the nucleobase does not contain a nitrogen atom. See e.g., U.S. Published Patent Application No. 20080274462. A universal nucleobase refers to a base that can pair with more than one of the bases typically found in naturally occurring nucleic acids and can thus substitute for such naturally occurring bases in a duplex. The base need not be capable of pairing with each of the naturally occurring bases. For example, certain bases pair only or selectively with purines, or only or selectively with pyrimidines. The universal nucleobase may base pair by forming hydrogen bonds via Watson-Crick or non-Watson-Crick interactions (e.g., Hoogsteen interactions). Representative universal nucleobases include inosine and its derivatives.

In certain embodiments, one or more nucleotides of an oligonucleotide of the invention do not have a nucleobase attached to the 1'-position of the sugar ring. Such nucleotides are referred to as abasic.

V. Other Substituents in Formulas I-XVI

In Formulas I-XVI, as appropriate, suitable aliphatic groups typically contain between about 2 and about 10 carbon atoms, more typically between about 2 and about 6 carbon atoms, such as between about 2 and about 5 carbon atoms.

In Formulas I-XVI, as appropriate, suitable alkyl groups typically contain between about 1 and about 10 carbon atoms, more typically between about 2 and about 6 carbon atoms, such as between about 2 and about 5 carbon atoms.

In Formulas I-XVI, as appropriate, suitable alkoxy groups include methoxy, ethoxy, propoxy, isopropoxy, n-butoxy, tert-butoxy, neopentoxy and n-hexoxy and the like.

In Formulas I-XVI, as appropriate, suitable cycloalkyls include cyclopropyl, cyclobutyl, cyclopentyl, cyclohexyl, cycloheptyl and the like.

In Formulas I-XVI, as appropriate, suitable heteroatoms include oxygen, sulfur, and nitrogen. Representative heterocycles include pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. Representative heteroaryls include furanyl, thienyl, pyridyl, pyrrolyl, N-lower alkyl pyrrolo, pyrimidyl, pyrazinyl, imidazolyl.

In Formulas I-XVI, as appropriate, suitable alkenyl groups include vinyl, allyl, and 2-methyl-3-heptene and suitable alkynyl groups include propyne, and 3-hexyne.

In Formulas I-XVI, as appropriate, suitable aryl groups include phenyl, naphthyl and the like, while suitable heteroaryl groups include pyridyl, furanyl, imidazolyl, benzimidazolyl, pyrimidinyl, thiophenyl or thienyl, quinolinyl, indolyl, thiazolyl, and the like.

In Formulas I-XVI, as appropriate, suitable alkylaminos include —$CH_2CH_2CH_2NH$— or $CH_2CH_2NH$—.

VI. Methods of Synthesizing Oligonucleotides

The 4'-phosphate analog-modified oligonucleotides described in this application can be made using a variety of synthetic methods known in the art, including standard phosphoramidite methods. Any phosphoramidite synthesis method can be used to synthesize the 4'-phosphate analog-modified oligonucleotides of this invention. In certain embodiments, phosphoramidites are used in a solid phase synthesis method to yield reactive intermediate phosphite compounds, which are subsequently oxidized using known methods to produce phosphonate-modified oligonucleotides, typically with a phosphodiester or phosphorothioate internucleotide linkages. The oligonucleotide synthesis of the present disclosure can be performed in either direction: from 5' to 3' or from 3' to 5' using art known methods.

Thus, in another aspect, the present disclosure relates to methods of synthesizing oligonucleotides using a 4'-phosphate analog-modified nucleoside phosphoramidite, such as those discussed above and represented, for example, by Formulas X-XVI. Typically, the 4'-phosphate analog-modified nucleoside is incorporated as the terminal nucleotide of the synthesized oligonucleotide. More typically, the phosphate analog-modified nucleoside is incorporated as the 5'-terminal nucleotide of the synthesized oligonucleotide.

In certain embodiments, the method for synthesizing an oligonucleotide comprises (a) attaching a nucleoside to a solid support via a covalent linkage; (b) coupling a nucleoside phosphoramidite to a reactive hydroxyl group on the nucleoside of step (a) to form an internucleotide bond therebetween, wherein any uncoupled nucleoside on the solid support is capped with a capping reagent; (c) oxidizing said internucleotide bond with an oxidizing agent; and (d) repeating steps (b) to (c) iteratively with subsequent nucleoside phosphoramidites to form an oligonucleotide, wherein at least the nucleoside of step (a), the nucleoside phosphoramidite of step (b) or at least one of the subsequent nucleoside phosphoramidites of step (d) comprises a phosphonate-containing moiety as described herein. Typically, the coupling, capping/oxidizing steps and optionally, deprotecting steps, are repeated until the oligonucleotide reaches the desired length and/or sequence, after which it is cleaved from the solid support.

VI. Pharmaceutical Compositions

The present disclosure provides pharmaceutical compositions comprising a 4'-phosphate analog-modified nucleic acid inhibitor molecule and a pharmaceutically acceptable excipient.

In some embodiments, the pharmaceutical composition comprises a pharmaceutically acceptable excipient and a therapeutically effective amount of a nucleic acid inhibitor molecule, wherein the nucleic acid inhibitor molecule comprises at least one nucleotide comprising a phosphate analog, as described herein.

In some embodiments, the pharmaceutical composition comprises a pharmaceutically acceptable excipient and a therapeutically effective amount of a nucleic acid inhibitor molecule, wherein the nucleic acid inhibitor molecule comprises at least one 4'-phosphate analog-containing nucleotide represented by any one of Formulas I-IX, as described previously.

Although the pharmaceutical compositions typically comprise a nucleic acid inhibitor molecule, pharmaceutical compositions can also be prepared using other therapeutic nucleic acids (e.g., gene therapy oligonucleotide or CRISPR oligonucleotide) that have been modified with a 4'-phosphate analog, as described herein.

VIII. Pharmaceutically-Acceptable Excipients

The pharmaceutically-acceptable excipients useful in this disclosure are conventional. Remington's Pharmaceutical Sciences, by E. W. Martin, Mack Publishing Co., Easton, Pa., 15$^{th}$ Edition (1975), describes compositions and formulations suitable for pharmaceutical delivery of one or more therapeutic compositions. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; malt; gelatin; excipients, such as cocoa butter and suppository waxes; oils, such as peanut oil, cottonseed oil, safflower oil, sesame oil, olive oil, corn oil and soybean oil; buffering agents, such as magnesium hydroxide and aluminum hydroxide; (isotonic saline; Ringer's solution); ethyl alcohol; pH buffered solutions; polyols, such as glycerol, propylene glycol, polyethylene glycol, and the like; and other non-toxic compatible substances employed in pharmaceutical formulations.

IX. Dosage Forms

Pharmaceutical compositions comprising a 4'-phosphate-analog containing oligonucleotide (e.g., nucleic acid inhibitor molecule) may be formulated with conventional excipients for any intended route of administration.

Typically, the pharmaceutical compositions of the present disclosure comprise a 4'-phosphate analog-containing nucleic acid inhibitor molecule, as described herein, and are formulated in liquid form for parenteral administration, for example, by subcutaneous, intramuscular, intravenous or epidural injection. Dosage forms suitable for parenteral administration typically comprise one or more suitable vehicles for parenteral administration including, by way of example, sterile aqueous solutions, saline, low molecular weight alcohols such as propylene glycol, polyethylene glycol, vegetable oils, gelatin, fatty acid esters such as ethyl oleate, and the like. The parenteral formulations may contain sugars, alcohols, antioxidants, buffers, bacteriostats, solutes which render the formulation isotonic with the blood of the intended recipient or suspending or thickening agents. Proper fluidity can be maintained, for example, by the use of surfactants. Liquid formulations can be lyophilized and stored for later use upon reconstitution with a sterile injectable solution.

The pharmaceutical compositions may also be formulated for other routes of administration including topical or transdermal administration, rectal or vaginal administration, ocular administration, nasal administration, buccal administration, or sublingual administration.

X. Delivery Agents

The 4'-phosphate analog-containing oligonucleotides (e.g., nucleic acid inhibitor molecule) may be admixed, encapsulated, conjugated or otherwise associated with other molecules, molecule structures or mixtures of compounds, including, for example, liposomes and lipids such as those disclosed in U.S. Pat. Nos. 6,815,432, 6,586,410, 6,858,225, 7,811,602, 7,244,448 and 8,158,601; polymeric materials such as those disclosed in U.S. Pat. Nos. 6,835,393, 7,374,778, 7,737,108, 7,718,193, 8,137,695 and U.S. Published Patent Application Nos. 2011/0143434, 2011/0129921, 2011/0123636, 2011/0143435, 2011/0142951, 2012/0021514, 2011/0281934, 2011/0286957 and 2008/0152661; capsids, capsoids, or receptor targeted molecules for assisting in uptake, distribution or absorption.

In certain embodiments, the 4'-phosphate analog-containing oligonucleotide (e.g., nucleic acid inhibitor molecule) is formulated in a lipid nanoparticle (LNP). Lipid-nucleic acid nanoparticles typically form spontaneously upon mixing lipids with nucleic acid to form a complex. Depending on the desired particle size distribution, the resultant nanoparticle mixture can be optionally extruded through a polycarbonate membrane (e.g., 100 nm cut-off) using, for example, a thermobarrel extruder, such as LIPEX® Extruder (Northern Lipids, Inc). To prepare a lipid nanoparticle for therapeutic use, it may desirable to remove solvent (e.g., ethanol) used to form the nanoparticle and/or exchange buffer, which can be accomplished by, for example, dialysis or tangential flow filtration. Methods of making lipid nanoparticles containing nucleic acid inhibitor molecules are known in the art, as disclosed, for example in U.S. Published Patent Application Nos. 2015/0374842 and 2014/0107178.

In certain embodiments, the LNP comprises a lipid core comprising a cationic liposome and a pegylated lipid. The LNP can further comprise one or more envelope lipids, such as a cationic lipid, a structural or neutral lipid, a sterol, a pegylated lipid, or mixtures thereof.

In certain embodiments, an oligonucleotide of the invention is covalently conjugated to a ligand that directs delivery of the oligonucleotide to a tissue of interest. Many such ligands have been explored. See, e.g., Winkler, *Ther. Deliv.*, 2013,4(7): 791-809. For example, an oligonucleotide of the invention can be conjugated to multiple sugar ligand moieties (e.g., N-acetylgalactosamine (GalNAc)) to direct uptake of the oligonucleotide into the liver. See, e.g., WO 2016/100401. Other ligands that can be used include, but are not limited to, mannose-6-phosphate, cholesterol, folate, transferrin, and galactose (for other specific exemplary ligands see, e.g., WO 2012/089352). Typically, when an oligonucleotide is conjugated to a ligand, the oligonucleotide is administered as a naked oligonucleotide, wherein the oligonucleotide is not also formulated in an LNP or other protective coating. In certain embodiments, each nucleotide within the naked oligonucleotide is modified at the 2'-position of the sugar moiety, typically with 2'-F or 2'-OMe.

These pharmaceutical compositions may be sterilized by conventional sterilization techniques, or may be sterile filtered. The resulting aqueous solutions may be packaged for use as is, or lyophilized, the lyophilized preparation being combined with a sterile aqueous excipient prior to administration. The pH of the preparations typically will be between 3 and 11, more preferably between 5 and 9 or between 6 and 8, and most preferably between 7 and 8, such as 7 to 7.5. The pharmaceutical compositions in solid form may be packaged in multiple single dose units, each containing a fixed amount of the above mentioned agent or agents, such as in a sealed package of tablets or capsules. The pharmaceutical compositions in solid form can also be packaged in a container for a flexible quantity, such as in a squeezable tube designed for a topically applicable cream or ointment.

The pharmaceutical compositions of the present disclosure are applied for therapeutic use. Thus, one aspect of the disclosure provides a pharmaceutical composition, which may be used to treat a subject including, but not limited to, a human suffering from a disease or a condition by administering to said subject an effective amount of a pharmaceutical composition of the present disclosure.

In certain embodiments, the present disclosure features the use of a therapeutically effective amount of a pharmaceutical composition as described herein for the manufacture of a medicament for treatment of a patient in need thereof.

XI. Methods of Use

The 4'-phosphate analog-containing nucleic acid inhibitor molecules described herein can be used in a method of modulating the expression of a target gene in a cell. Typically, such methods comprise introducing the 4'-phosphate analog-containing nucleic acid inhibitor molecule into a cell in an amount sufficient to modulate the expression of a target gene. In certain embodiments, the method is carried out in vivo. The method can also be carried out in vitro or ex vivo. In certain embodiments, the cell is a mammalian cell, including, but not limited to, a human cell.

In certain embodiments, the 4'-phosphate analog-containing oligonucleotides described herein (e.g., nucleic acid inhibitor molecules) can be used in a method of treating a patient in need thereof. Typically, such methods comprise administering a therapeutically effective amount of a pharmaceutical composition comprising a 4'-phosphate analog-containing nucleic acid inhibitor molecule, as described herein, to a patient in need thereof.

In certain embodiments, the pharmaceutical compositions disclosed herein may be useful for the treatment or prevention of symptoms related to a viral infection in a patient in need thereof. One embodiment is directed to a method of treating a viral infection, comprising administering to a subject a pharmaceutical composition comprising a therapeutically effective amount of a 4'-phosphate analog-containing oligonucleotide (e.g., nucleic acid inhibitor molecule), as described herein. Non-limiting examples of such viral infections include HCV, HBV, HPV, HSV or HIV infection.

In certain embodiments, the pharmaceutical compositions disclosed herein may be useful for the treatment or prevention of symptoms related to cancer in a patient in need thereof. One embodiment is directed to a method of treating cancer, comprising administering to a subject a pharmaceutical composition comprising a therapeutically effective amount of a 4'-phosphate analog-modified nucleic acid inhibitor molecule, as described herein. Non-limiting examples of such cancers include bilary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, wilms tumor, leukemia, acute lymocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T-cell lymphomas, non-Hodgkin lymphoma, precursor T-lymphoblastic lymphoma/leukemia, peripheral T-cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma. Typically, the present disclosure features methods of treating liver cancer, liver carcinoma, hepatoma, hepatocellular carcinoma, cholangiocarcinoma and hepatoblastoma by administering a therapeutically effective amount of a pharmaceutical composition as described herein.

In certain embodiments the pharmaceutical compositions disclosed herein may be useful for treatment or prevention of symptoms related to proliferative, inflammatory, autoimmune, neurologic, ocular, respiratory, metabolic, dermatological, auditory, liver, kidney, or infectious diseases. One embodiment is directed to a method of treating a proliferative, inflammatory, autoimmune, neurologic, ocular, respiratory, metabolic, dermatological, auditory, liver, kidney, or infectious disease, comprising administering to a subject a pharmaceutical composition comprising a therapeutically effective amount of a 4'-phosphate analog-modified nucleic acid inhibitor molecule, as described herein. Typically, the disease or condition is disease of the liver.

In some embodiments, the present disclosure provides a method for reducing expression of a target gene in a subject comprising administering a pharmaceutical composition to a subject in need thereof in an amount sufficient to reduce expression of the target gene, wherein the pharmaceutical composition comprises a 4'-phosphate analog-modified nucleic acid inhibitor molecule as described herein and a pharmaceutically acceptable excipient as also described herein.

In some embodiments, the 4'-phosphate analog-modified nucleic acid inhibitor molecule is an RNAi inhibitor molecule as described herein, including a dsRNAi inhibitor molecule or an ssRNAi inhibitor molecule.

The target gene may be a target gene from any mammal, such as a human target gene. Any gene may be silenced according to the instant method. Exemplary target genes include, but are not limited to, Factor VII, Eg5, PCSK9, TPX2, apoB, SAA, TTR, HBV, HCV, RSV, PDGF beta gene, Erb-B gene, Src gene, CRK gene, GRB2 gene, RAS gene, MEKK gene, JNK gene, RAF gene, Erkl/2 gene, PCNA (p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, p73 gene, p21 (WAF1/CIP1) gene, p27 (KIP1) gene, PPM1D gene, RAS gene, caveolin I gene, MIB I gene, MTAI gene, M68 gene, mutations in tumor suppressor genes, p53 tumor suppressor gene, LDHA, and combinations thereof.

In some embodiments the 4'-phosphate analog-modified nucleic acid inhibitor molecule silences a target gene and thus can be used to treat a subject having or at risk for a disorder characterized by unwanted expression of the target gene. For example, in some embodiments, the present 4'-phosphate analog-modified nucleic acid inhibitor molecule silences the beta-catenin gene, and thus can be used to treat a subject having or at risk for a disorder characterized by unwanted beta-catenin expression, e.g., adenocarcinoma or hepatocellular carcinoma.

Typically, the 4'-phosphate analog-containing oligonucleotides (e.g., nucleic acid inhibitor molecules) of the invention are administered intravenously or subcutaneously. However, the pharmaceutical compositions disclosed herein may also be administered by any method known in the art, including, for example, oral, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

In certain embodiments, the pharmaceutical composition is delivered via systemic administration (such as via intravenous or subcutaneous administration) to relevant tissues or cells in a subject or organism, such as the liver. In other embodiments, the pharmaceutical composition is delivered via local administration or systemic administration. In certain embodiments, the pharmaceutical composition is delivered via local administration to relevant tissues or cells, such as lung cells and tissues, such as via pulmonary delivery.

The therapeutically effective amount of the compounds disclosed herein may depend on the route of administration and the physical characteristics of the patient, such as the size and weight of the subject, the extent of the disease progression or penetration, the age, health, and sex of the subject In certain embodiments, the 4'-phosphate analog-modified oligonucleotide, as described herein, is administered at a dosage of 20 micrograms to 10 milligrams per kilogram body weight of the recipient per day, 100 micrograms to 5 milligrams per kilogram body weight of the recipient per day, or 0.5 to 2.0 milligrams per kilogram body weight of the recipient per day.

A pharmaceutical composition of the instant disclosure may be administered every day or intermittently. For example, intermittent administration of a compound of the instant disclosure may be administration one to six days per week, one to six days per month, once weekly, once every other week, once monthly, once every other month, or once or twice per year or divided into multiple yearly, monthly, weekly, or daily doses. In some embodiments, intermittent dosing may mean administration in cycles (e.g. daily administration for one day, one week or two to eight consecutive weeks, then a rest period with no administration for up to one week, up to one month, up to two months, up to three months or up to six months or more) or it may mean administration on alternate days, weeks, months or years.

In any of the methods of treatment of the invention, the compounds may be administered to the subject alone as a monotherapy or in combination with additional therapies known in the art.

EXAMPLES

Example 1: Synthesis of Phosphoramidite 1

The below Scheme 1 depicts the synthesis of the following nucleoside phosphoramidite comprising a diethyl protected, oxymethylphosphonate: (2R,3S,4R,5R)-5-(3-((benzyloxy)methyl)-2,4-dioxo-3,4-dihydropyrimidin-1(2H)-yl)-2-((diethoxyphosphoryl)methoxy)-4-methoxytetrahydrofuran-3-yl (2-cyanoethyl) diisopropylphosphoramidite (Phosphoramidite 1).

Scheme 1

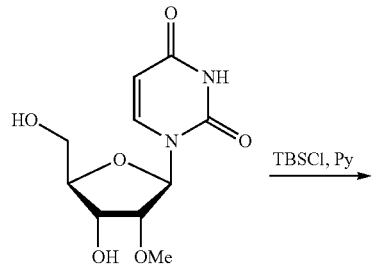

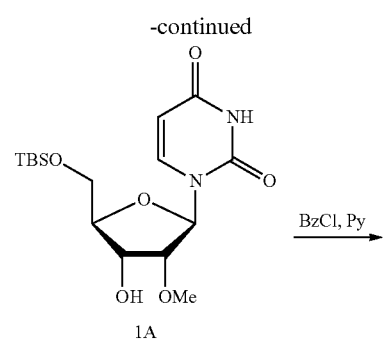

1A

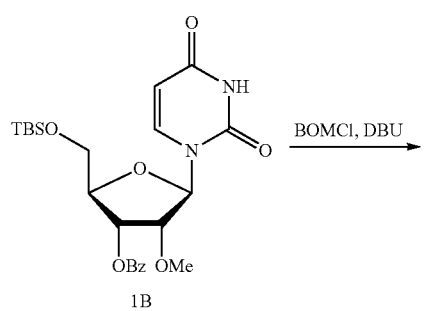

1B

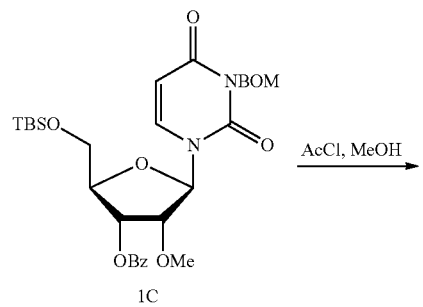

1C

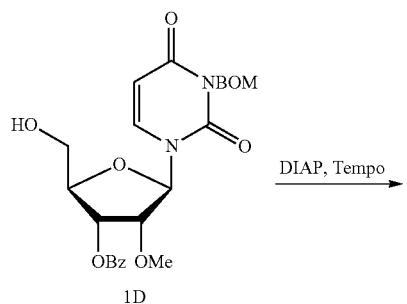

1D

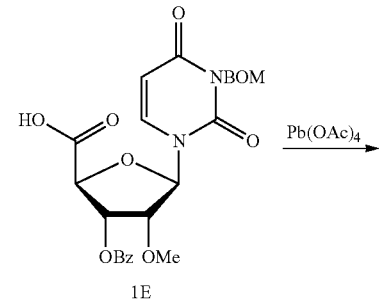

1E

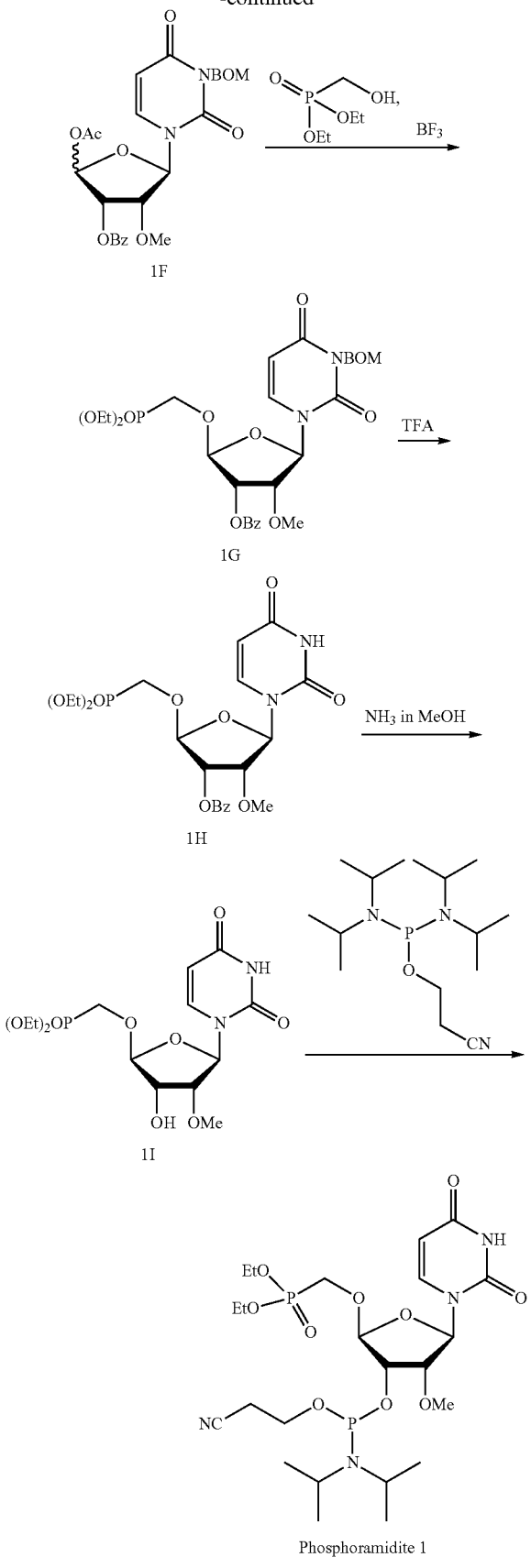

Synthesis of (2R,3R,4R,5R)-2-(((tert-butyldimethyl-silyl)oxy)methyl)-5-(2,4-dioxo-3,4-dihydropyrimidin-1(2H)-yl)-4-methoxytetrahydrofuran-3-yl Benzoate (1B)

A solution of 2'-O-Methyluridine (150 g, 580.9 mmol) in pyridine (1.5 L) was cooled in an ice-bath. To the solution, tert-butylchlorodimethylsilane (96.3 g, 639.0 mmol) was added in 15 minutes via several portions. The reaction mixture was stirred at room temperature for five hours. The reaction mixture was then cooled in an ice bath. Benzoyl chloride (165.5 g, 1.2 mol) was added dropwise in 15 minutes to the reaction mixture. The reaction mixture was continuously stirred at room temperature for 12 hours before being diluted with ethyl acetate (2 L). The solution was washed with water (3 L×3), saturated NaHCO$_3$ solution (1 L×2), and brine (1 L). The organic layer was dried over Na$_2$SO$_4$, filtered and concentrated in vacuo to give a light yellow residue of 1B (500 g, crude) that was used directly for the next step.

Synthesis of (2R,3R,4R,5R)-5-(3-((benzyloxy)methyl)-2,4-dioxo-3,4-dihydropyrimidin-1(2H)-yl)-2-(((tert-butyldimethylsilyl)oxy)methyl)-4-methoxytetrahydrofuran-3-yl Benzoate (1C)

The product (500 g, crude) from the previous step (1B) was dissolved in DMF (5 L). The solution was cooled in an ice bath. Benzyl chloromethyl ether (74.2 g, 1.16 mol) and DBU (239.8 g, 1.58 mol) were added, and the reaction mixture was allowed to warm up to room temperature and stirred for 16 hours. The reaction was quenched with 0.1N HCl (2 L) and diluted with ethyl acetate (2 L). The organic layer was separated. It was then washed with water, brine, dried over Na$_2$SO$_4$, filtered and concentrated in vacuo. The crude material was purified on silica gel chromatography eluting with CH$_2$Cl$_2$:MeOH (20:1) to yield the title product, 1C, (500 g, 837.9 mmol) as yellow oil.

$^1$H NMR: (CD3OD, 400 MHz): δ 7.93-7.95 (d, J=7.2 Hz, 2H), 7.85-7.87 (d, J=8.0 Hz, 1H), 7.50-7.52 (d, J=7.2 Hz, 1H), 7.36-7.40 (t, J=8.0 Hz, 2H), 7.12-7.19 (m, 5H), 5.90-5.91 (d, J=3.2 Hz, 1H), 5.54-5.56 (d, J=8.4 Hz, 1H), 5.35 (s, 2H), 5.24-5.27 (t, J=5.6 Hz, 1H), 4.55 (d, J=1.6 Hz, 2H), 4.28-4.29 (d, J=5.6 Hz, 1H), 3.93-4.01 (m, 1H), 3.81-3.93 (t, J=6.8 Hz, 1H), 3.32 (s, 3H), 0.81-0.84 (d, J=7.6 Hz, 10H), 0.00 (s, 6H); m/z found [M+H]$^+$=597.2

Synthesis of (2R,3R,4R,5R)-5-(3-((benzyloxy)methyl)-2,4-dioxo-3,4-dihydropyrimidin-1(2H)-yl)-2-(hydroxymethyl)-4-methoxytetrahydrofuran-3-yl Benzoate (1D)

The solution of 1C (250 g, 419 mmol) in MeOH (1.5 L) was placed in an ice bath, and acetyl chloride (24.9 g, 502.7 mmol) was added dropwise in 15 minutes. The reaction was allowed to warm up to room temperature and stirred for 2 hours. Ag$_2$CO$_3$ (138.6 g, 502.7 mmol) was added to the reaction and stirred for one hour. The reaction mixture was filtered and concentrated in vacuo to give the title compound, 1D, (400 g, crude) as yellow oil.

$^1$H NMR: (CD$_3$OD, 400 MHz): δ 8.02-8.05 (m, 3H), 7.57-7.59 (d, J=7.6 Hz, 1H), 7.44-7.48 (t, J=7.6 Hz, 2H), 7.19-7.27 (q, J=7.2 Hz, 5H), 6.03-6.05 (d, J=9.2 Hz, 1H), 5.72-5.74 (d, J=8.0 Hz, 1H), 5.41-5.44 (t, J=8.8 Hz, 3H), 4.63 (s, 2H), 4.29-4.31 (t, J=2.4 Hz, 1H), 4.17-4.19 (t, J=5.2 Hz, 1H), 3.79-3.88 (m, 2H), 3.37 (s, 3H); m/z found [M+H]$^+$=482.2

Synthesis of (2S,3S,4R,5R)-3-(benzoyloxy)-5-(3-((benzyloxy)methyl)-2,4-dioxo-3,4-dihydropyrimidin-1(2H)-yl)-4-methoxytetrahydrofuran-2-carboxylic Acid (1E)

[Acetoxy(phenyl)-iodanyl] acetate (293.7 g, 912 mmol) was added to a suspension of 1D (200 g, 414.5 mmol) and TEMPO (15.64 g, 99.48 mmol) in water (1 L) and $CH_3CN$ (1 L). The reaction mixture was stirred at room temperature for 12 hours and then diluted with ethyl acetate. The organic layer was separated and washed with water, brine, dried over $Na_2SO_4$, filtered and concentrated in vacuo. The crude material was purified on silica gel chromatography eluting with $CH_2Cl_2$:MeOH (20:1) to yield the title product, 1E, (150 g, 837.9 mmol) as yellow oil.

$^1$H NMR: ($CD_3OD$, 400 MHz): δ 8.21-8.23 (d, J=8.0 Hz, 1H), 7.93-7.97 (t, J=7.6 Hz, 2H), 7.52 (s, 1H), 7.37-7.41 (t, J=4.6 Hz, 2H), 7.10-7.20 (m, 4H), 7.02-7.06 (m, 2H), 6.95 (s, 1H), 6.08-6.09 (d, J=5.6 Hz, 1H), 5.69-5.71 (d, J=8.0 Hz, 1H), 5.60-5.62 (t, J=4.0 Hz, 1H), 5.31-5.36 (t, J=9.6 Hz, 2H), 4.54 (s, 2H), 4.11-4.13 (t, J=4.8 Hz, 1H), 3.29 (s, 3H); m/z found [M+H]$^+$=497.2

Synthesis of (2R,3S,4R,5R)-2-acetoxy-5-(3-((benzyloxy)methyl)-2,4-dioxo-3,4-dihydropyrimidin-1(2H)-yl)-4-methoxytetrahydrofuran-3-yl Benzoate (1F)

A dry flask was charged with 1E (20 g, 40.3 mmol) and Pb(OAc)4 (53.6 g, 120.8 mmol). The reaction mixture was purged with argon before DMF (150 mL) was added. The reaction was protected from light and stirred at room temperature for 16 hours. It was quenched with water (600 mL) and diluted with ethyl acetate (400 mL). The resultant suspension was filtered through a pad of celite. The solids were rinsed with ethyl acetate. The organic layer was separated and concentrated in vacuo. The crude material was purified on silica gel chromatography eluting with petroleum ether:ethyl acetate (3:1) to yield the title product, 1F, (7 g, 13.7 mmol) as an α/β mixture.

$^1$H NMR: ($CD_3OD$, 400 MHz): δ 8.10-8.13 (t, J=7.6 Hz, 3H), 7.65-7.69 (t, J=5.6 Hz, 3H), 7.54-7.58 (t, J=8.0 Hz, 3H), 7.26-7.35 (m, 9H), 6.35-6.37 (t, J=6.8 Hz, 2H), 5.89-5.91 (d, J=8.0 Hz, 1H), 5.68-5.69 (d, J=4.0 Hz, 1H), 5.48-5.50 (t, J=1.6 Hz, 3H), 4.68-4.71 (t, J=7.2 Hz, 3H), 4.54-4.57 (q, J=4.8 Hz, 1H), 3.44 (s, 4H), 2.21 (s, 3H); m/z found [M+H]$^+$=511.2

Synthesis of (2R,3S,4R,5R)-5-(3-((benzyloxy)methyl)-2,4-dioxo-3,4-dihydropyrimidin-1(2H)-yl)-2-((diethoxyphosphoryl)methoxy)-4-methoxytetrahydrofuran-3-yl Benzoate (1G)

The reaction was performed under argon. Diethyl (hydroxymethyl)phosphonate (26.4 g, 156.7 mmol) and boron trifluoride diethyl etherate (27.8 g, 196.0 mmol) were added to a solution of 1F (20 g, 39.2 mmol) in anhydrous $CH_2Cl_2$ (130 mL). The reaction was stirred at room temperature for 16 hours. The reaction was quenched with water and extracted with ethyl acetate. The organic layer was separated, washed with brine, dried over $Na_2SO_4$ and concentrated in vacuo. The crude material was purified on silica gel chromatography eluting with petroleum ether:ethyl acetate (3:1 to 1:1) to yield the title compound, 1G, (7 g, 13.7 mmol) as white foam.

$^1$H NMR: ($CD_3OD$, 400 MHz): δ 8.10-8.13 (t, J=7.6 Hz, 3H), 7.65-7.69 (t, J=5.6 Hz, 3H), 7.54-7.58 (t, J=8.0 Hz, 3H), 7.26-7.35 (m, 9H), 6.35-6.37 (t, J=6.8 Hz, 2H), 5.89-5.91 (d, J=8.0 Hz, 1H), 5.68-5.69 (d, J=4.0 Hz, 1H), 5.48-5.50 (t, J=1.6 Hz, 3H), 4.68-4.71 (t, J=7.2 Hz, 3H), 4.54-4.57 (q, J=4.8 Hz, 1H), 3.44 (s, 4H), 2.21 (s, 3H); m/z found [M+H]$^+$=619.2

Synthesis of (2R,3S,4R,5R)-2-((diethoxyphosphoryl)methoxy)-5-(2,4-dioxo-3,4-dihydropyrimidin-1 (2H)-yl)-4-methoxytetrahydrofuran-3-yl Benzoate (1H)

The solution of 1G (9 g, 14.6 mmol) in TFA (90 mL) was stirred at 80° C. for 30 minutes and then concentrated in vacuo. The crude material was purified on silica gel chromatography eluting with $CH_2Cl_2$:MeOH (70:1) to yield the title compound, 1H, (6.8 g, 13.7 mmol) as white foam.

$^1$H NMR: ($CD_3OD$, 400 MHz): δ 11.54 (s, 1H), 8.03-8.04 (d, J=7.6 Hz, 2H), 7.61 (s, 5H), 6.26-6.28 (d, J=6.8 Hz, 1H), 5.73-5.76 (m, 1H), 5.55-5.56 (d, J=4.4 Hz, 1H), 5.39 (s, 1H), 4.49-4.50 (t, J=4.4 Hz, 1H), 4.02-4.14 (m, 11H), 3.18 (s, 3H), 1.24-1.30 (m, 6H); m/z found [M+H]$^+$=499.2

Synthesis of diethyl (((((2R,3S,4R,5R)-5-(2,4-dioxo-3,4-dihydropyrimidin-1(2H)-yl)-3-hydroxy-4-methoxytetrahydrofuran-2-yl)oxy)methyl)phosphonate (1I)

A solution of 1H (5 g, 10 mmol) in ammonia in methanol (7 N, 50 mL) was stirred at room temperature for 16 hours. The reaction mixture was concentrated in vacuo. The crude material was purified on silica gel chromatography eluting with $CH_2Cl_2$:MeOH (70:1) to yield title compound, 1I, (3.3 g, 25.4 mmol) as white foam.

$^1$H NMR: ($CD_3OD$, 400 MHz): δ 11.53 (s, 1H), 8.02-8.04 (t, J=7.2 Hz, 2H), 7.59-7.74 (m, 4H), 6.27-6.28 (d, J=7.8 Hz, 1H), 5.74-5.76 (d, J=8.0 Hz, 1H), 5.55-5.56 (d, J=4.4 Hz, 1H), 5.39 (s, 1H), 4.49-4.50 (t, J=4.8 Hz, 1H), 4.02-4.13 (m, 7H), 3.32 (s, 3H), 1.25-1.30 (m, 7H); m/z found [M+H]+=395.1

Synthesis of 2-cyanoethyl ((2R,3S,4R,5R)-2-((diethoxyphosphoryl)methoxy)-5-(2,4-dioxo-3,4-dihydropyrimidin-1(2H)-yl)-4-methoxytetrahydrofuran-3-yl) Diisopropylphosphoramidite (Phosphoramidite 1)

DIPEA (2.4 g, 18.3 mmol) was added to a solution of 1I (4 g, 10.1 mmol) in anhydrous $CH_2Cl_2$ (40 mL), followed by 3-[chloro-(diisopropylamino)phosphanyl]oxypropanenitrile (3.4 g, 14.2 mmol). The reaction mixture was stirred at room temperature for 2 hours and then quenched with MeOH. The reaction mixture was diluted with ethyl acetate, washed with saturated $NaHCO_3$, water and brine. The organic layer was concentrated in vacuo. The crude material was purified on silica gel chromatography eluting with $CH_2Cl_2$:MeOH (70:1) to yield the title compound, Phosphoramidite 1, (2.9 g, 10.1 mmol) as white solid.

$^1$H NMR ($CD_3OD$, 400 MHz): δ 9.13 (s, 1H), 7.54-7.59 (q, J=8.4 Hz, 1H), 6.17-6.19 (d, J=7.2 Hz, 1H), 5.68-5.70 (d, J=8.0 Hz, 1H), 5.08-5.16 (d, J=28.8 Hz, 1H), 4.38-4.40 (d, J=9.2 Hz, 1H), 4.07-4.12 (m, 5H), 3.83-3.86 (d, J=8.8 Hz, 1H), 3.63 (s, 5H), 3.33-3.37 (d, J=14.4 Hz, 3H), 2.66-2.70 (q, J=5.6 Hz, 2H), 1.27-1.30 (m, 6H), 1.17-1.21 (q, J=6.0 Hz, 2H). $^{31}$P NMR ($CD_3CN$, 162 MHz): δ 151.54, 150.57, 19.84; m/z found [M+H]$^+$=595.2

Example 2: Synthesis of Phosphoramidite 2

The below Scheme 2 depicts the synthesis of the following nucleoside phosphoramidite comprising a diethyl protected, oxymethylphosphonate: 2-cyanoethyl ((2R,3R,4R,5R)-2-((diethoxyphosphoryl)methoxy)-5-(2,4-dioxo-3,4-dihydropyrimidin-1(2H)-yl)-4-fluorotetrahydrofuran-3-yl) diisopropylphosphoramidite (Phosphoramidite 2). Phosphoramidite 2 was prepared following the procedures described in Example 1.
Scheme 2
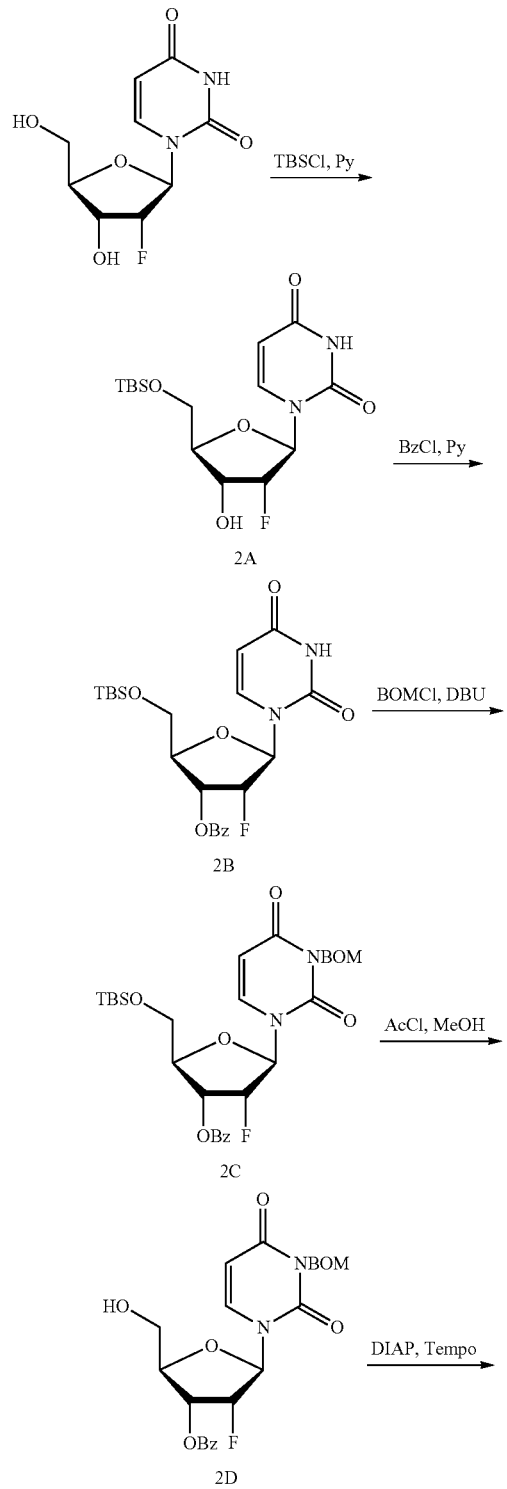
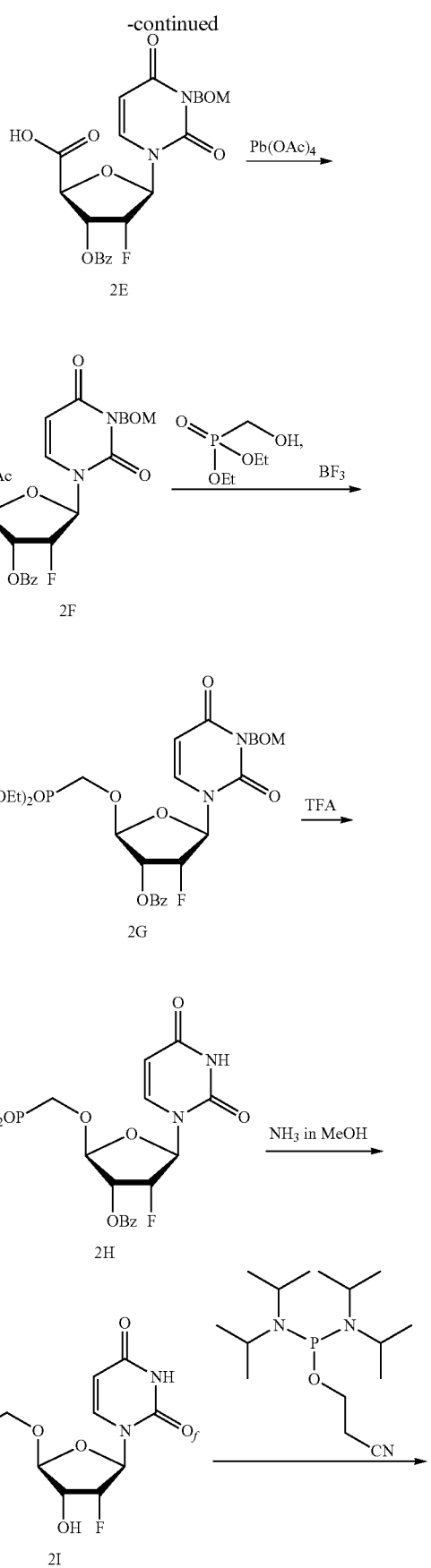

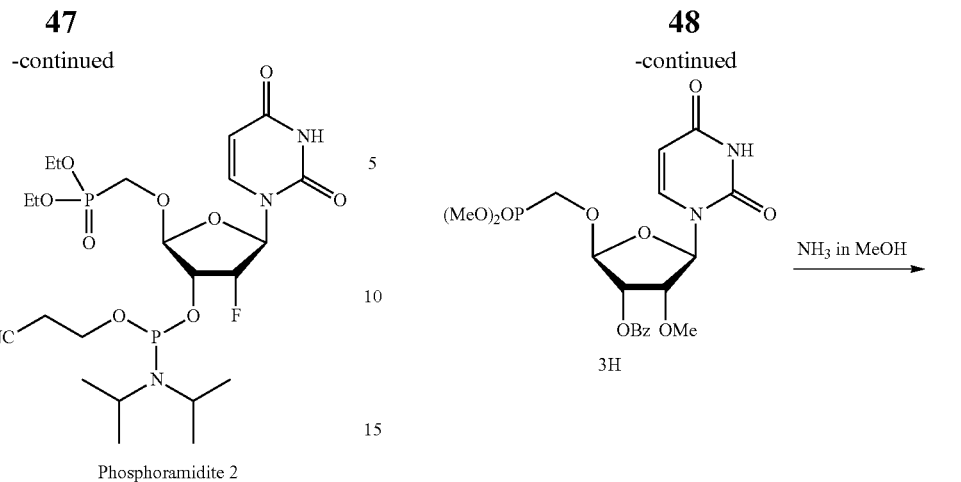

Phosphoramidite 2

The $^1$H NMR spectrum (CD$_3$CN, 400 MHz) of Phosphoramidite 2 is as follows: δ 7.57-7.59 (d, J=8.2 Hz, 1H) 6.26-6.35 (m, 1H) 5.70-5.73 (q, J=4.8 Hz, 1H) 5.21-5.34 (m, 2H) 4.45 (m, 1H) 4.13-4.17 (m, 5H) 4.13 (m, 3H) 3.70-3.72 (m, 2H) 2.69-2.74 (m, 2H) 1.31-1.35 (m, 6H) 1.21-1.24 (q, J=2.0 Hz, 13H). The $^{19}$F NMR (CD$_3$CN, 376 MHz) spectrum of Phosphoramidite 2 is as follows: δ −212.04, −212.04 (m, 0.6F); −215.00, −215.02 (m, 0.4F). The $^{31}$P NMR (162 MHz, CDCl$_3$) spectrum of Phosphoramidite 2 is as follows: δ 19.39, 19.26, 151.9, 151.3; m/z found [M+H]$^+$=583.2

Example 3: Synthesis of Phosphoramidite 3

The below Scheme 3 depicts the synthesis of the following nucleoside phosphoramidite comprising a dimethyl-protected, oxymethylphosphonate: (2R,3S,4R,5R)-5-(3-((benzyloxy)methyl)-2,4-dioxo-3,4-dihydropyrimidin-1(2H)-yl)-2-((dimethoxyphosphoryl)methoxy)-4-methoxytetrahydrofuran-3-yl (2-cyanoethyl) diisopropylphosphoramidite (Phosphoramidite 3). Phosphoramidite 3 was prepared following the procedures described in Example 1.

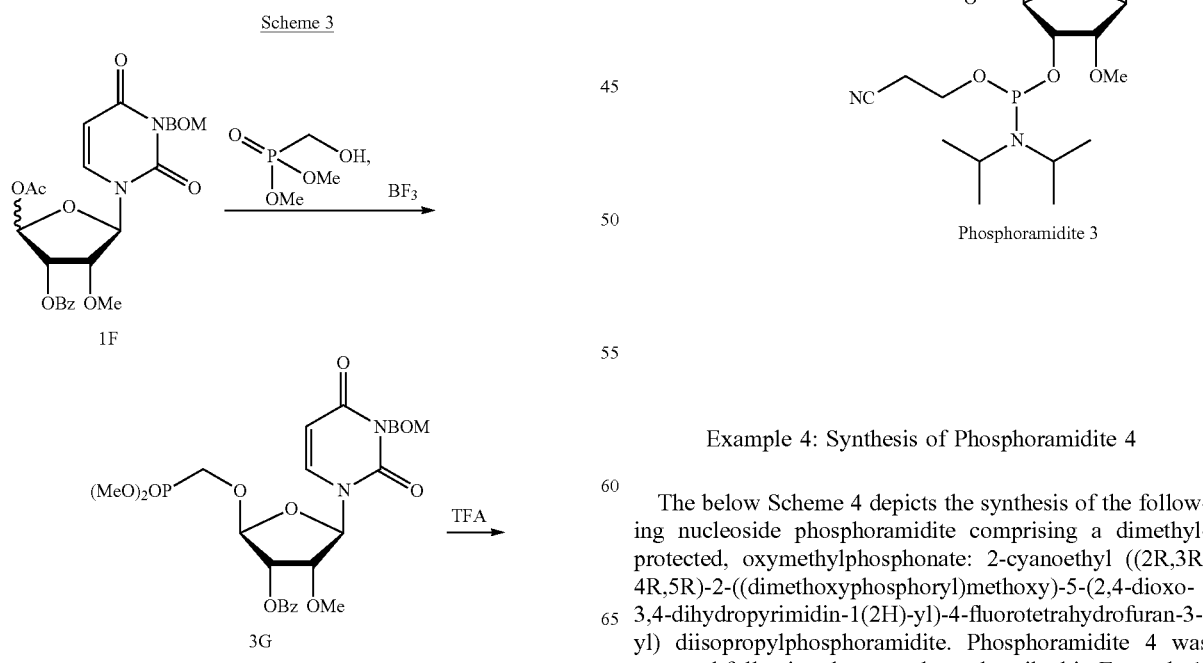

Example 4: Synthesis of Phosphoramidite 4

The below Scheme 4 depicts the synthesis of the following nucleoside phosphoramidite comprising a dimethyl-protected, oxymethylphosphonate: 2-cyanoethyl ((2R,3R,4R,5R)-2-((dimethoxyphosphoryl)methoxy)-5-(2,4-dioxo-3,4-dihydropyrimidin-1(2H)-yl)-4-fluorotetrahydrofuran-3-yl) diisopropylphosphoramidite. Phosphoramidite 4 was prepared following the procedures described in Example 1.

Scheme 4

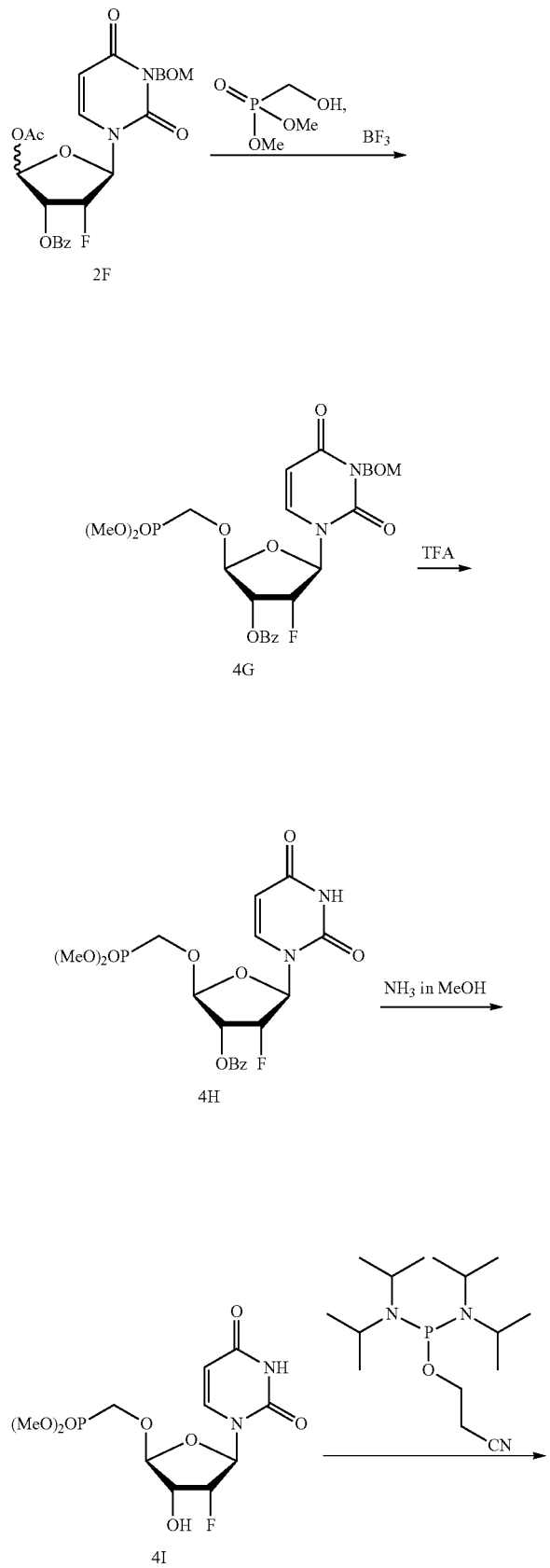

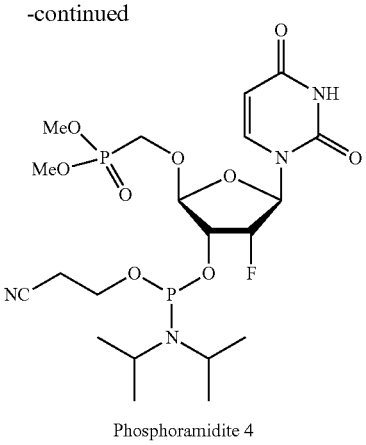

Phosphoramidite 4

Example 5: Synthesis of Phosphoramidite 5 and Phosphoramidite 5'

A carbocyclic nucleoside phosphoramidite having a 4'-oxymethylphosphonate was synthesized. Carbocyclic nucleosides represent a class of nucleoside analogs that possess a cyclopentane ring in place of the tetrahydrofuran ring of the nucleoside, a modification that can confer antiviral properties to the nucleoside analog. See e.g., U.S. Pat. No. 6,001,840. In other words, a carbocyclic nucleoside is a nucleoside analog in which the oxygen atom of the furanose ring of the sugar moiety is substituted by a carbon atom.

The below Scheme 5 depicts the synthesis of the following carbocyclic nucleoside phosphoramidite enantiomers comprising a diethyl-protected, oxymethylphosphonate: 1) 2-cyanoethyl ((1S,2S,4R)-2-((diethoxyphosphoryl)methoxy)-4-(2,4-dioxo-3,4-dihydropyrimidin-1(2H)-yl)cyclopentyl) diisopropylphosphoramidite (Phosphoramidite 5) and 2) 2-cyanoethyl ((1R,2R,4S)-2-((diethoxyphosphoryl)methoxy)-4-(2,4-dioxo-3,4-dihydropyrimidin-1(2H)-yl)cyclopentyl) diisopropylphosphoramidite (Phosphoramidite 5').

Scheme 5

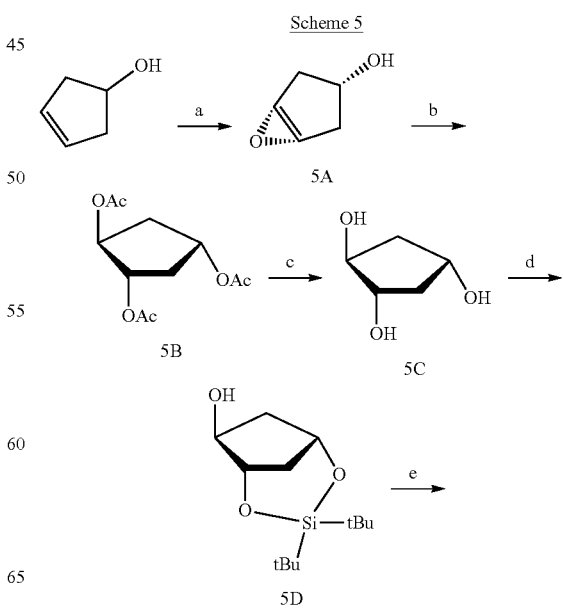

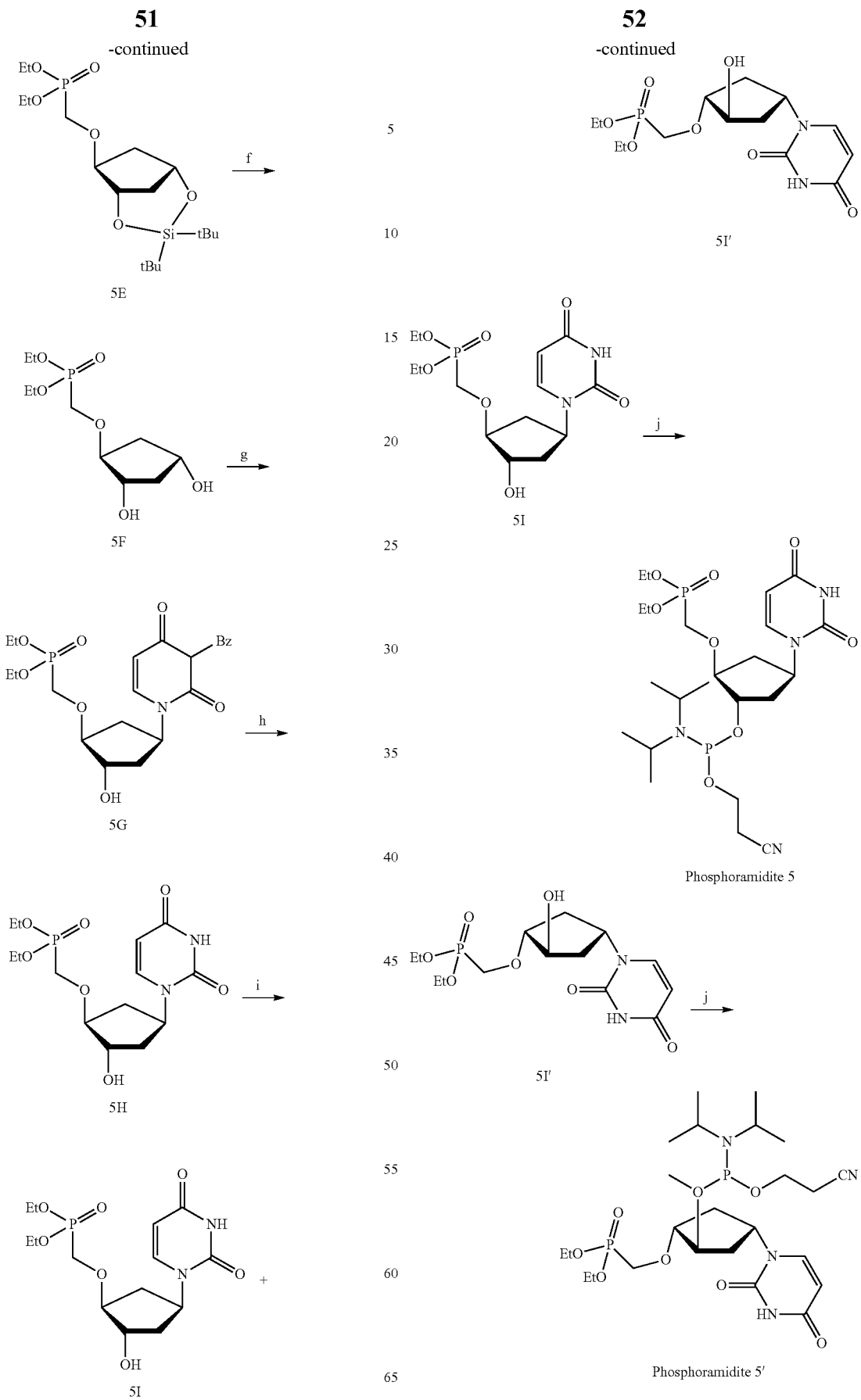

The reagents and conditions for synthesizing 5I and 5I' (steps a-i of Scheme 5) are disclosed in Drake et al., J. Chem. Soc., Perkin Trans. 1, 1996, 2739, and are as follows: a) m-CPBA, DCM; b) K$_2$CO$_3$, Ac$_2$O, H$_2$O, DMSO; c) K$_2$CO$_3$, MeOH d) t-BuSi(OTf)$_2$, Lutidine, DMF; e) (EtO)$_2$POCH$_2$OTf, n-BuLi, THF; f) NH$_4$F, MeOH; g) 3-benzoyl-2H-112-pyrimidine-2,4(3H)-dione; PPh$_3$, DIAD; h) NH$_4$OH, MeOH; and i) SFC separation. The final step involves reacting 5I and 5I' with j) 3-((chloro(diisopropylamino)phosphaneyl)oxy)propanenitrile, DIPEA, DCM to form Phosphoramidite 5 and Phosphoramidite 5I'.

$^1$H NMR (400 MHz, CDCl$_3$): δ 9.02 (br s, 1H), 7.62 (dd, J=1.6, 8.2 Hz, 1H), 5.62 (d, J=8.0 Hz, 1H), 5.32-5.14 (m, 1H), 4.46 (br d, J=9.4 Hz, 1H), 4.20-4.08 (m, 4H), 4.06-3.96 (m, 1H), 3.94-3.73 (m, 4H), 3.72-3.57 (m, 2H), 2.76-2.65 (m, 2H), 2.59-2.48 (m, 1H), 2.33-2.19 (m, 2H), 1.75 (br d, J=13.9 Hz, 1H), 1.32 (br t, J=7.0 Hz, 6H), 1.25-1.15 (m, 12H); $^{31}$P NMR (162 MHz, CD$_3$CN) δ 147.53, 20.45, 20.36; m/z found [M+H]$^+$=563.5

Example 6: Synthesis of Oligonucleotide Containing 4'-Oxymethylphosphonate at 5'-Terminus Using Dimethyl Phosphonate Ester Phosphoramidites Control Compound 5'-OH, 2'-F; Control Compound 5'-PO$_4$, 2'-F; Control Compound 5'-OH, 2'-OMe; and Control Compound 5'-PO$_4$, 2'-OMe (FIGS. 1A and 1C) were synthesized using 2'-modified nucleoside phosphoramidites, i.e., 2'-F and 2'OMe modified nucleoside phosphoramidites. Test Compound Fully Deprotected, 2'-F; Test Compound Monomethyl Protected, 2'-F; Test Compound Fully Deprotected, 2'OMe; and Test Compound Monomethyl Protected, 2'-OMe (FIGS. 1B and 1D) were also synthesized using 2'-F and 2'-OMe modified nucleoside phosphoramidites. Each compound contains a 22 nucleotide guide strand and a 36 nucleotide passenger strand, where the passenger strand contains four nucleotides in the tetraloop that are each conjugated to a polyethylene glycol-GalNAc ligand. See FIGS. 1A-D. The control and test compounds share the same primary sequences targeting gene A mRNA, identical passenger strands, and the same chemical modification pattern on the guide strands except for nucleotide position 1, where certain compounds contain 2'-F and others contain 2'-OMe, and where each test compound contains a phosphate analog (a 4'-oxymethylphosphonate) that is not present in the control compounds. See FIGS. 1A-D. All of the nucleotides in each compound were modified at the 2'-carbon of the sugar ring.

Oligonucleotide synthesis was carried out on a solid support in the 3' to 5' direction using a commercial oligo synthesizer. Standard oligo synthesis protocols were employed. The coupling time was 300 seconds with 5-ethylthio-1H-tetrazole (ETT) as an activator. Iodine solution was used for phosphite triester oxidation.

To synthesize the guide strand of the test compounds with a phosphate analog on the N1 nucleotide of the guide strand, a 2'-modified nucleoside phosphoramidite containing a 4'-oxymethylphosphonate was coupled to the 5'-terminus of each guide strand. More specifically, Phosphoramidite 3 (Example 3) or Phosphoramidite 4 (Example 4), represented below, was coupled to the 5'-terminus of the guide strand of each test compound.

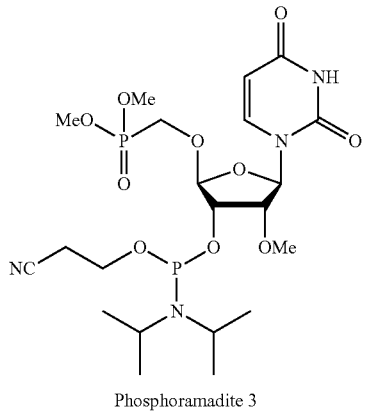

Phosphoramadite 3

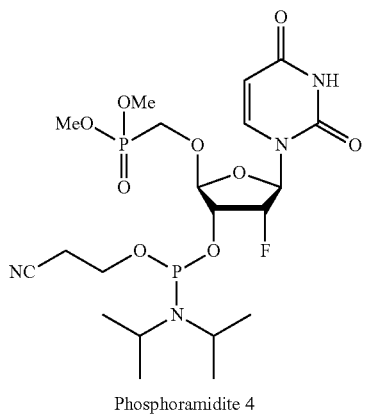

Phosphoramidite 4

The phosphonate groups of Phosphoramidite 3 and Phosphoramidite 4 each contain two methyl protected oxygen atoms. Depending on the deprotection step used, however, either one or both of the methyl groups are removed, resulting in a 5'-terminal nucleotide with one methyl protected oxygen atom in the phosphonate group, as represented in Test Compound Monomethyl Protected, 2'-F and Test Compound Monomethyl Protected, 2'-OMe (See FIGS. 1B and 1D) or a fully deprotected phosphonate group (with no methyl protected oxygen atoms), as represented in both Test Compound Fully Deprotected, 2'-F and Test Compound Fully Deprotected, 2'-OMe (See FIGS. 1B and 1D).

A monomethyl protected 4'-oxymethylphosphonate oligonucleotide can be prepared using ammonia. To prepare the guide strands of Test Compound Monomethyl Protected, 2'-F and Test Compound Monomethyl Protected, 2'-OMe, the solid-support-bound oligonucleotide to which Phosphoramidite 3 or 4 had been coupled was suspended in mixture of concentrated ammonia (28-30 wt %) and heated at 55° C. for 17 hours to complete cleavage from solid support and removal of protecting groups on the oligonucleotide, including one methyl group of the phosphonate group. The 5'-terminal nucleotide of the guide strand of Test Compound Monomethyl Protected, 2'-F and Test Compound Monomethyl Protected, 2'-OMe (See FIGS. 1B and 1D) is shown below, where R is F and OMe, respectively.

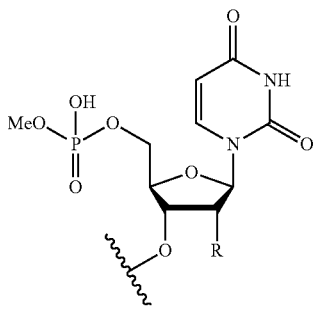

A fully deprotected 4'-oxymethylphosphonate oligonucleotide can be prepared using trimethylsilyl iodide reagent ("TMSI"). To prepare the guide strands of Test Compound Fully Deprotected, 2'-F and Test Compound Fully Deprotected, 2'-OMe, the solid-support bound oligonucleotides to which Phosphoramidite 3 or 4 had been coupled were treated with TMSI/pyridine solution in $CH_2Cl_2$ at room temperature. After 30-45 minutes, the reaction was quenched with 1M 2-mercaptoethanol solution in TEA/$CH_3CN$ (1:1). Standard oligonucleotide procedures for deprotection and cleavage from solid support were applied after TMSI step to give the fully deprotected 4'-oxymethylphosphonate oligonucleotide guide strands. The 5'-terminal nucleotide of the guide strand of Test Compound Fully Deprotected, 2'-F and Test Compound Fully Deprotected, 2'-OMe (See FIGS. 1B and 1D) is shown below, where R is F and OMe, respectively.

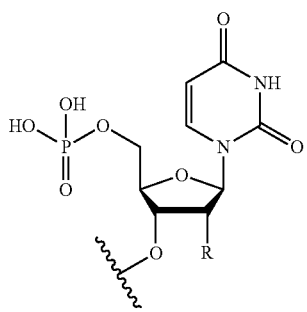

Following deprotection and cleavage, the crude oligonucleotides were analyzed and purified by high performance liquid chromatography (HPLC) (Integrated DNA Technologies, Coralville, Iowa). The obtained oligonucleotide solutions were pooled and concentrated and were desalted with water. Finally, oligonucleotides were lyophilized to a powder.

The above-described process was then repeated to prepare complementary oligonucleotide passenger strands having a monovalent, GalNAc-conjugated nucleotide at each of nucleotide positions 27-30. GalNAc-conjugated phosphoramidite synthons were prepared using either click chemistry or an acetal linker to attach a GalNAc ligand to the 2'-carbon using methods known in the art (see, e.g., WO 2016/100401). The GalNAc-conjugated phosphoramidite synthons were incorporated into four successive positions (27-30) of the passenger strands. The passenger strands did not contain a 4'-oxymethylphosphonate.

Duplexes were formed by mixing each of the two complementary strands (guide and passenger) in a 1:1 molar ratio to obtain four dsRNAi inhibitor molecules: Test Compound Fully Deprotected, 2'-F; Test Compound Monomethyl Protected, 2'-F; Test Compound Fully Deprotected, 2'-OMe; and Test Compound Monomethyl Protected, 2'-OMe. See FIGS. 1B and 1D.

Four control dsRNAi inhibitor molecules (Control Compound 5'-OH, 2'-F; Control Compound 5'-$PO_4$, 2'-F; Control Compound 5'-OH, 2'-OMe; and Control Compound 5'-$PO_4$, 2'-OMe) were also prepared as described above except that none of the nucleotides in the control compounds included a 4'-oxymethylphosphonate. See FIGS. 1A and 1C. Control Compound 5'-$PO_4$, 2'-F and Control Compound 5'-$PO_4$, 2'-OMe were synthesized with natural phosphate (5'-$PO_4^{2-}$) at the 5'-carbon of the 5'-terminal nucleotide of the guide strand, whereas Control Compound 5'-OH, 2'-F and Control Compound 5'-OH, 2'-OMe contained a free hydroxyl group (5'-OH) at the 5'-carbon of the 5'-terminal nucleotide of the guide strand.

Example 7: Synthesis of an Oligonucleotide Containing 4'-Oxymethylphosphonate at 5'-Terminus Using Diethyl Phosphonate Ester Phosphoramidites The oligonucleotide synthesis procedures described in Example 6 were also repeated with diethyl phosphonate ester phosphoramidites to synthesize additional dsRNA inhibitor molecules. More specifically, Phosphoramidite 1 (Example 1) or Phosphoramidite 2 (Example 2), represented below, was coupled to the 5'-terminus of an oligonucleotide guide strand.

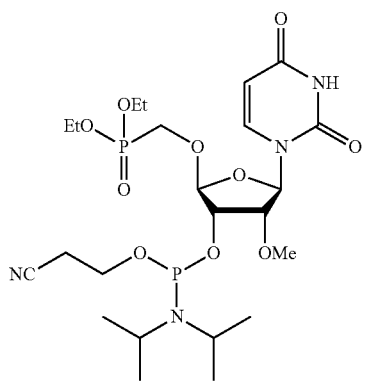

Phosphoramidite 1

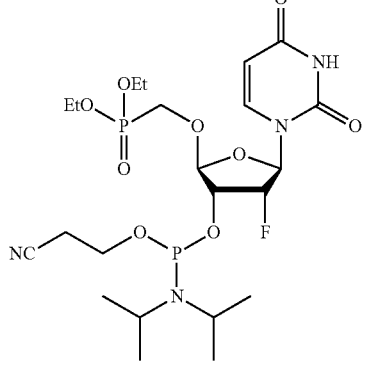

Phosphoramidite 2

The phosphonate groups of Phosphoramidite 1 and Phosphoramidite 2 each contain two ethyl protected oxygen atoms. Depending on the deprotection step used, however, either one or both of the ethyl groups are removed, resulting in a 5'-terminal nucleotide with one ethyl protected oxygen atom in the phosphonate group or a fully deprotected phosphonate group (with no ethyl protected oxygen atoms).

A monoethyl protected 4'-oxymethylphosphonate oligonucleotide can be prepared using ammonia. To prepare an oligonucleotide guide strand with a monoethyl protected 5'-terminal nucleotide, the solid-support-bound oligonucleotide to which Phosphoramidite 1 or 2 had been coupled was suspended in mixture of concentrated ammonia (28-30 wt %) and heated at 55° C. for 17 hours to complete cleavage from solid support and removal of protecting groups from the oligonucleotide, including one ethyl group of the phosphonate group. The 5'-terminal nucleotide of the guide strand having a monoethyl protected phosphonate group is shown below.

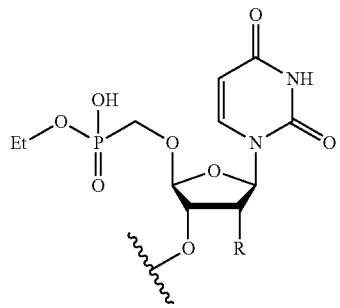

A fully deprotected 4'-oxymethylphosphonate oligonucleotide can be prepared using trimethylsilyl iodide reagent ("TMSI"). To prepare an oligonucleotide guide strand with a fully deprotected 5'-terminal nucleotide, the solid-support bound oligonucleotide to which Phosphoramidite 1 or 2 had been coupled was treated with TMSI/pyridine solution in $CH_2Cl_2$ at room temperature. After 30-45 minutes, the reaction was quenched with 1M 2-mercaptoethanol solution in $TEA/CH_3CN$ (1:1). Standard oligonucleotide procedures for deprotection and cleavage from solid support were applied after TMSI step to give the fully deprotected 4'-oxymethylphosphonate oligonucleotide guide strand. The 5'-terminal nucleotide of the fully deprotected guide strand is shown below.

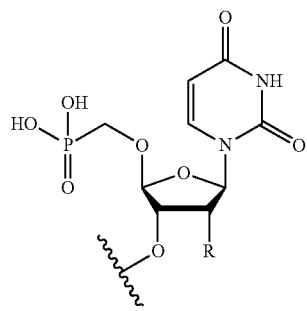

Following deprotection and cleavage, the crude oligonucleotides were analyzed and purified by high performance liquid chromatography (HPLC) (Integrated DNA Technologies, Coralville, Iowa). The obtained oligonucleotide solutions were pooled and concentrated and were desalted with water. Finally, oligonucleotides were lyophilized to a powder.

The above-described process was then repeated to prepare complementary oligonucleotide passenger strands having a monovalent, GalNAc-conjugated nucleotide at each of nucleotide positions 27-30. GalNAc-conjugated phosphoramidite synthons were prepared using click chemistry or an acetal linker to attach a GalNAc ligand to the 2'-carbon using methods known in the art (see, e.g., WO 2016/100401). The GalNAc-conjugated phosphoramidite synthons were incorporated into four successive positions (27-30) of the passenger strands. The passenger strands did not contain a 4'-oxymethylphosphonate.

Duplexes were formed by mixing each of the two complementary strands (guide and passenger) in a 1:1 molar ratio to obtain dsRNAi inhibitor molecules. Each dsRNAi inhibitor molecule contains a 22-base pair guide strand having a 4'-oxymethylphosphonate at nucleotide position 1 and a 36-base pair passenger strand without any 4'-oxymethylphosphonate, where the passenger strand contains four nucleotides in the tetraloop that are each conjugated to a polyethylene glycol-GalNAc ligand.

Example 8: In Vitro Potency ($IC_{50}$) of Test Compounds Transfected Into Cells Using a Cationic Lipid Transfection Agent The dsRNAi inhibitor molecules prepared in Example 6 were reverse transfected into HEK293 cells using LIPOFECTAMINE® RNAiMax (Thermo Fisher Scientific Inc., Rockville, MD) in a 96-well plate as per manufacturer's protocol. LIPOFECTAMINE® RNAiMax (Thermo Fisher Scientific Inc., Rockville, MD) is a cationic lipid formulation designed to enhance the transfection efficiency of RNAi inhibitor molecules across a variety of cell types. The HEK293 cells were also transfected with a gene A plasmid. The final concentration of the dsRNAi inhibitor molecules ranged from 1000 pM to 0.0128 pM. HEK293 cells were added to the 96-well plates at 12000 cells/well, and the plates were incubated at 37° C. for 48 hours. After 48 hours, the cells were lysed by adding 30 µl of ISCRIPT™ lysis buffer (Bio-Rad Laboratories, Hercules, CA) per well. Next, 22 µl of the lysate was transferred to a fresh plate and cDNA was prepared using the High-Capacity cDNA Reverse Transcription Kit (Applied Biosystems Corporation, Carlsbad, CA). Quantitative PCR was carried out with the target sequence normalized to the human SFRS9-F569 (HEX) gene at 55° C. Graphs were plotted using GraphPad Prism (GraphPad Software Inc., La Jolla, CA), and the $IC_{50}$ values were calculated.

Figure 2A:
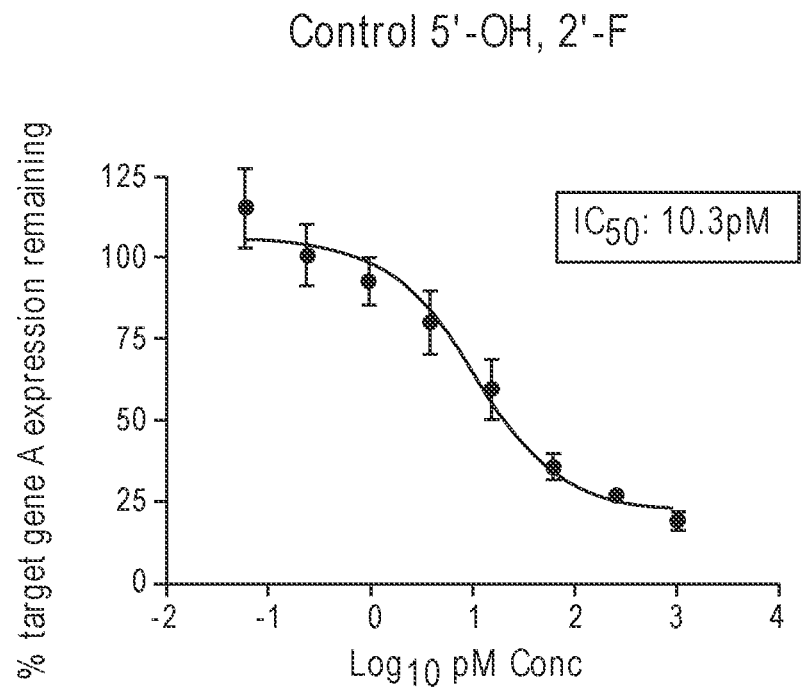
FIGS. 2A-D depict the potency ($IC_{50}$) of Test Compound Fully Deprotected, 2'-F (FIG. 2C) and Test Compound Monomethyl Protected, 2'-F (FIG. 2D) in comparison to Control Compound 5'-OH, 2'-F (FIG. 2A) and Control Compound 5'-$PO_4$, 2'-F (FIG. 2B), as measured by the knockdown of target gene A mRNA 48 hours after transfection of the compounds with LIPOFECTAMINE® RNAiMax (Thermo Fisher Scientific Inc., Rockville, MD) into HEK293 cells, as described in Example 8.
Figure 2B:
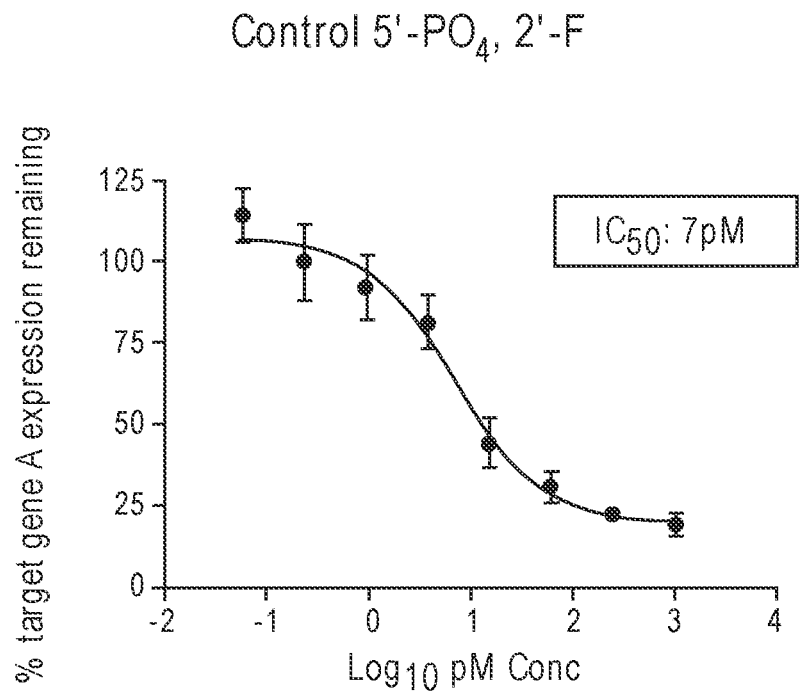
Figure 2C:
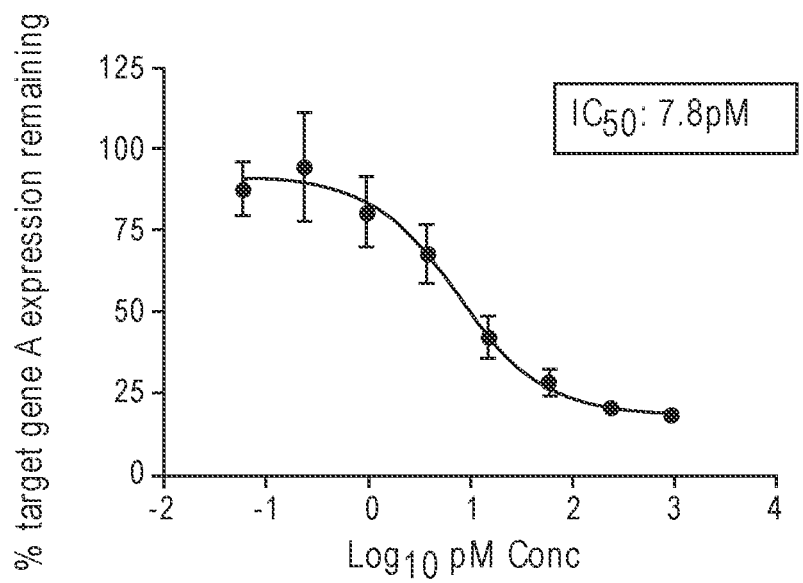
Figure 2D:
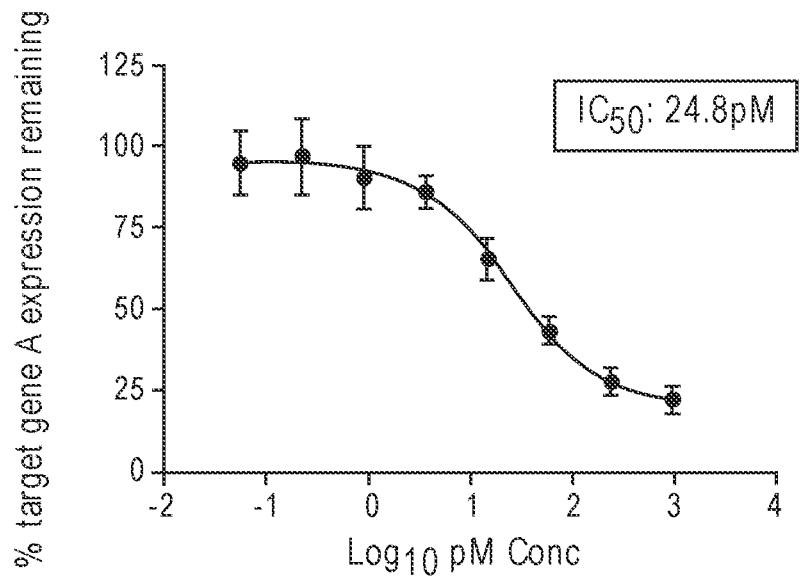

FIGS. 2A-D depict the in vitro activity of Control Compound 5'-OH, 2'-F; Control Compound 5'-$PO_4$, 2'-F; Test Compound Fully Deprotected, 2'-F; and Test Compound Monomethyl Protected, 2'-F following transfection into HEK293 cells using LIPOFECTAMINE® RNAiMax (Thermo Fisher Scientific Inc., Rockville, MD). Control Compound 5'-OH, 2'-F with a 5'-OH had an $IC_{50}$ of about 10.3 pM, which was comparable to the activity ($IC_{50}$ of 7 pM) of Control Compound 5'-$PO_4$, 2'-F, having a 5'-$PO_4$ instead of a 5'-OH. FIGS. 2A-B. Because a 5'-$PO_4$ is believed to be important for Ago2 loading, these results suggest that the 5'-OH of Control Compound 5'-OH, 2'-F was converted to a 5'-$PO_4$ by a kinase in the cytosol of the transfected cells. Test Compound Fully Deprotected, 2'-F had similar activity ($IC_{50}$ of 7.8 pM) to the control compounds, indicating that the fully deprotected 4'-oxymethylphosphonate is an efficient phosphate analog. FIG. 2C. Test Compound Monomethyl Protected, 2'-F showed lower activity ($IC_{50}$ of 24.8 pM) in this assay than Test Compound Fully Deprotected, 2'-F ($IC_{50}$ of 7.8 pM), which may be attributed to inefficient removal of the methyl protecting group of Test Compound Monomethyl Protected, 2'-F under these assay conditions. FIG. 2D. Without intending to be bound by any theory, it is believed that removal of the methyl protecting group from the 4'-oxymethylphosphonate of Test Compound Monomethyl Protected, 2'-F (yielding a fully deprotected 4'-oxymethylphosphonate) allows for more efficient Ago2 loading.

Example 9: In Vitro Potency of Test Compounds Transfected Into Monkey Hepatocytes Without Using a Cationic Lipid Transfection Agent Primary monkey hepatocytes were obtained from Life Technologies Corporation (Carlsbad, CA) and thawed and plated as per manufacturer's protocol in CORNING® BIO-COAT™ 96 well plates. After 4-6 hours of plating, the media was replaced with 90 μl of Williams E incubation media per well. Test Compound Fully Deprotected, 2'-F and Test Compound Monomethyl Protected, 2'-F were serially diluted starting with a concentration of 1 μM to 12.8 μM (5-fold reduction). 10 μl of the test compounds were added to the respective wells in the absence of a cationic lipid transfection agent, such as LIPOFECTAMINE® (Thermo Fisher Scientific, Inc.) The plate was incubated at 37° C. for 24 hours and knockdown of an RNA target was tested. Target RNA was extracted and purified using SV96 Total RNA Isolation System (Promega, Madison, WI) as per the manufacturer's protocol. cDNA was prepared using the High-Capacity cDNA Reverse Transcription Kit (Applied Biosystems Corporation, Carlsbad, CA). Quantitative PCR was carried out at 60° C. with the RNA target normalized to *Homo sapiens* peptidyl prolyl isomerase B PPIB. Graphs were plotted using the GraphPad Prism software (GraphPad Software Inc., La Jolla, CA) and the $IC_{50}$ values were calculated.

Figure 3A:
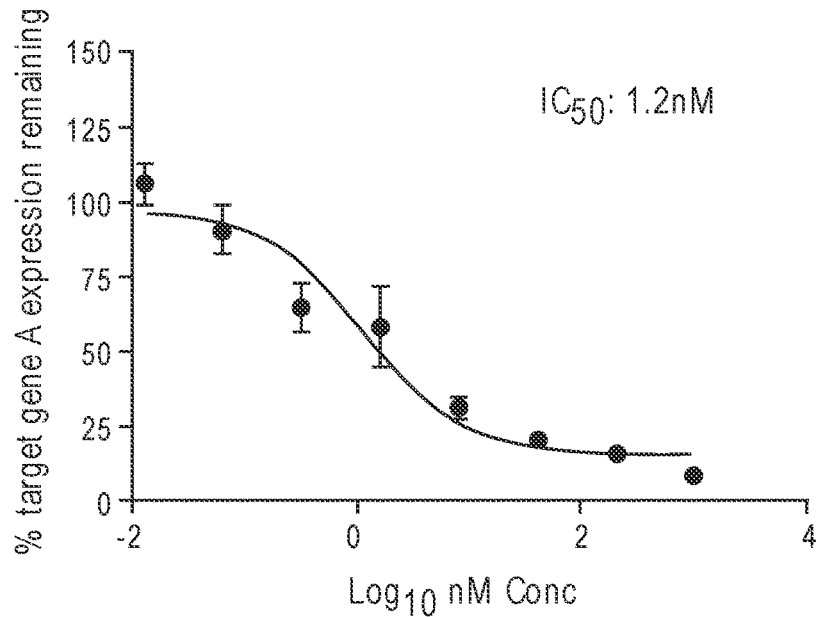
FIGS. 3A-B depict the potency ($IC_{50}$) of Test Compound Fully Deprotected, 2'-F (FIG. 3A) and Test Compound Monomethyl Protected, 2'-F (FIG. 3B) in monkey hepatocytes, as measured by the knockdown of target gene A mRNA at 24 hours following transfection without a cationic lipid transfection agent, as described in Example 9.
Figure 3B:
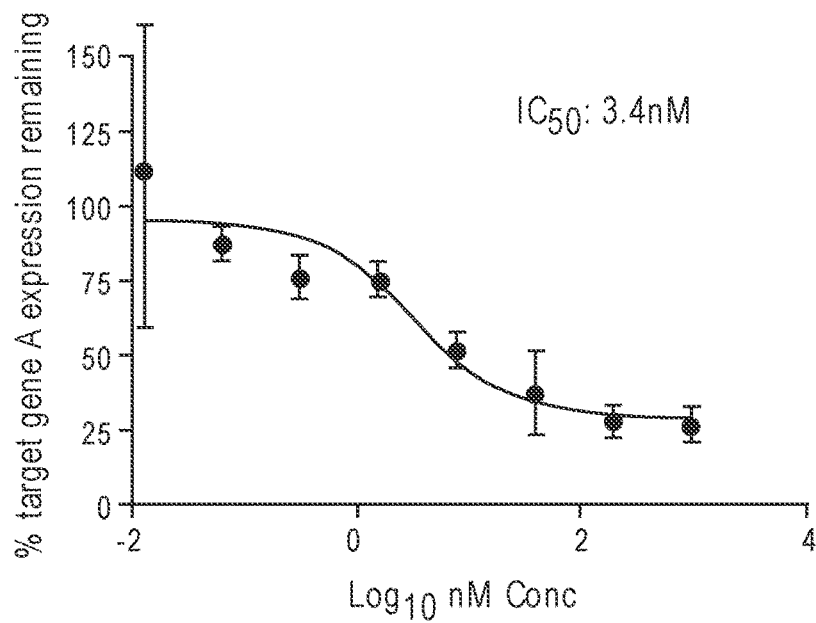

FIGS. 3A-B depict the activity of Test Compound Fully Deprotected, 2'-F and Test Compound Monomethyl Protected, 2'-F in primary monkey hepatocytes following transfection without a cationic lipid transfection agent ("self-delivery"). It is believed that these conditions more closely represent the in vivo conditions encountered by dsRNAi inhibitor molecules than the transfection protocol used in Example 8. More specifically, it is believed that without a transfection agent, such as LIPOFECTAMINE® RNAiMax (Thermo Fisher Scientific Inc., Rockville, MD), which can function to sequester and protect the oligonucleotides, the dsRNAi inhibitor molecules may experience more direct exposure to the enzymes and conditions of the endosomal compartment of the cells. This could lead, for example, to more efficient removal of the methyl protecting group of Test Compound Monomethyl Protected, 2'-F in comparison to the lipid transfection described in Example 8. Consistent with this, Test Compound Fully Deprotected, 2'-F and Test Compound Monomethyl Protected, 2'-F showed comparable activity ($IC_{50}$ 1.2 nM and $IC_{50}$ 3.4 nM) following the self-delivery transfection protocol. FIGS. 3A-B.

Example 10: In Vitro Potency of Test Compounds Transfected Into Human Hepatocytes Without Using a Cationic Lipid Transfection Agent Cryopreserved human hepatocytes (Triangle Research Laboratories, Durham, NC; lot #HUM41111B) were thawed and plated in hepatocyte plating medium (Triangle Research Laboratories) according to the manufacturer's instructions, in 96 well collagen I coated plates (BD Biosciences). After 4 hours the medium was changed to serum-free maintenance medium (Triangle Research Laboratories, Durham, NC). Test Compound Fully Deprotected, 2'-F and Test Compound Monomethyl Protected, 2'-F were serially diluted, starting with a concentration of 1p M to 0.13 nM; added to the medium; and incubated for 24 hours in the absence of a cationic lipid transfection agent, such as LIPOFECTAMINE® (Thermo Fisher Scientific, Inc.). The next day, the medium was renewed and the cells were grown for an additional 24 hours.

After the incubation period, cells were lysed and RNA was prepared using the SV96 Total RNA Isolation System (Promega, Madison, WI) as per the manufacturer's protocol. cDNA was prepared using the High-Capacity cDNA Reverse Transcription Kit (Applied Biosystems Corporation, Carlsbad, CA). Quantitative PCR was then performed using gene A specific primer-probes normalized to the housekeeping genes HPRT1 and IPO8. Gene A mRNA expression levels were normalized to mock-treated cells and the dose curve was plotted using the GraphPad Prism software (GraphPad Software Inc., La Jolla, CA). The $IC_{50}$ values were estimated using the three parameter model.

Figure 4A:
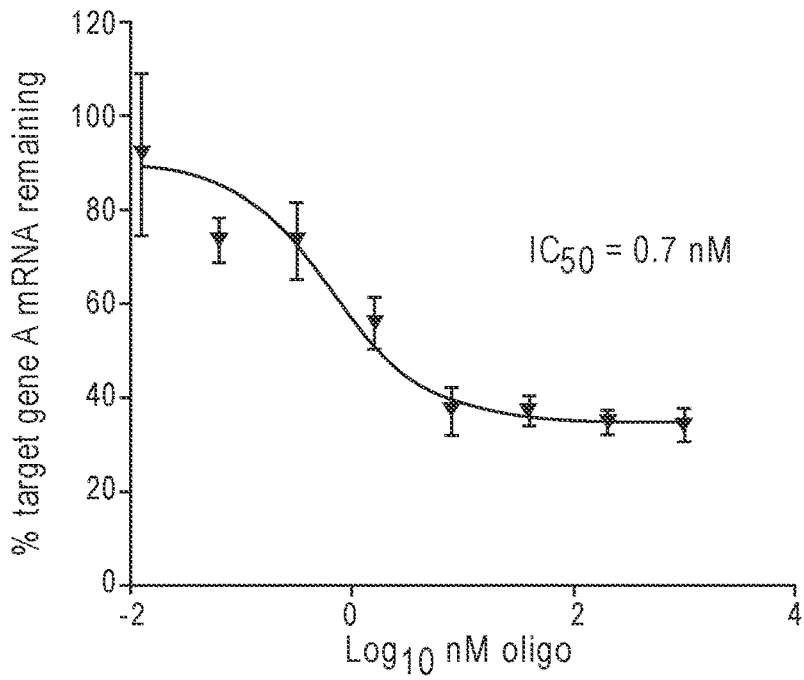
FIGS. 4A-B depict the potency ($IC_{50}$) of Test Compound Fully Deprotected, 2'-F (FIG. 4A) and Test Compound Monomethyl Protected, 2'-F (FIG. 4B) in human hepatocytes, as measured by the knockdown of target gene A mRNA at 48 hours following transfection without a cationic lipid transfection agent, as described in Example 10.
Figure 4B:
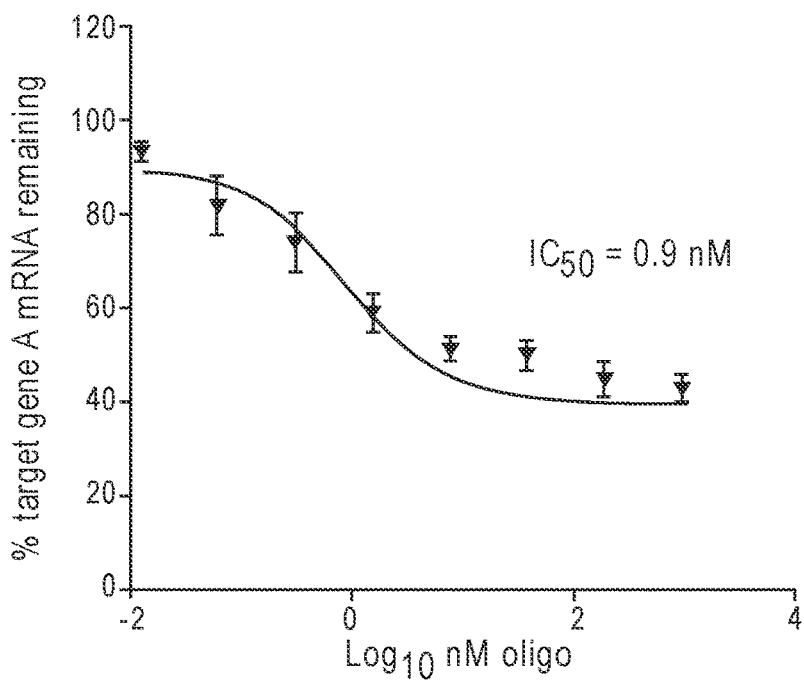

FIGS. 4A-B depict the activity of Test Compound Fully Deprotected, 2'-F and Test Compound Monomethyl Protected, 2'-F in primary human hepatocyte following transfection without a cationic lipid transfection agent. Analogous to the monkey hepatocyte self-delivery experiment above, it is believed that these conditions more closely resemble the in vivo conditions encountered by dsRNAi inhibitor molecules than the transfection protocol in Example 8. Consistent with the results in Example 9, both test compounds showed comparable activity ($IC_{50}$ 0.7 nM and $IC_{50}$ 0.9 nM), suggesting the methyl protecting group in Test Compound Monomethyl Protected, 2'-F may be more efficiently removed under these conditions to yield a fully deprotected phosphonate group, like the phosphonate group in Test Compound Fully Deprotected, 2'-F. FIGS. 4A-B.

Example 11: Stability of Test Compounds

To assess the stability of the 4'-oxymethylphosphonate compounds in vitro, 3 μM of Control Compound 5'-OH, 2'-OMe; Control Compound 5'-$PO_4$, 2'-OMe; and Test Compound Fully Deprotected, 2'-OMe were incubated in 1 mg/mL rat liver tritosomes (Sekisui Xenotech, Kansas City, KS). The rat liver tritosomes are lysosomes from rat liver cells that have been treated with Triton WR 1339 (also called Tyloxapol). The two control compounds and one test compound were subsequently extracted from the lysosomal matrix using 96-well/100 mg CLARITY® OTX™ cartridge SPE plates (Phenomenex, Torrance, CA) and a 96-well plate vacuum manifold per manufacturer's instructions. The eluents were evaporated using a TURBOVAP® (Biotage, Charlotte, NC) solvent evaporation unit and reconstituted in water and analyzed via LC-MS.

An ACQUITY UPLC® instrument (Waters Corporation, Milford, MA) was used to deliver mobile phases containing buffer additives at 0.4 mL/min with chromatographic separation accomplished using an ACQUITY UPLC® Oligonucleotide BEH C18 Column 1.7 μm particle sized reversed phase Ultra-Performance Liquid Chromatography (2.1×50 mm) column (Waters Corporation, Milford, MA). The column temperature was maintained at 70° C. and the sample injection volume used was 10 or 15 μL. A SYNAPT® G2S high-resolution time-of-flight mass spectrometer (Waters Corporation, Milford, MA) operating under negative ion mode and electrospray ionization (ESI) conditions was used to detect the control and test compounds and metabolites thereof. Zero charge-state molecular ion masses were obtained via charge-state deconvolution using PROMASS DECONVOLUTION™ software (Novatia, Newtown, PA). The control and test compounds and their metabolites were identified by comparison of experimentally determined masses to expected theoretical molecular weights.

Figure 5A:
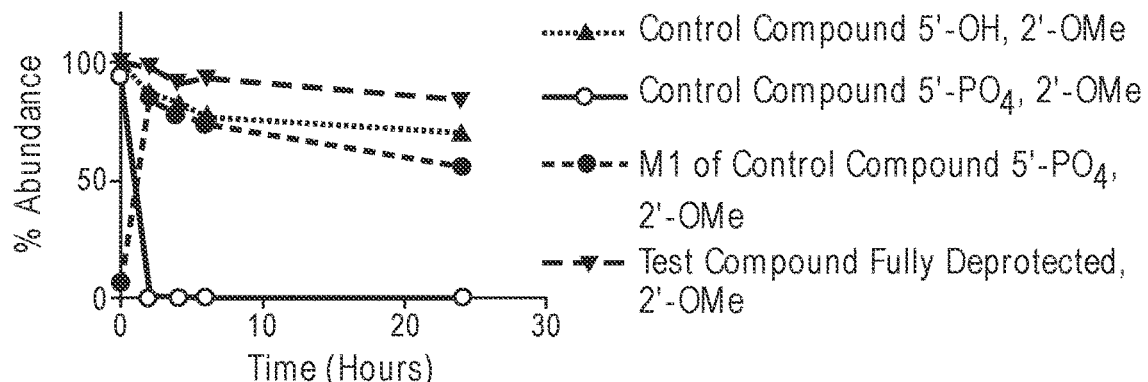
FIG. 5A depicts the relative abundance of the guide strands of Control Compound 5'-OH, 2'-OMe; Control Compound 5'-$PO_4$, 2'-OMe; Test Compound Fully Deprotected, 2'-OMe; and a metabolite of Control Compound 5'-$PO_4$, 2'-OMe having a 5'-OH instead of a 5'-$PO_4$ ("M1") following incubation in rat liver tritosomes, as described in Example 11.

FIG. 5A depicts the stability of the guide strand of the control and test compounds following incubation in the rat liver tritosomes. Phosphatases in the tritosomes can remove the 5'-$PO_4$ of Control Compound 5'-$PO_4$, 2'-OMe. Within 2 hours of incubation with the tritosomes, the guide strand of Control Compound 5'-$PO_4$, 2'-OMe could not be detected and was replaced by a metabolite ("M1") of the guide strand of the control compound having a 5'-OH instead of a 5'-$PO_4$. FIG. 5A. The chemical structure of the 5'-terminal nucleotide of the metabolite was the same as the chemical structure of the 5'-terminal nucleotide of the guide strand of Control Compound 5'-OH, 2'-OMe. During the 24 hour incubation period, no phosphonate cleavage from Test Compound Fully Deprotected, 2'-OMe was observed. Test Compound Fully Deprotected, 2'-OMe also showed improved metabolic stability as compared to Control Compound 5'-OH, 2'-OMe. FIG. 5A. These data suggest that a fully deprotected, 4'-oxymethylphosphonate located at the 5'-terminal nucleotide of the guide strand is resistant to phosphatase-mediated cleavage. A side-by-side comparison of the 5'-terminal nucleotides of Control Compound 5'-$PO_4$, 2'-OMe and Test Compound Fully Deprotected, 2'-OMe is shown below.

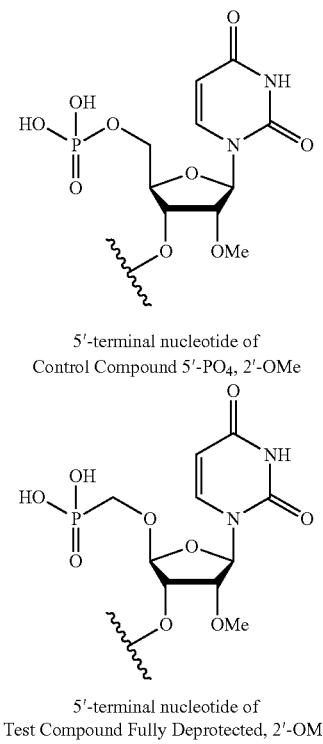

5'-terminal nucleotide of
Control Compound 5'-$PO_4$, 2'-OMe

5'-terminal nucleotide of
Test Compound Fully Deprotected, 2'-OMe

Figure 5B:
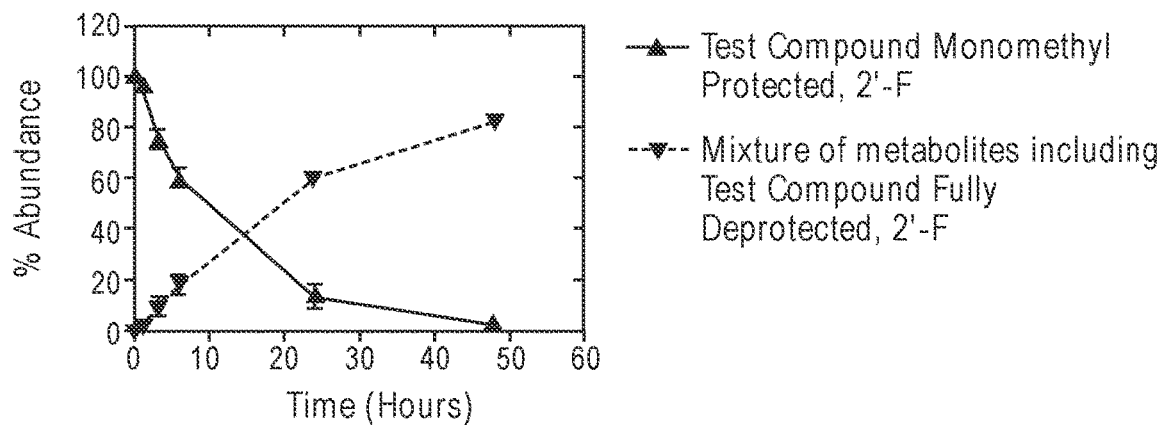
FIG. 5B depicts the relative abundance of the guide strands of Test Compound Monomethyl Protected, 2'-F and a mixture of metabolites thereof following incubation in rat liver tritosomes, as described in Example 11. The metabolite mixture includes a predominant metabolite having the same structure as the guide strand of Test Compound Fully Deprotected, 2'-F.

In a related experiment, 1.7 μM of Test Compound Monomethyl Protected, 2'-F was incubated in 1.2 U/mL (acid phosphatase activity) of rat liver tritosomes (Sekisui Xenotech, Kansas City, KS). Samples were extracted from the lysosomal matrix and analyzed for the presence of the test compound and related metabolites by UPLC as described above. Over time, the level of the guide strand of Test Compound Monomethyl Protected, 2'-F steadily decreased and was replaced in the sample by a mixture of metabolites, including a predominant species having the same structure as Test Compound Fully Deprotected, 2'-F, suggesting that the guide strand of Test Compound Monomethyl Protected, 2'-F was converted to the guide strand of Test Compound Fully Deprotected, 2'-F under these conditions. FIG. 5B. After 48 hours, the mixture of metabolites was present at about 80% of the original amount of Test Compound Fully Monomethyl Protected, 2'-F, indicating that the fully deprotected, 4'-oxymethylphosphonate located at the 5'-terminal nucleotide of the guide strand is resistant to phosphatase-mediated cleavage. FIG. 5B.

To assess the stability of the 4'-oxymethylphosphonate compounds in vivo, two male CD-1 mice were dosed with Test Compound Monomethyl Protected, 2'-OMe at 3 mpk and, at each time point, livers were processed, and analyzed by reversed-phase ion-pairing ultra performance liquid chromatography (RP-IP-UPLC) and high resolution mass spectrometry (HRMS). Frozen tissues were transferred into Covaris TissueTube Extra Thick pulverization bags (Covaris, Woburn, MA), snap frozen in liquid nitrogen, and pulverized with the Cryoprep Pulverizer (Covaris, Woburn, MA). Samples were then returned to Safe-Lock Tubes (Eppendorf, Hauppauge, NY) and 1 mL CLARITY® OTX™ Lysis-Loading Buffer (Phenomenex, Torrance, CA) was added. Tissue was homogenized using the TissueLyser II (Qiagen, Frederick, MD) at 30 Hz for 3 min. Samples were then centrifuged at 20,000 rpm for 15 min at 4° C. Test Compound Monomethyl Protected, 2'-F and its metabolites were extracted from the supernatant using the 96-well 100 mg Clarity® OTX™ (Phenomenex, Torrance, CA) solid phase extraction plate per the manufacturer's protocol. The final eluent was frozen, lyophilized, and resuspended in 80 uL of water to be analyzed by RP-IP-UPLC-HRMS.

An ACQUITY UPLC® instrument (Waters Corporation, Milford, MA) was used to deliver mobile phases containing buffer additives at 0.4 mL/min with chromatographic separation accomplished using an ACQUITY UPLC® Oligonucleotide BEH C18 Column 1.7 μm particle sized reversed phase Ultra-Performance Liquid Chromatography (2.1×50 mm) column (Waters Corporation, Milford, MA). The column temperature was maintained at 70° C. and the sample injection volume used was 40 μL. A SYNAPT® G2S high-resolution time-of-flight mass spectrometer (Waters Corporation, Milford, MA) operating under negative ion mode and electrospray ionization (ESI) conditions was used to detect the guide strand of Test Compound Monomethyl Protected, 2'-F and metabolites thereof. Zero charge-state molecular ion masses were obtained via charge-state deconvolution using PROMASS DECONVOLUTION™ software (Novatia, Newtown, PA). The guide strand of Test Compound Monomethyl Protected, 2'-OMe and their metabolites were identified by comparison of experimentally determined masses to expected theoretical molecular weights. Signal intensities for the guide strand of Test Compound Monomethyl Protected, 2'-OMe and related metabolites were calculated by PROMASS DECONVOLUTION™ software and are derived from the charge-state deconvoluted signal intensity.

Figure 5C:
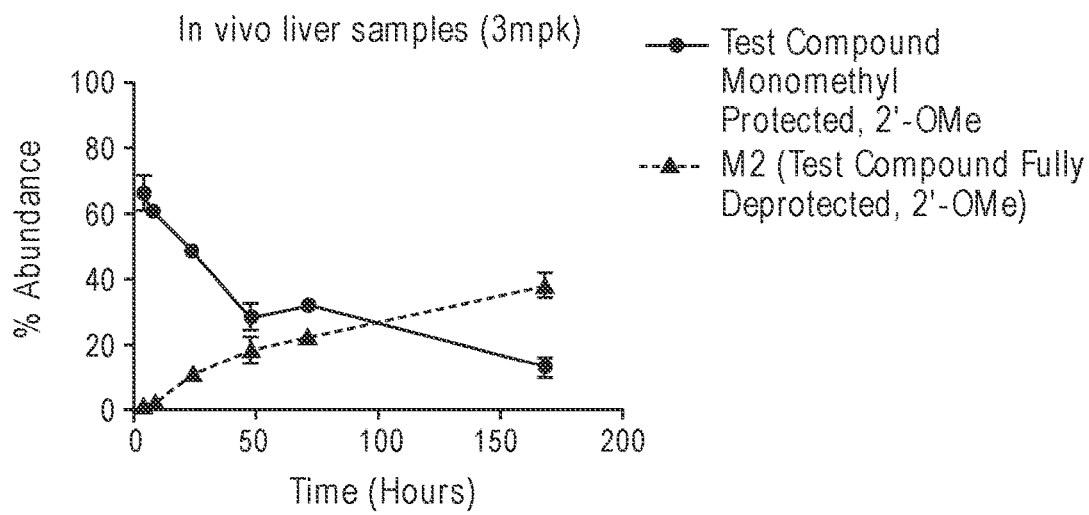
FIG. 5C depicts the relative abundance of the guide strands of Test Compound Monomethyl Protected, 2'-OMe and a metabolite thereof ("M2") in mouse liver samples following the in vivo administration of 3 milligram per kilogram body weight ("mpk") of Test Compound Monomethyl Protected, 2'-OMe, as described in Example 11. M2 has the same structure as the guide strand of Test Compound Fully Deprotected, 2'-OMe.

By 48 hours, the amount of the guide strand of Test Compound Monomethyl Protected, 2'-OMe had steadily decreased to about 30%. FIG. 5C. As the amount of the guide strand of Test Compound Monomethyl Protected, 2'-OMe decreased, a metabolite (M2) having the same structure as Test Compound Fully Deprotected, 2'-OMe, steadily increased, reaching about 20% at 50 hours and over 30% at 175 hours, suggesting that the methyl group of the 4'-oxymethylphosphonate was converted to a hydroxyl group in vivo. FIG. 5C.

Example 12: In Vivo Activity of Test Compounds in Mice

CD-1 female mice were dosed subcutaneously at a volume of 10 µL/g using the dosage levels and double-stranded nucleic acid inhibitor molecules described below. A control group was dosed with phosphate buffered saline (PBS). Animals were sacrificed 72 or 240 hours post-treatment. The left medial lobe of the liver was removed and a 1-4 mm punch was removed and placed into a 96-well plate on dry ice. Reduction of target mRNA was measured by qPCR using CFX384 TOUCH™ Real-Time PCR Detection System (BioRad Laboratories, Inc., Hercules, CA). All samples were normalized to the PBS treated control animals and plotted using GraphPad Prism software (GraphPad Software Inc., La Jolla, CA).

Figure 1B:
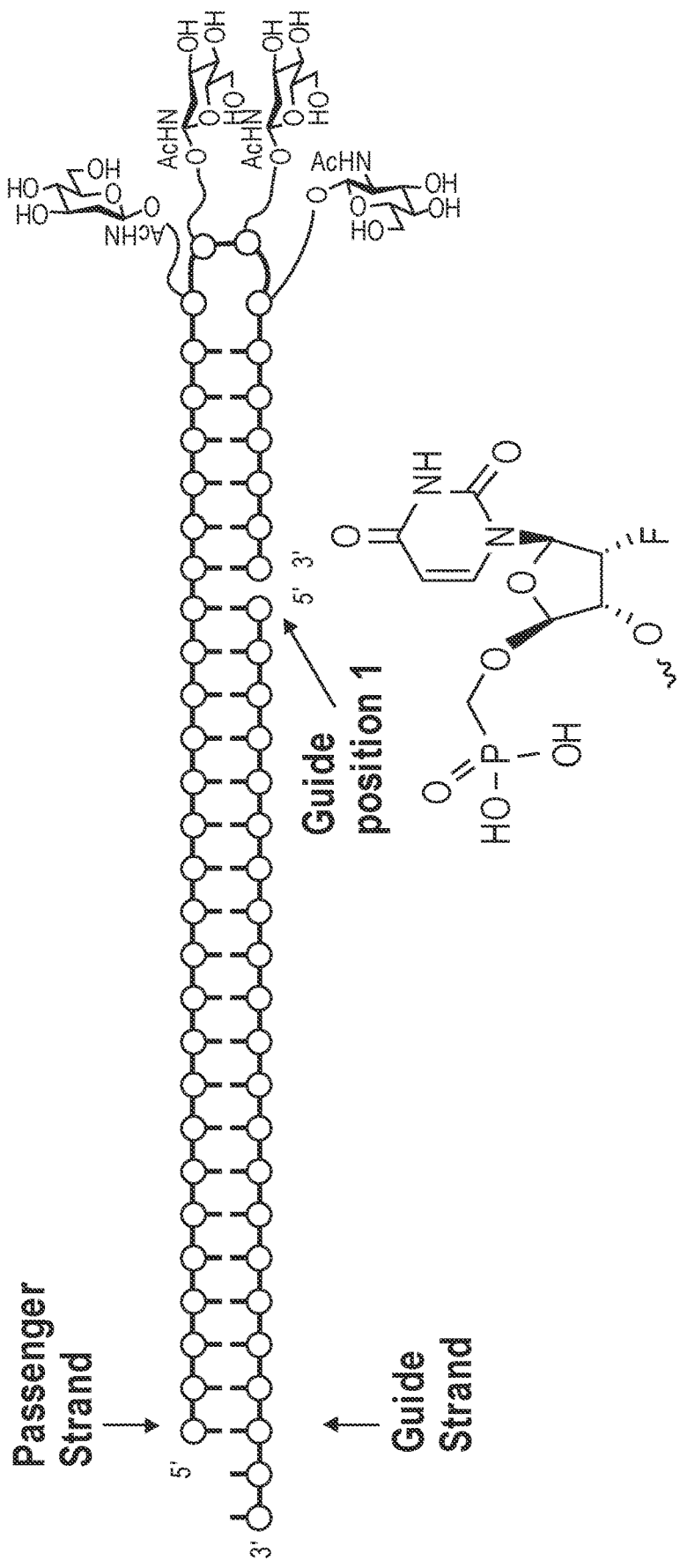
FIG. 1B depicts two representative double stranded RNAi inhibitor molecules as described in the Examples: Test Compound Fully Deprotected, 2'-F and Test Compound Monomethyl Protected, 2'-F. Test Compound Fully Deprotected, 2'-F and Test Compound Monomethyl Protected, 2'-F are identical except for the 4'-oxymethylphosphonate group on the N1 nucleotide of the guide strand with the former test compound having a fully deprotected phosphonate group and the latter test compound having a monomethyl protecting group on the phosphonate moiety. Test Compound Fully Deprotected, 2'-F and Test Compound Monomethyl Protected, 2'-F are identical to Control Compound 5'-OH, 2'-F and Control Compound 5'-$PO_4$, 2'-F (FIG. 1A) except for the N1 nucleotide of the guide strands, with the control compounds having either a 5'-OH or a 5'-$PO_4$ and the test compounds having a 4'-oxymethylphosphonate.
Figure 1B:
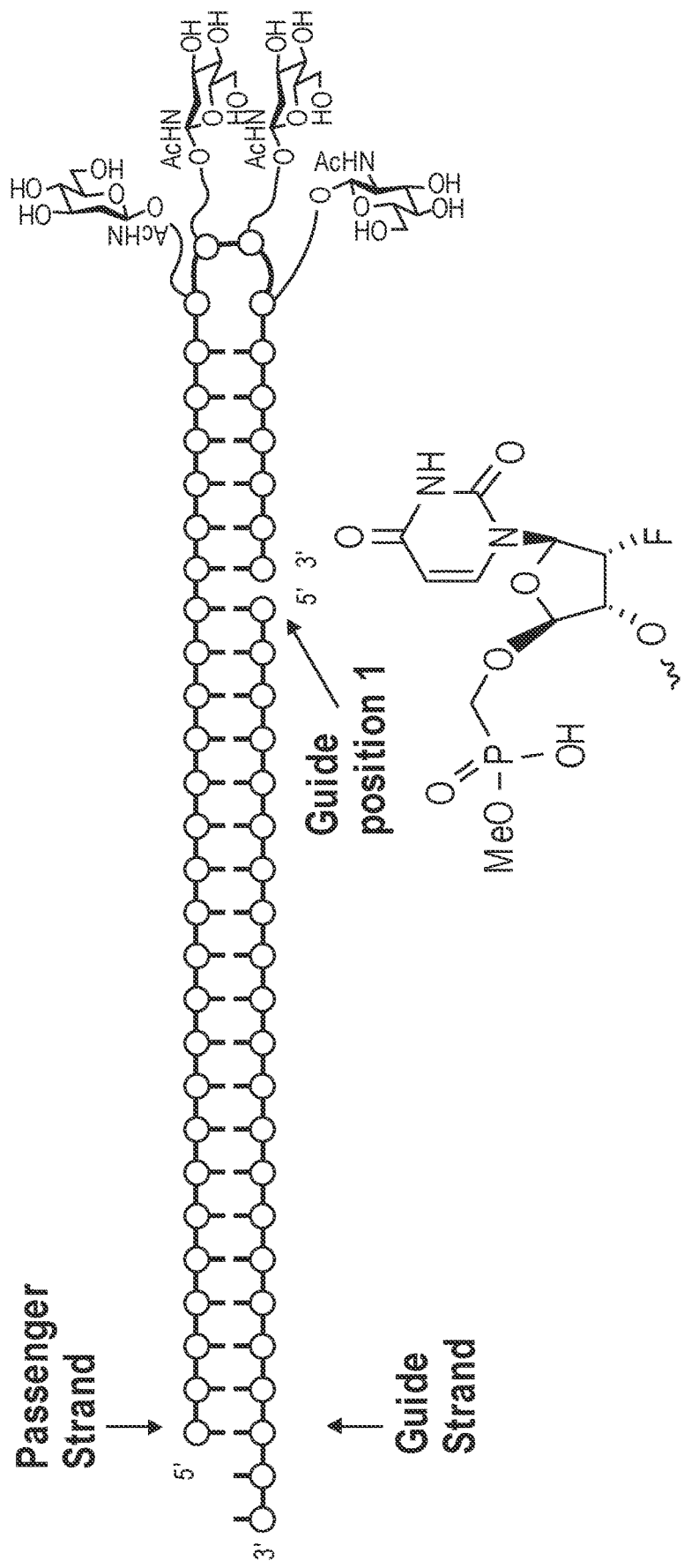
Figure 6A:
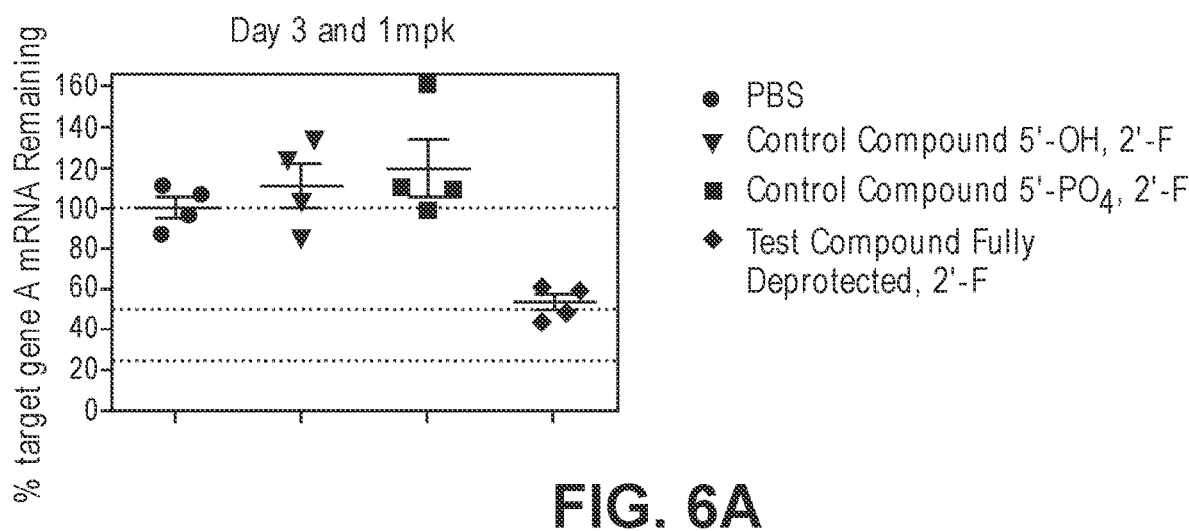
FIG. 6A depicts the potency in mice, as measured by the knockdown of target gene A mRNA, 3 days after the in vivo administration of 1 milligram per kilogram body weight ("mpk") of Control Compound 5'-OH, 2'-F; Control Compound 5'-$PO_4$, 2'-F; or Test Compound Fully Deprotected, 2'-F in comparison to a control PBS injection, as described in Example 12.

In a first experiment, the mice were dosed subcutaneously at 1 mpk with Control Compound 5'-OH, 2'-F; Control Compound 5'-PO$_4$, 2'-F; and Test Compound Fully Deprotected, 2'-F. These three compounds are identical except for the nucleotide at position of 1 of the guide strand, as shown in FIGS. 1A and 1B, with the control compounds having a 5'-OH or 5'-PO$_4$ group and the test compound having a fully deprotected, 4'-oxymethylphosphonate. The inhibition of target gene A mRNA expression was measured at day 3 after dosing. Test Compound Fully Deprotected, 2'-F showed significantly improved gene silencing activity as compared to the two control compounds at the same dose. FIG. 6A. These data demonstrate that a metabolically stable 4'-oxymethylphosphonate improves the in vivo activity of RNAi inhibitor molecules.

Figure 1C:
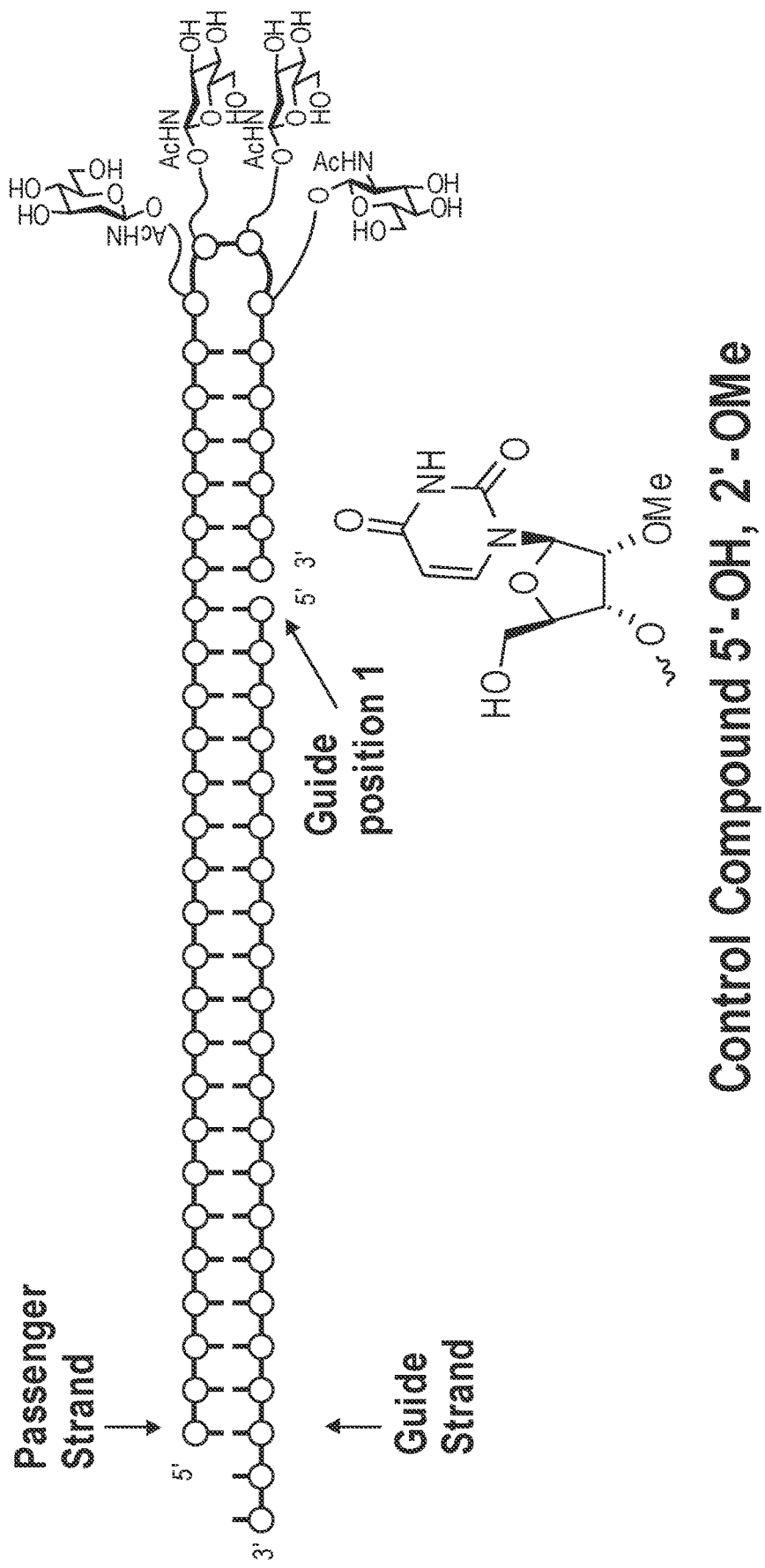
FIG. 1C depicts two representative control double stranded RNAi inhibitor molecules as described in the Examples: Control Compound 5'-OH, 2'-OMe and Control Compound 5'-$PO_4$, 2'-OMe. Control Compound 5'-OH, 2'-OMe and Control Compound 5'-$PO_4$, 2'-OMe are identical except for the 5'-OH or 5'-$PO_4$ of the N1 nucleotide of the guide strand.
Figure 1C:
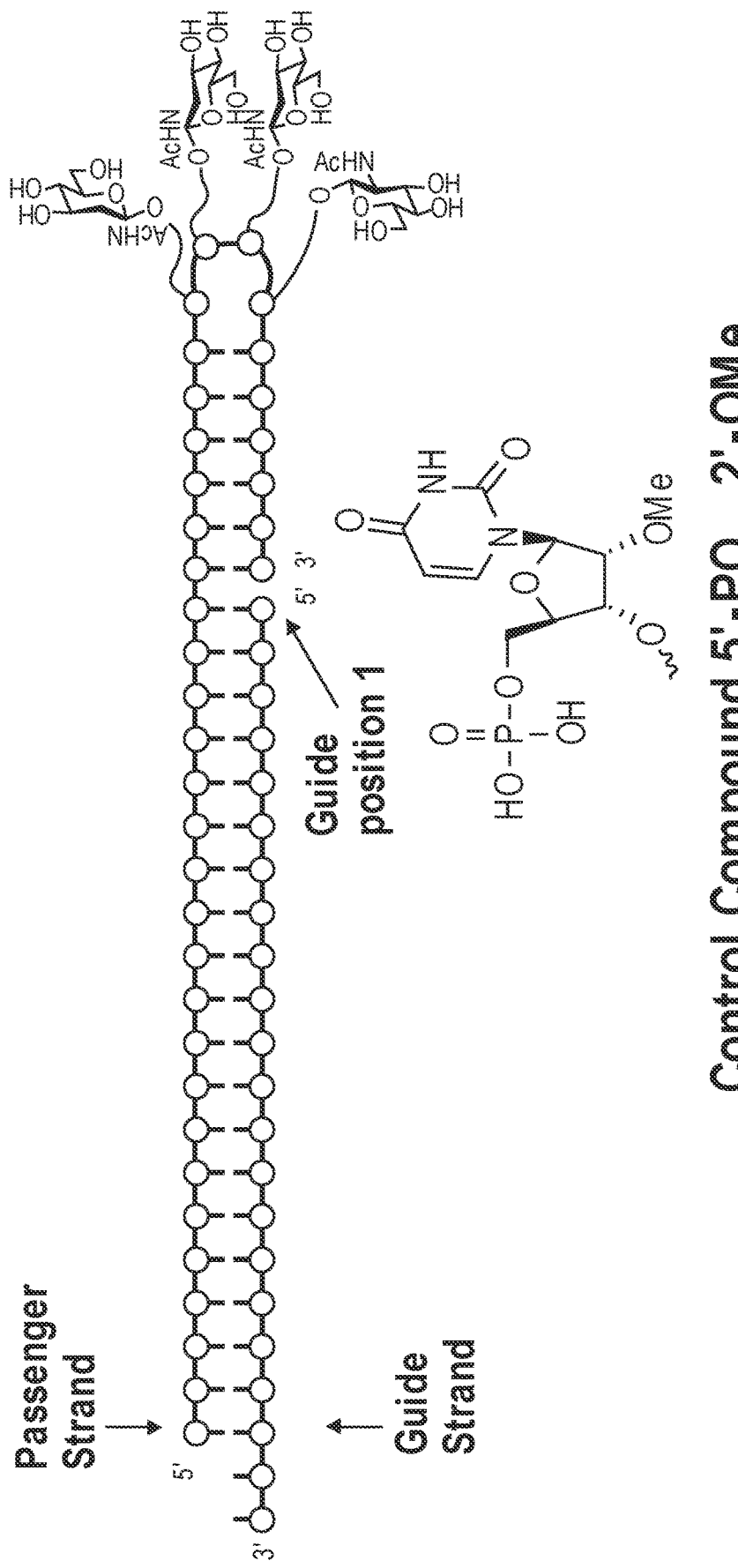
Figure 1D:
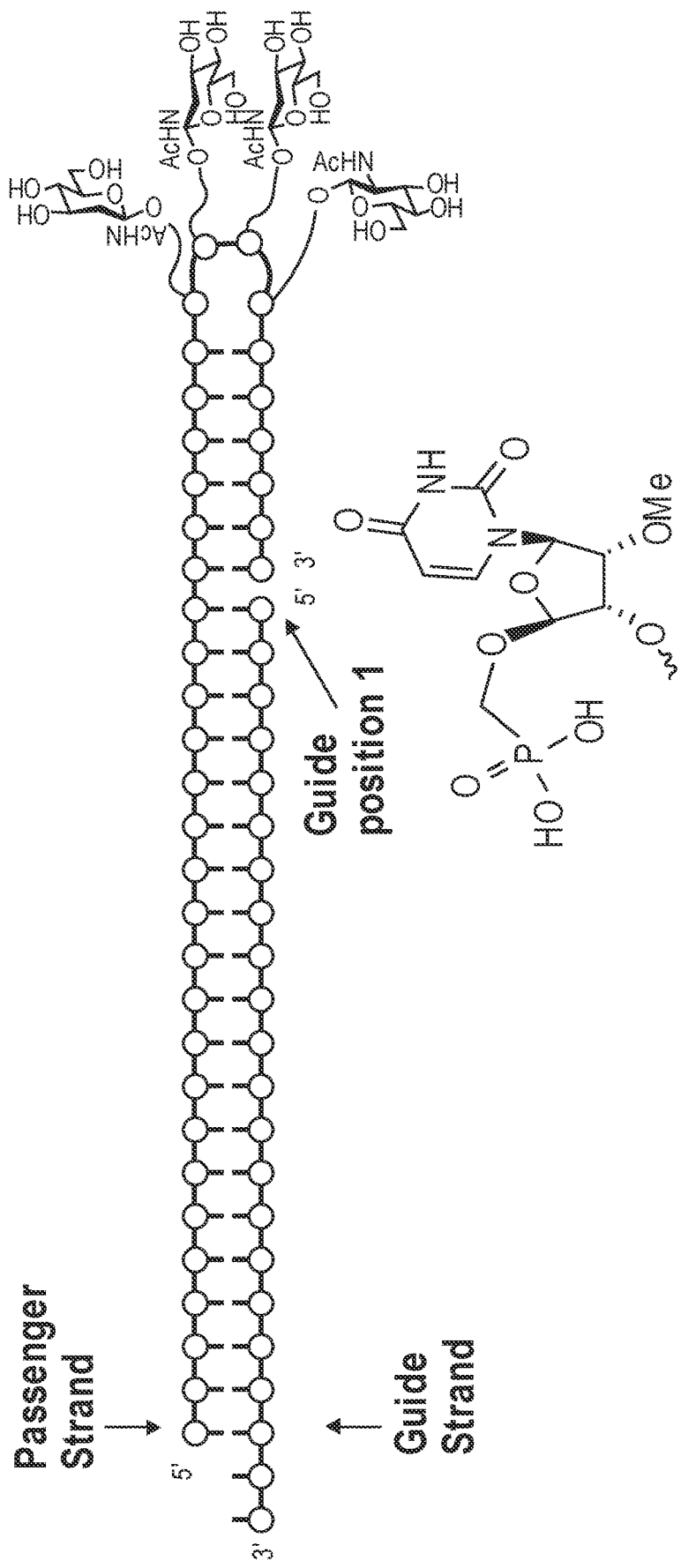
FIG. 1D depicts two representative double stranded RNAi inhibitor molecules as described in the Examples: Test Compound Fully Deprotected, 2'-OMe and Test Compound Monomethyl Protected, 2'-OMe. Test Compound Fully Deprotected, 2'-OMe and Test Compound Monomethyl Protected, 2'-OMe are identical except for the 4'-oxymethylphosphonate group on the N1 nucleotide of the guide strand with the former test compound having a fully deprotected phosphonate group and the latter test compound having a monomethyl protecting group on the phosphonate moiety. Test Compound Fully Deprotected, 2'-OMe and Test Compound Monomethyl Protected, 2'-OMe are identical to Control Compound 5'-OH, 2'-OMe and Control Compound 5'-$PO_4$, 2'-OMe (FIG. 1C) except for the N1 nucleotide of the guide strands, with the control compounds having either a 5'-OH or a 5'-$PO_4$ and the test compounds having a 4'-oxymethylphosphonate.
Figure 1D:
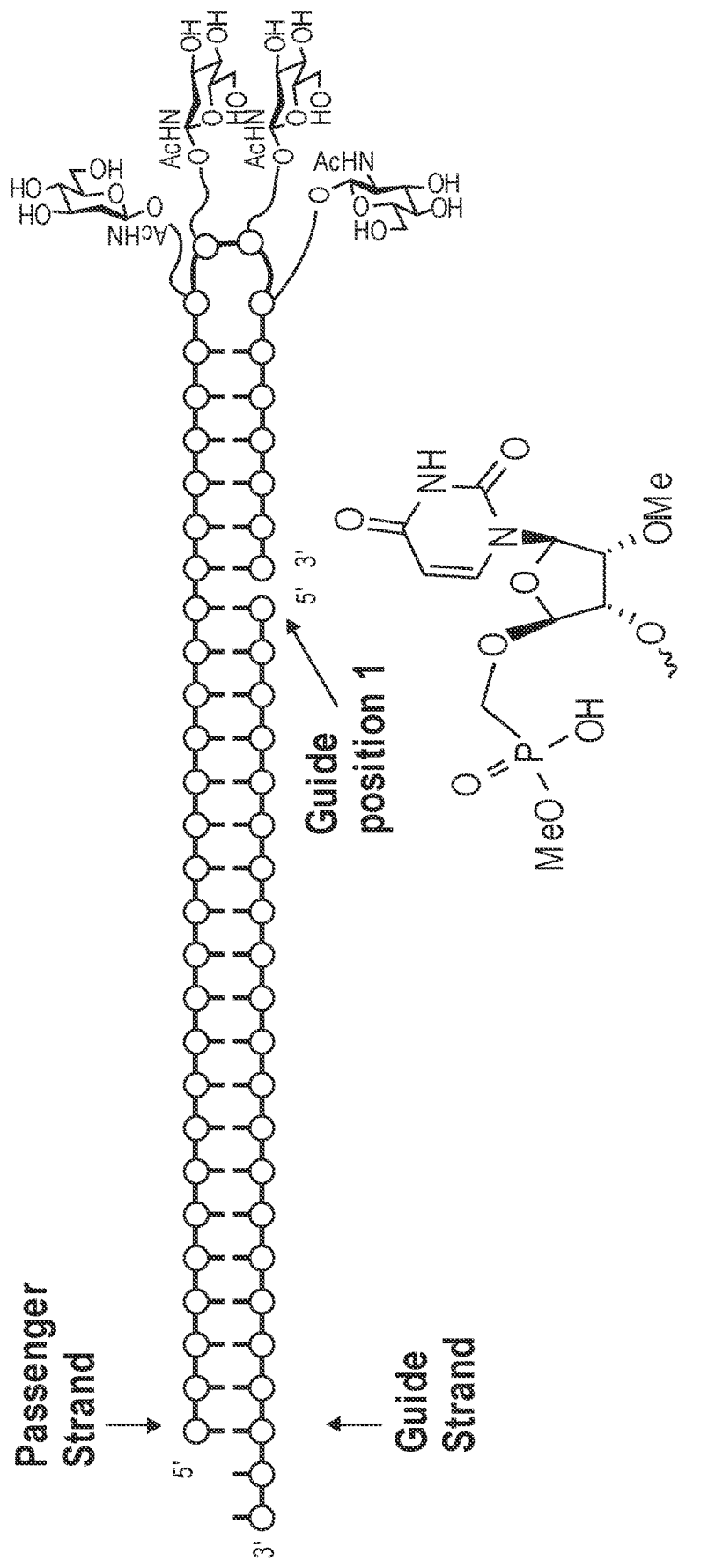
Figure 6B:
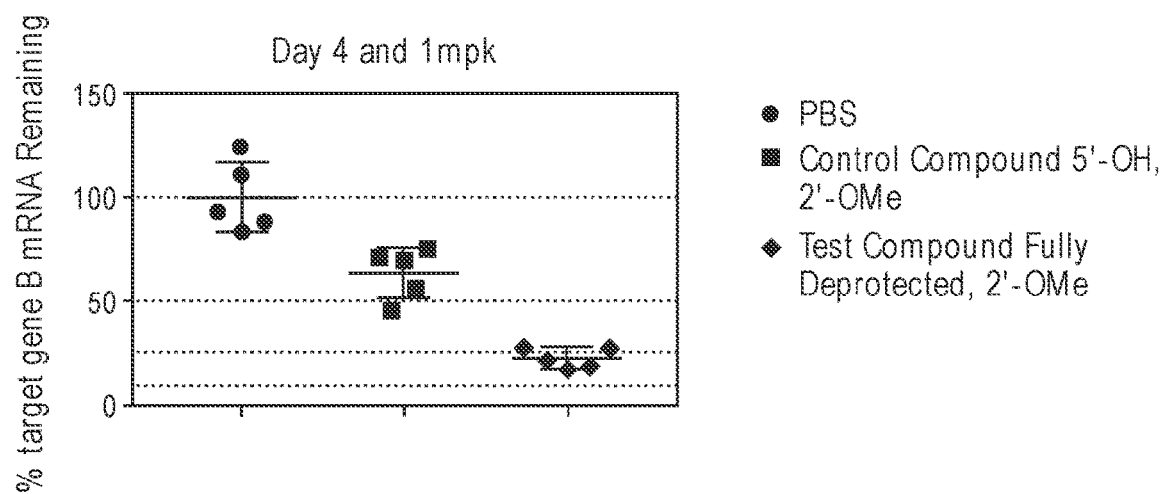
FIG. 6B depicts the potency in mice, as measured by the knockdown of target gene B mRNA, 4 days after the in vivo administration of 1 milligram per kilogram body weight ("mpk") of Control Compound 5'-OH, 2'-OMe or Test Compound Fully Deprotected, 2'-OMe in comparison to a control PBS injection, as described in Example 12.

In a second experiment, CD-1 female mice were dosed subcutaneously at 1 mpk with Control Compound 5'-OH, 2'-OMe and Test Compound Fully Deprotected, 2'-OMe. These compounds are identical except for the nucleotide at position of 1 of the guide strand, as shown in FIGS. 1C and 1D, with the control compound having a 5'-OH and the test compound having a fully deprotected, 4'-oxymethylphosphonate. The inhibition of target gene B mRNA expression was measured at day 4 after dosing. The same trend was observed, with the test compound showing significantly improved gene silencing activity as compared to the control compound at the same dose, demonstrating that the 4'-oxymethylphosphonate improves the in vivo activity of dsRNAi inhibitor molecules. FIG. 6B.

Figure 7:
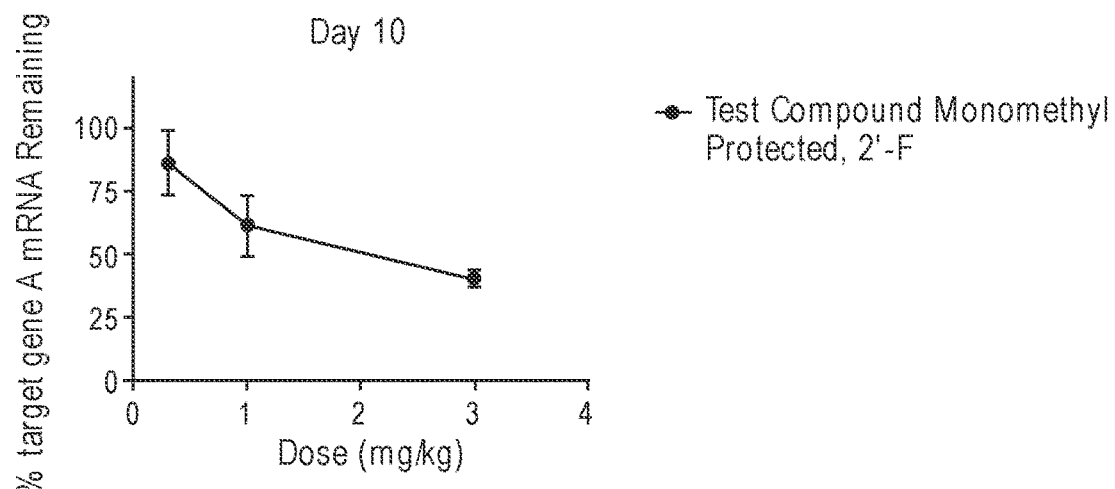
FIG. 7 depicts the in vivo potency in mice in a dose response study, as measured by the knockdown of target gene A mRNA, 10 days after the in vivo administration of Test Compound Monomethyl Protected, 2'-F dosed at 0.3 milligram per kilogram body weight ("mpk"), 1 mpk and 3 mpk, as described in Example 12.

In a third experiment, CD-1 female mice were dosed subcutaneously at 0.3, 1, and 3 mpk body weight with Test Compound Monomethyl Protected, 2'-F. The inhibition of target gene A mRNA expression was measured at day ten after dosing. Test Compound Monomethyl Protected, 2'-F showed dose-dependent knockdown of the target gene mRNA expression. FIG. 7.

Figure 8:
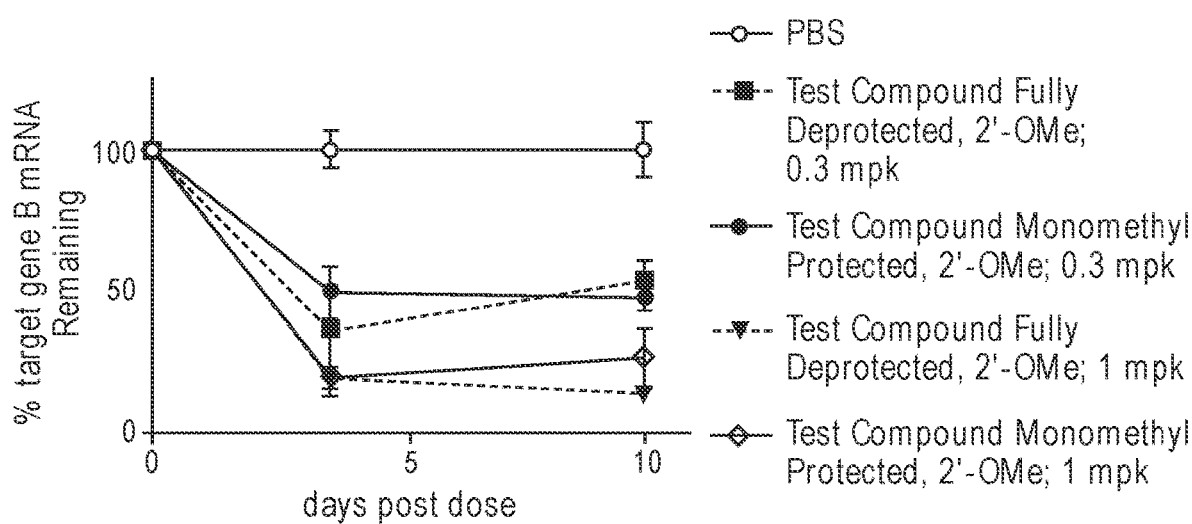
FIG. 8 shows the in vivo potency in mice, as measured by the knockdown of target gene B mRNA, 3 and 10 days after the in vivo administration of Test Compound Fully Deprotected, 2'-OMe and Test Compound Monomethyl Protected, 2'-OMe dosed at 0.3 milligram per kilogram body weight ("mpk") or 1 mpk, as described in Example 12.

In a fourth experiment, CD-1 female mice were dosed subcutaneously at 0.3 or 1 mpk with Test Compound Fully Deprotected, 2'-OMe and Test Compound Monomethyl Protected, 2'-OMe. These two test compounds are identical except for the 4'-oxymethylphosphonate on the nucleotide at position 1 of the guide strand; one of the 4'-oxymethylphosphonates is fully deprotected and the other is protected with a single methyl group (i.e., monomethyl protected), as shown in FIG. 1D. The inhibition of target gene B mRNA expression was measured at days 3 and 10 after dosing. The two compounds showed dose-dependent knockdown and similar potency at both doses and time points. FIG. 8. Without intending to be bound by any theory, it is believed that the monomethyl ester of the 4'-oxymethylphosphonate can convert to fully deprotected 4'-oxymethylphosphonate in vivo.

Example 13: In Vivo Activity of Test Compounds in Non-Human Primates

In a first experiment, male and female cynomologus monkeys were dosed at 3 milligram per kilogram body weight with Control Compound 5'-OH, 2'-OMe and Test Compound Fully Deprotected, 2'-OMe. These two compounds are identical except for the nucleotide at position of 1 of the guide strand, as shown in FIGS. 1C and 1D, with the control compound having a 5'-OH group and the test compound having a fully deprotected, 4'-oxymethylphosphonate. In a second experiment, male and female cynomologus monkeys were dosed at 3 milligram per kilogram body weight with Test Compound Fully Deprotected, 2'-OMe and Test Compound Monomethyl Protected, 2'-OMe. These two test compounds are identical except for the 4'-oxymethylphosphonate on the nucleotide at position 1 of the guide strand; one of the 4'-oxymethylphosphonates is fully deprotected and the other is protected with a single methyl group (i.e., monomethyl protected), as shown in FIG. 1D. The double-stranded nucleic acid inhibitor molecules were administered subcutaneously at a volume of 10 ml/kg. A control group was dosed with phosphate buffered saline (PBS).

Animals were fasted overnight prior to all sample collections. On study days −7, 14, 28, and 56, animals were sedated and a percutaneous liver biopsy sample of approximately 20 mg was collected. The tissue sample was weighed and split in half for preservation in RNAlater® or stored at −70° C. Reduction of target mRNA was measured by qPCR using CFX384 TOUCH™ Real-Time PCR Detection System (BioRad Laboratories, Inc., Hercules, CA). All animal samples were first normalized to their own pre-dose control sample and then to the PBS treated control animals and plotted using GraphPad Prism software (GraphPad Software Inc., La Jolla, CA).

Figure 9A:
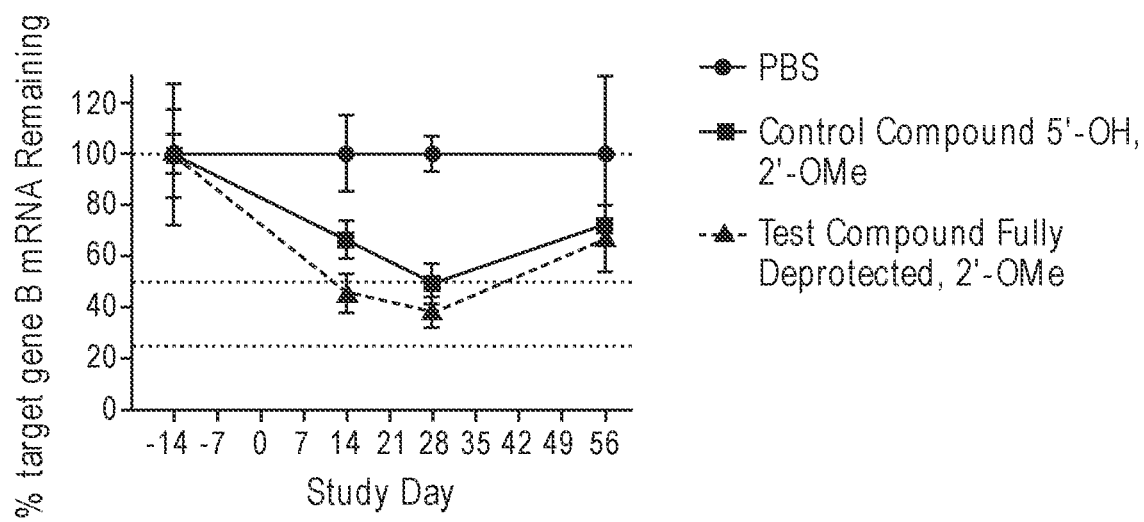
FIG. 9A shows the results of a time course study in cynomologus monkeys, as measured by the knockdown of target gene B mRNA at 14, 28, and 56 days after the in vivo administration of 3 milligram per kilogram of Control Compound 5'-OH, 2'-OMe and Test Compound Fully Deprotected, 2'-OMe, as described in Example 13.
Figure 9B:
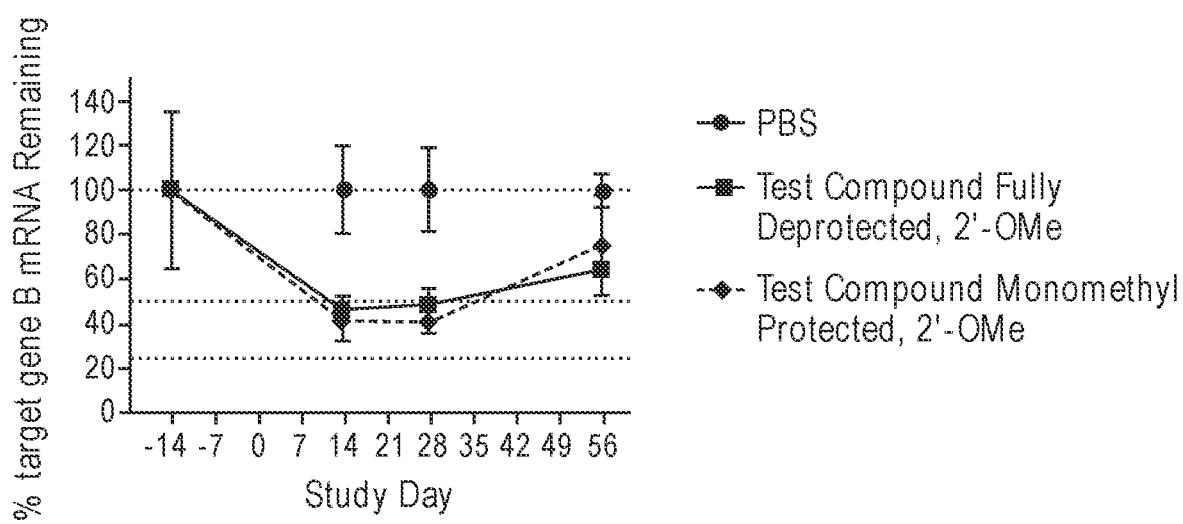
FIG. 9B shows the results of a time course study in cynomologus monkeys, as measured by the knockdown of target gene B mRNA at 14, 28, and 56 days after the in vivo administration of 3 milligram per kilogram of Test Compound Fully Deprotected, 2'-OMe and Test Compound Monomethyl Protected, 2'-OMe, as described in Example 13.

In the first experiment, Test Compound Fully Deprotected, 2'-OMe showed better mRNA reduction activity as compared to Control Compound 5'-OH, 2'-OMe at day fourteen and day twenty eight, demonstrating that the presence of a 4'-oxymethylphosphonate improves the in vivo activity of RNAi inhibitor molecules in cynomologus monkeys. FIG. 9A. In the second experiment, both test compounds (fully deprotected and monomethyl protected) showed similar activity at all time points. FIG. 9B.

We Claim:

1. An oligonucleotide comprising a 5'-terminal nucleotide, wherein the 5'-terminal nucleotide is represented by Formula I or II:

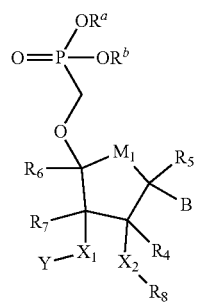

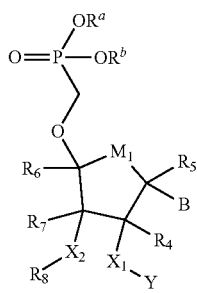

wherein $R^a$ and $R^b$ is each independently selected from hydrogen, $CH_3$, $CH_2CH_3$, $CH_2CH_2CN$, $CH_2OCOC(CH_3)_3$, $CH_2OCH_2CH_2Si(CH_3)_3$, or a protecting group;

wherein B is a natural nucleobase, a modified nucleobase, a universal base or absent;

wherein $M_1$ is O, S, NR', CR'R";

wherein $R_4$, $R_5$, $R_6$, or $R_7$ is each independently selected from hydrogen, halogen, OH, $C_1$-$C_6$ alkyl, $C_1$-$C_6$ haloalkyl or wherein two of $R_4$, $R_5$, $R_6$ and $R_7$ are taken together to form a 5-8 membered ring, wherein the ring optionally contains a heteroatom;

wherein $X_1$ is absent or selected from O, S, NR', or CR'R";

wherein Y is an internucleotide linking group attaching the 5'-terminal nucleotide to an oligonucleotide;

wherein $R_8$ is a glutathione-sensitive moiety or absent;

wherein if $R_8$ is a glutathione-sensitive moiety, $X_2$ is O, S, Se, or NR', or if $R_8$ is absent, $X_2$ is H, OH, SH, $NH_2$, halogen, optionally substituted alkoxy, optionally substituted alkyl, optionally substituted alkenyl, optionally substituted alkynyl, optionally substituted alkylthio, optionally substituted alkylamino or dialkylamino wherein one or more methylenes in the alkyl, alkenyl, and alkynyl may be interrupted with one or more of O, S, S(O), $SO_2$, N(R'), C(O), N(R')C(O)O, OC(O)N(R') optionally substituted aryl, optionally substituted heteroaryl, optionally substituted heterocyclic or optionally substituted cycloalkyl, O, S, Se or NHR'; and wherein R' and R" are each independently hydrogen, a halogen, a substituted or unsubstituted aliphatic, a substituted or unsubstituted aryl, a substituted or unsubstituted heteroaryl, a substituted or unsubstituted heterocycle or a substituted or unsubstituted cycloalkyl.

2. The oligonucleotide of claim 1, wherein;
a) the 5'-terminal nucleotide is represented by Formula I;
b) the 5'-terminal nucleotide e is represented by Formula I, wherein $X_2$ is OH, F, $OCH_2CH_2OCH_3$, or $OCH_3$ and $R_8$ is absent or wherein $X_2$ is O and $R_8$ is a glutathione-sensitive moiety;
c) the 5'-terminal nucleotide is represented by Formula I, and $R^a$ and $R^b$ are hydrogen; $R^a$ is $CH_3$ or $CH_2CH_3$ and $R^b$ is hydrogen; or $R^a$ and $R^b$ are each $CH_3$ or $CH_2CH_3$; or
d) the 5'-terminal nucleotide is represented by Formula I, wherein $X_2$ is OH, F, $OCH_2CH_2OCH_3$, or $OCH_3$ and $R_8$ is absent or wherein $X_2$ is O and $R_8$ is a glutathione-sensitive moiety, and $R^a$ and $R^b$ are hydrogen; $R^a$ is $CH_3$ or $CH_2CH_3$ and $R^b$ is hydrogen; or $R^a$ and $R^b$ are each $CH_3$ or $CH_2CH_3$.

3. The oligonucleotide of claim 1, wherein $R^a$ and $R^b$ are hydrogen; $R^a$ is $CH_3$ or $CH_2CH_3$ and $R^b$ is hydrogen; or $R^a$ and $R^b$ are each $CH_3$ or $CH_2CH_3$.

4. An oligonucleotide comprising a 5'-terminal nucleotide, wherein the 5'-terminal nucleotide comprises an 4'-oxymethylphosphonate, wherein the 4'-oxymethylphosphonate is —O—$CH_2$—PO(OH)$_2$ or —O—$CH_2$—PO(OR)$_2$, wherein R is independently selected from H, $CH_3$, an alkyl group, or a protecting group.

5. The oligonucleotide according to claim 4, wherein the alkyl group is $CH_2CH_3$.

6. The oligonucleotide according to claim 1, wherein the oligonucleotide is a double-stranded RNAi inhibitor molecule comprising a first strand and a second strand, wherein the first strand is a sense strand and the second strand is an antisense strand, and wherein double stranded RNAi inhibitor molecule comprises a region of complementarity between the sense strand and the antisense strand of 15 to 45 nucleotides.

7. The oligonucleotide according to claim 6, wherein the region of complementarity between the sense strand and the antisense strand is 20 to 30 nucleotides, 21 to 26 nucleotides, 19 to 24 nucleotides, or 19 to 21 nucleotides.

8. The oligonucleotide according to claim 6, wherein the 5'-terminal nucleotide is located on the antisense strand.

9. The oligonucleotide according to claim 6, wherein the 5'-terminal nucleotide is located on the sense strand.

10. The oligonucleotide according to claim 6, wherein the double-stranded RNAi inhibitor molecule contains a tetraloop.

11. The oligonucleotide according to claim 1, wherein the oligonucleotide is a single stranded oligonucleotide.

12. The oligonucleotide according to claim 11, wherein the single stranded oligonucleotide is a single stranded RNAi inhibitor molecule.

13. The oligonucleotide according to claim 11, wherein the single-stranded oligonucleotide is a conventional antisense oligonucleotide, a ribozyme or an aptamer.

14. The oligonucleotide according to claim 12, wherein the single stranded RNAi inhibitor molecule is 14-50, 16-30, 18-22, or 20-22 nucleotides in length.

15. The oligonucleotide according to claim 1, wherein the oligonucleotide is a naked oligonucleotide.

16. The oligonucleotide according to claim 1, further comprising at least one delivery agent, wherein the at least one delivery agent is conjugated to the oligonucleotide to facilitate transport of the oligonucleotide across an outer membrane of a cell.

17. The oligonucleotide according to claim 1, wherein the delivery agent is selected from the group consisting of carbohydrates, peptides, lipids, vitamins and antibodies.

18. The oligonucleotide according to claim 1, wherein the delivery agent is selected from N-Acetylgalactosamine (GalNAc), mannose-6-phosphate, galactose, oligosaccharide, polysaccharide, cholesterol, polyethylene glycol, folate, vitamin A, vitamin E, lithocholic acid and a cationic lipid.

19. A pharmaceutical composition comprising the oligonucleotide according to claim 6 and a pharmaceutically acceptable excipient.

20. A method for reducing expression of a target gene in a subject comprising administering the pharmaceutical composition of claim 19 to a subject in need thereof in an amount sufficient to reduce expression of the target gene.

21. The method of claim 20, wherein the administering comprises systemic administration.

22. A nucleoside phosphoramidite, wherein the nucleoside phosphoramidite is represented by Formula X or Formula XI:

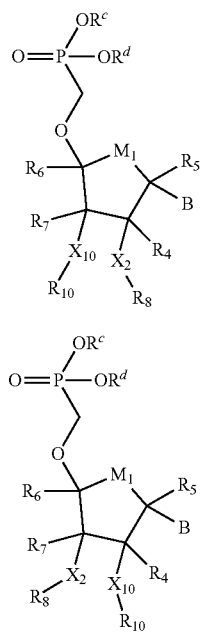

wherein $R^c$ and $R^d$ is each independently selected from $CH_3$, $CH_2CH_3$, $CH_2CH_2CN$, $CH_2OCOC(CH_3)_3$, $CH_2OCH_2CH_2Si(CH_3)_3$, or a protecting group;

wherein B is a natural nucleobase, a modified nucleobase, a universal base or absent;

wherein $M_1$ is O, S, NR', CR'R";

wherein $R_4$, $R_5$, $R_6$, or $R_7$ is each independently selected from hydrogen, halogen, OH, $C_1$-$C_6$ alkyl, $C_1$-$C_6$ haloalkyl or wherein two of $R_4$, $R_5$, $R_6$ and $R_7$ are taken together to form a 5-8 membered ring, wherein the ring optionally contains a heteroatom;

wherein $X_{10}$ is absent or selected from O, S, NR', or CR'R";

wherein $R_{10}$ is a phosphoramidite wherein $R_8$ is a glutathione-sensitive moiety or absent;

wherein if $R_8$ is a glutathione-sensitive moiety, $X_2$ is O, S, Se, or NR'; or wherein if $R_8$ is absent, $X_2$ is H, OH, SH, $NH_2$, halogen, optionally substituted alkoxy, optionally substituted alkyl, optionally substituted alkenyl, optionally substituted alkynyl, optionally substituted alkylthio, optionally substituted alkylamino or dialkylamino wherein one or more methylenes in the alkyl, alkenyl, and alkynyl may be interrupted with one or more of O, S, S(O), $SO_2$, N(R'), C(O), N(R')C(O)O, OC(O)N(R') optionally substituted aryl, optionally substituted heteroaryl, optionally substituted heterocyclic or optionally substituted cycloalkyl, O, S, Se or NHR'; and wherein R' and R" are each independently hydrogen, a halogen, a substituted or unsubstituted aliphatic, a substituted or unsubstituted aryl, a substituted or unsubstituted heteroaryl, a substituted or unsubstituted heterocycle or a substituted or unsubstituted cycloalkyl.

23. The nucleoside phosphoramidite of claim 22, wherein:
a) $M_1$ is O and $X_{10}$ is O;
b) $X_2$ is O and $R_8$ is a glutathione-sensitive moiety;
c) $M_1$ is O, $X_2$ is O, $X_{10}$ is O, and $R_8$ is a glutathione-sensitive moiety;
d) $X_2$ is F, $OCH_2CH_2OCH_3$ or $OCH_3$ and $R_8$ is absent;
e) $M_1$ is O, $X_2$ is F, $OCH_2CH_2OCH_3$ or $OCH_3$, $X_{10}$ is O, and $R_8$ is absent;
f) $M_1$ is O, $X_{10}$ is O, $R^c$ and $R^d$ are each $CH_3$ or wherein $R^c$ and $R^d$ are each $CH_2CH_3$;
g) $X_2$ is O, $R_8$ is a glutathione-sensitive moiety, and $R^c$ and $R^d$ are each $CH_3$ or wherein $R^c$ and $R^d$ are each $CH_2CH_3$;
h) $M_1$ is O, $X_2$ is O, $X_{10}$ is O, $R_8$ is a glutathione-sensitive moiety, and $R^c$ and $R^d$ are each $CH_3$ or wherein $R^c$ and $R^d$ are each $CH_2CH_3$;
i) $X_2$ is F, $OCH_2CH_2OCH_3$ or $OCH_3$, $R_8$ is absent, and $R^c$ and $R^d$ are each $CH_3$ or wherein $R^c$ and $R^d$ are each $CH_2CH_3$; or
i) $M_1$ is O, $X_2$ is F, $OCH_2CH_2OCH_3$ or $OCH_3$, $X_{10}$ is O, $R_8$ is absent, and $R^c$ and $R^d$ are each $CH_3$ or wherein $R^c$ and $R^d$ are each $CH_2CH_3$.

24. The nucleoside phosphoramidite of claim 22, wherein $R^c$ and $R^d$ are each $CH_3$ or wherein $R^c$ and $R^d$ are each $CH_2CH_3$.

25. The oligonucleotide according to claim 1, wherein the oligonucleotide is a double-stranded oligonucleotide comprising a first strand and a second strand.

26. The oligonucleotide according to claim 25, wherein the each strand of the double-stranded oligonucleotide is 15-100 or 15-50 nucleotides in length.

* * * * *

UNITED STATES PATENT AND TRADEMARK OFFICE
CERTIFICATE OF CORRECTION

| | | |
|---|---|---|
| PATENT NO. | : 12,037,586 B2 | Page 1 of 1 |
| APPLICATION NO. | : 17/859781 | |
| DATED | : July 16, 2024 | |
| INVENTOR(S) | : Weimin Wang et al. | |

It is certified that error appears in the above-identified patent and that said Letters Patent is hereby corrected as shown below:

In the Claims

Column 68, Line 49: "the each" should be --each--

Signed and Sealed this
Twenty-ninth Day of October, 2024

Katherine Kelly Vidal
*Director of the United States Patent and Trademark Office*